United States Patent
Schneider et al.

(10) Patent No.: US 11,904,057 B2
(45) Date of Patent: Feb. 20, 2024

(54) NANOPARTICLE-HYDROGEL COMPOSITE FOR NUCLEIC ACID MOLECULE DELIVERY

(71) Applicant: The United States of America, as represented by the Secretary, Department of Health and Human Services, Bethesda, MD (US)

(72) Inventors: Joel Schneider, Frederick, MD (US); Poulami Majumder, Frederick, MD (US); Chuong Hoang, Bethesda, MD (US); Anand Singh, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 531 days.

(21) Appl. No.: 16/967,302

(22) PCT Filed: Feb. 8, 2019

(86) PCT No.: PCT/US2019/017354
§ 371 (c)(1),
(2) Date: Aug. 4, 2020

(87) PCT Pub. No.: WO2019/157381
PCT Pub. Date: Aug. 15, 2019

(65) Prior Publication Data
US 2020/0360296 A1    Nov. 19, 2020

Related U.S. Application Data

(60) Provisional application No. 62/628,961, filed on Feb. 10, 2018.

(51) Int. Cl.
| | | |
|---|---|---|
| *A61K 9/51* | (2006.01) | |
| *A61K 31/7105* | (2006.01) | |
| *A61K 47/64* | (2017.01) | |
| *A61K 47/69* | (2017.01) | |
| *A61K 45/06* | (2006.01) | |
| *B82Y 5/00* | (2011.01) | |

(52) U.S. Cl.
CPC ........ *A61K 9/5169* (2013.01); *A61K 31/7105* (2013.01); *A61K 47/6455* (2017.08); *A61K 47/6929* (2017.08); *A61K 45/06* (2013.01); *B82Y 5/00* (2013.01)

(58) Field of Classification Search
CPC .............. A61K 9/5169; A61K 47/6455; A61K 47/6929; A61K 31/7105; A61K 45/06; B82Y 5/00
See application file for complete search history.

(56) References Cited

U.S. PATENT DOCUMENTS

| | | | | |
|---|---|---|---|---|
| 7,858,585 B2 * | 12/2010 | Ozbas | ...................... | C07K 7/08 514/21.4 |
| 2010/0034881 A1 | 2/2010 | Schneider et al. | | |

FOREIGN PATENT DOCUMENTS

| | | | |
|---|---|---|---|
| WO | WO 2007/059491 A2 | 5/2007 | |
| WO | WO 2016/118871 A1 | 7/2016 | |
| WO | WO-2016118871 A1 * | 7/2016 | ............. A61B 17/11 |

OTHER PUBLICATIONS

Wang, et al. "Engineered Hydrogels for Local and Sustained Delivery of RNA-Interference Therapies," Adv. Healthcare Mater. 2017, 6, 1601041, 1-16). (Year: 2017).*
Minor, et al. "Measurement of the b-sheet-forming propensities of amino acids," Nature, vol. 367, Feb. 17, 1994, 660-663. (Year: 1994).*
Ardekani and Naeini, "The Role of MicroRNAs in Human Diseases," *Med Biotech.* 2.4: 161-179, 2010.
Habibi et al., "Self-Assembled Peptide-Based Nanostructures: Smart Nanomaterials Toward Targeted Drug Delivery," *Nano Today* 11: 41-60, 2016.
Haines-Butterick et al., "Controlling Hydrogelation Kinetics by Peptide Design for Three-Dimensional Encapsulation and Injectable Delivery of Cells," *Proc Natl Acad Sci USA* 104.19: 7791-7796, May 2007.
Nagy-Smith et al., "Protein Release from Highly Charged Peptide Hydrogel Networks," *J Mat Chem B.* 4: 1999-2007, Feb. 2016.
Rupaimoole and Slack, "MicroRNA Therapeutics: Towards a New Era for the Management of Cancer and Other Diseases," *Nat Rev.* 16: 203-221, Mar. 2017.
Schneider et al., "Responsive Hydrogels from the Intramolecular Folding and Self-Assembly of a Designed Peptide," *J Am Chem Soc.* 124: 15030-15037, 2002.
Segovia et al., "Hydrogel Doped with Nanoparticles for Local Sustained Release of siRNA in Breast Cancer," *Adv Healthcare Mater.* 4: 271-280, 2015.
Shukla et al., "Peptides Used in the Delivery of Small Noncoding RNA," *Mol Pharmaceutics* 11: 3395-3408, Aug. 2014.
Sinthuvanich et al., "Iterative Design of Peptide-Based Hydrogels and the Effect of Network Electrostatics on Primary Chondrocyte Behavior," *Biomaterials* 33.30: 7478-7488, Oct. 2012.

(Continued)

*Primary Examiner* — Michael P Cohen
(74) *Attorney, Agent, or Firm* — Klarquist Sparkman, LLP

(57) ABSTRACT

This disclosure provides novel peptide hydrogels containing encapsulated nanoparticles comprising nucleic acid molecules (such as miRNA) that can undergo multiple gel-to-solution (gel-sol) and solution-to-gel (sol-gel) phase transitions, and their use, such as for controlled delivery of nucleic acid molecules to a subject.

32 Claims, 47 Drawing Sheets
Specification includes a Sequence Listing.

(56) References Cited

OTHER PUBLICATIONS

Wang and Burdick, "Engineered Hydrogels for Local and Sustained Delivery of RNA-Interference Therapies," *Adv Healthcare Mater.* 6: 1601041, 2017 (16 pages).
Xu et al., "miR-1 Induces Growth Arrest and Apoptosis in Malignant Mesothelioma," *Chest* 144.5: 1632-1643, Nov. 2013.
Zhang et al., "Cell-Free 3D Scaffold with Two-Stage Delivery of miRNA-26a to Regenerate Critical-Sized Bone Defects," *Nat Comm.* 7: 10376, Jan. 2016 (15 pages).
Chen et al., "Design and characterization of a new peptide vector for short interfering RNA delivery," *J Nanobiotechnology* 13: 39, Jun. 2015 (10 pages).

\* cited by examiner

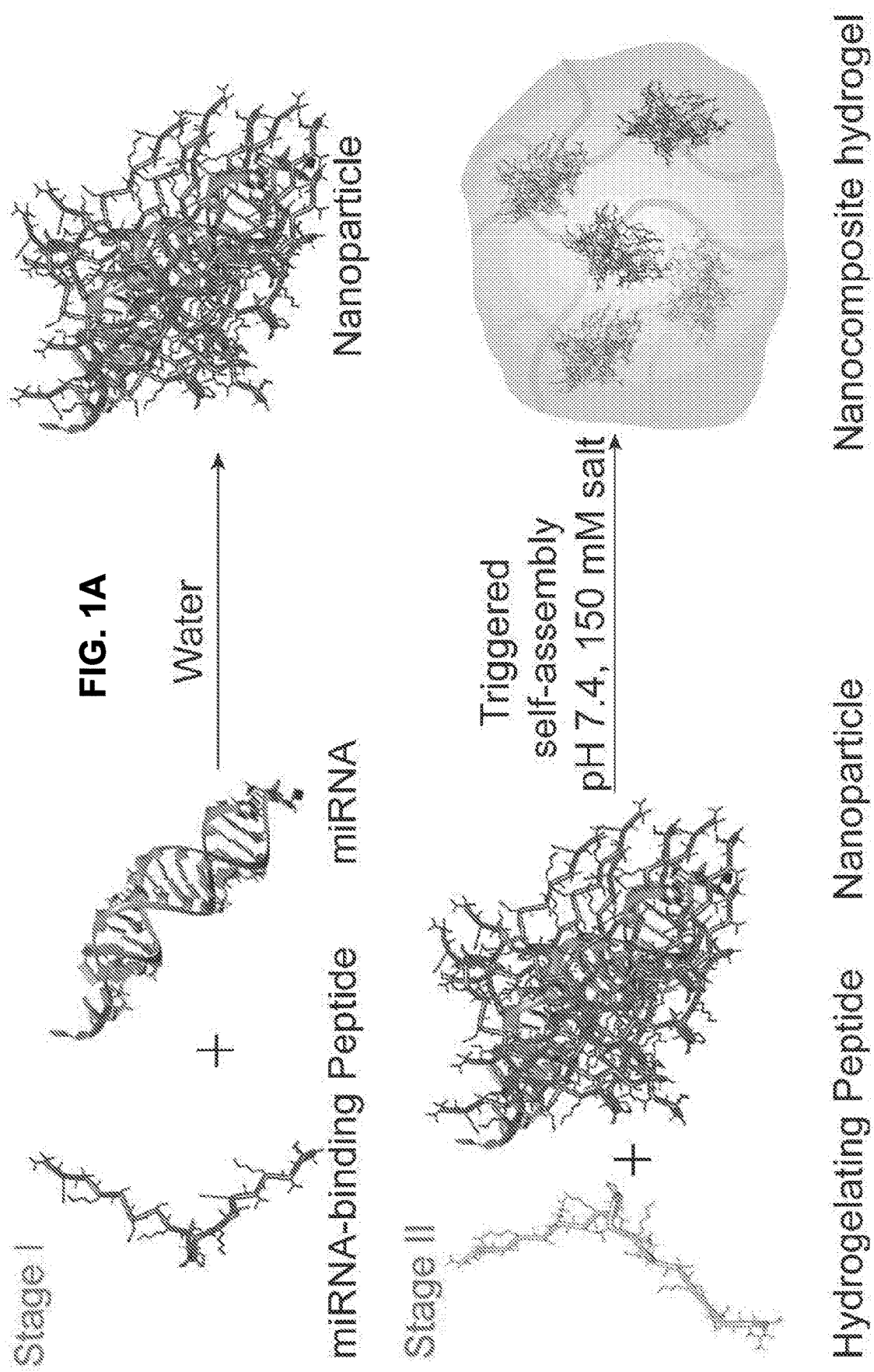

Complex anatomic surface

Peptide 1 (+9): VKVKVKVKV<sup>D</sup>PPTKVKVKVKV-NH₂
Peptide 2 (+7): VKVKVKV<sup>D</sup>PPTKVEVKVKV-NH₂
Peptide 3 (+5): VLTKVKTKV<sup>D</sup>PPTKVEVKVLV-NH₂

NP/Scrambled miRNA   NP/miRNA-215

NP/Scrambled miRNA   NP/miRNA-215

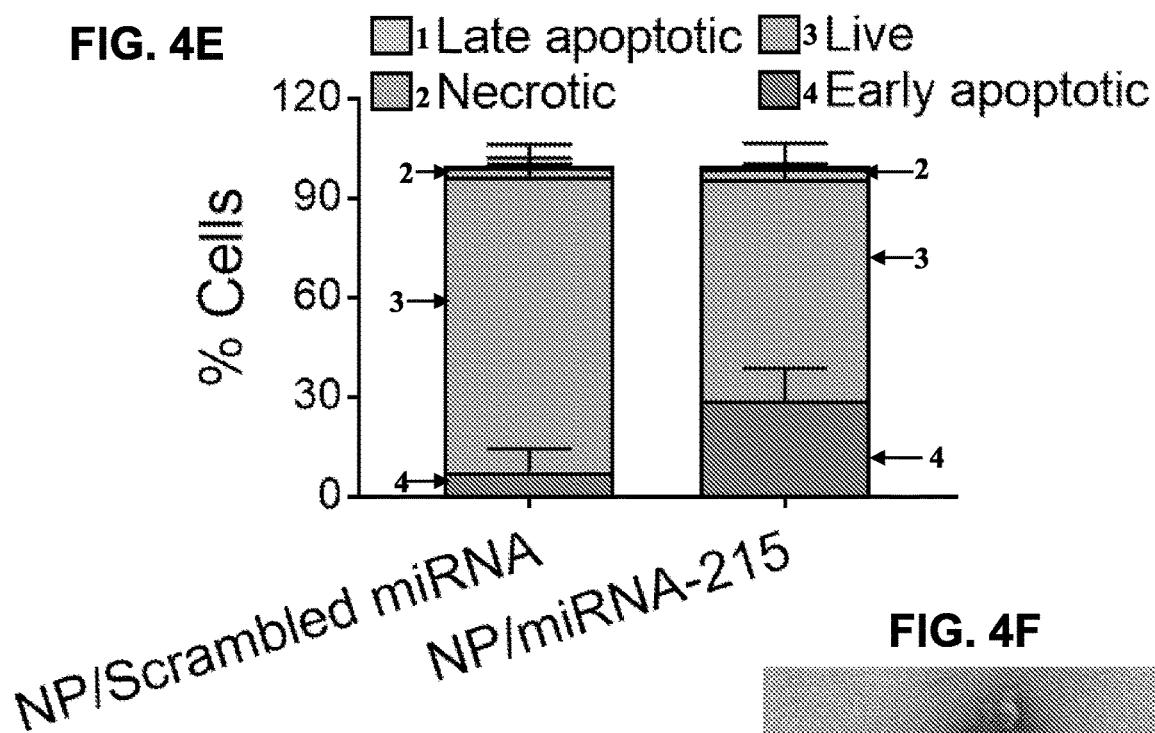
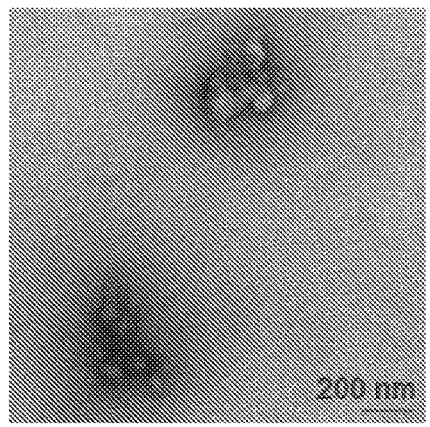
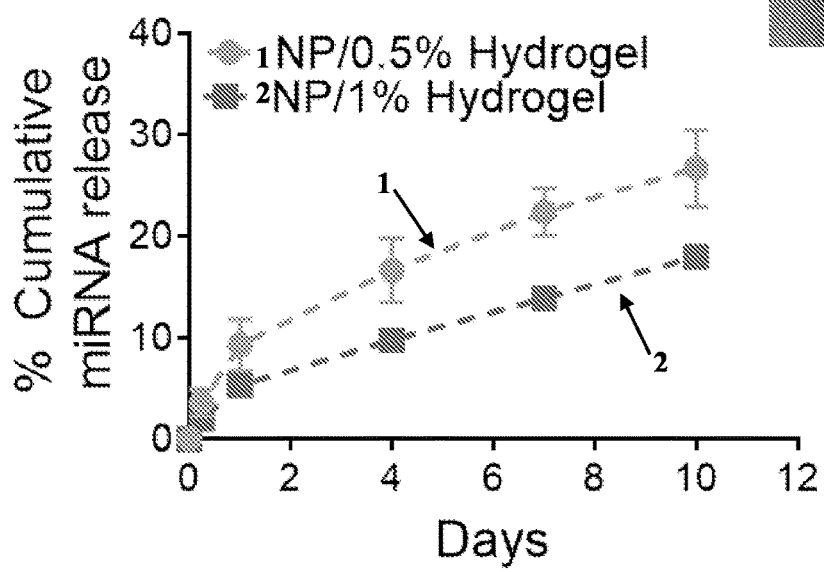
FIG. 4E
FIG. 4F
FIG. 4G

NP/Cy3miRNA in Hydrogel

1. Cells only
2. Lipofectamine
3. Peptide 1
4. Dharmafect
5. In vivo Jet PEI

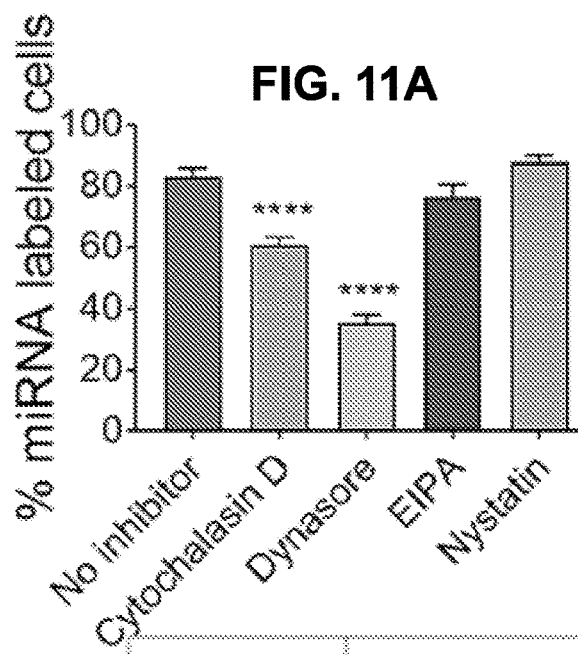

| Inhibitor | Chemical structure | Possible mechanism of endocytic inhibition in H2052 cells | Concentration used in the study |
|---|---|---|---|
| Cytochalasin D | 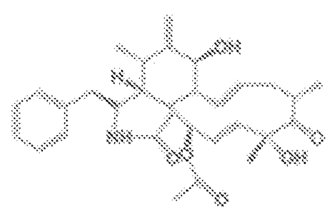 | Inhibits clathrin-mediated endocytosis, induces depolymerization of actin filaments | 20 µM |
| Dynasore | 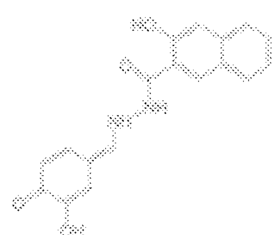 | Inhibits clathrin-mediated and macropinocytic pathways, prevents GTPase activity of Dynamin | 80 µM |
| 5-(N-Ethyl-N-isopropyl)amiloride (EIPA) | 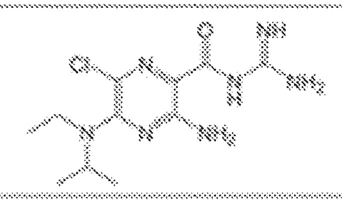 | Inhibits macropinocytic uptake, inhibits $Na^+/H^+$ exchange | 100 µM |
| Nystatin | 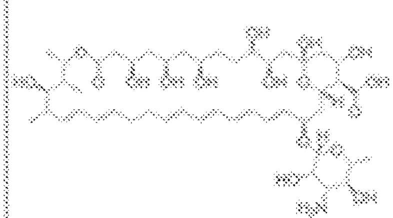 | Inhibits caveolae mediated uptake, sequesters cholesterol and disrupts lipid raft formation | 30 µM |

Hydrogelating peptide 4
AcVEVSVSVEV<sup>D</sup>PPTEVSVEVEVGGGGRGDV-NH2(-5)

FIG. 24A
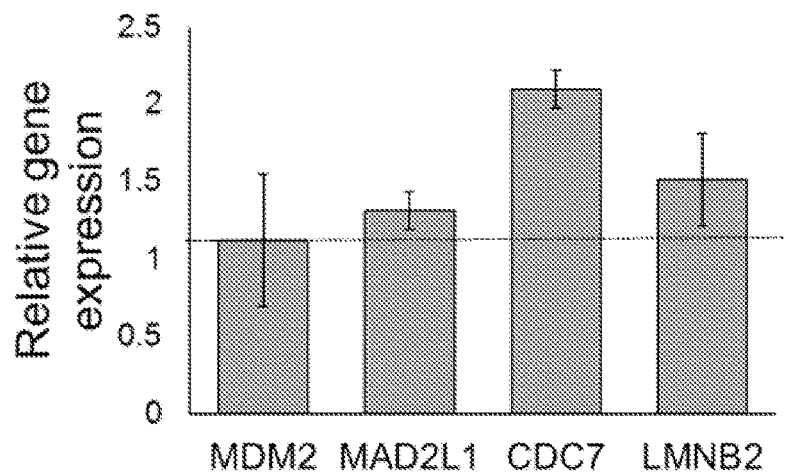
FIG. 24B
FIG. 24C
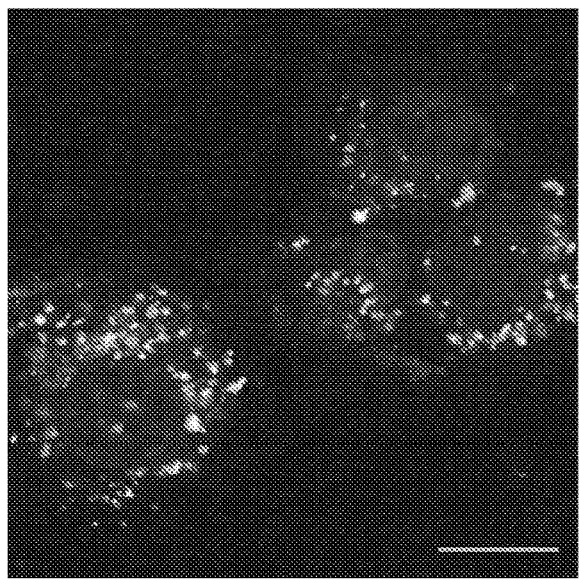
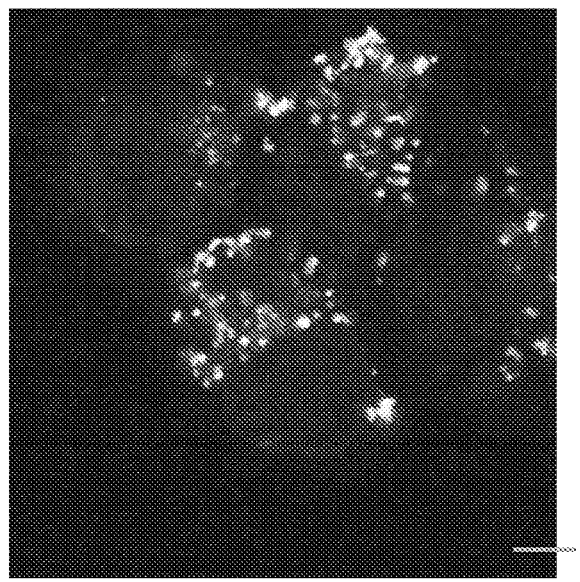

NANOPARTICLE-HYDROGEL COMPOSITE FOR NUCLEIC ACID MOLECULE DELIVERY

CROSS-REFERENCE TO RELATED APPLICATION

This is the U.S. National Stage of International Application No. PCT/US2019/017354, filed Feb. 8, 2019, which was first published in English under PCT Article 21(2), which in turn claims priority to U.S. Provisional Application No. 62/628,961, filed Feb. 10, 2018. The provisional application is incorporated by reference herein in its entirety.

STATEMENT REGARDING FEDERALLY SPONSORED RESEARCH AND DEVELOPMENT

This invention was made with Government Support under project numbers ZIA BC 011313 and 011657 awarded by the National Institutes of Health, National Cancer Institute. The Government has certain rights in this invention.

FIELD OF THE DISCLOSURE

This relates to peptide hydrogels containing encapsulated nanoparticles comprising nucleic acid molecules (such as microRNA), that can undergo multiple gel-to-solution (gel-sol) and solution-to-gel (sol-gel) phase transitions, and their use, for example, for controlled delivery of the nucleic acid molecules to a subject.

BACKGROUND

The use of injectable hydrogels allows the local delivery of encapsulated therapeutics directly to tissue, limiting systemic distribution of the therapeutic and any associated off-target toxicity. However, current strategies for hydrogel-mediated therapeutic delivery still have challenges that must be overcome before becoming clinically viable, particularly in the context of delivery vehicles for nucleic acid-based therapeutics, such as RNA therapeutics.

SUMMARY

Provided herein are embodiments of a peptide hydrogel containing nanoparticles of a peptide complexed with a nucleic acid molecule (nanoparticle-hydrogel composite). The nucleic acid molecule can be, for example, a microRNA (miRNA) or a mimic and/or mimetic thereof. The nanoparticle-hydrogel composite displays shear-thin/recovery mechanical properties, which allow the nanoparticle-hydrogel composite and any additional therapeutic dispersed within the hydrogel to be delivered locally to a target location in a subject, for example, via syringe injection or spray delivery to coat anatomic surfaces at the target location. After delivery, the nanoparticles time-release from the hydrogel matrix to adjacent tissues and are taken up by cells. Once internalized by cells, the nucleic acid molecule is released from the nanoparticle and (depending on the nucleic acid molecule) may affect cellular function.

In some embodiments, a peptide hydrogel is provided that comprises nanoparticles encapsulated within the peptide hydrogel. The nanoparticles comprise a nucleic acid molecule complexed with a first amphiphilic cationic β-hairpin peptide that is unfolded and not in a β-hairpin conformation. The peptide hydrogel is formed from a fibrillar network of a second amphiphilic cationic peptide that is in a β-hairpin conformation. In some examples, the first and second amphiphilic cationic peptides are no more than 50 amino acids in length.

In some examples of the disclosed peptide hydrogel, the first amphiphilic cationic β-hairpin peptide comprises or consists of an amino acid sequence set forth as: VKVKVKVKV$^D$PPTKVKVKVKV-NH$_2$, and the second amphiphilic cationic β-hairpin peptide comprises or consists of an amino acid sequence set forth as: VLTKVKTKV$^D$PPTKVEVKVLV-NH$_2$.

In several embodiments, an electrostatic charge of the first amphiphilic cationic peptide is equal to or more positive than an electrostatic charge of the second amphiphilic cationic peptide at neutral pH. For example, the electrostatic charge of the first amphiphilic cationic peptide is from +7 to +10 (such as +9) and the electrostatic charge of the second amphiphilic cationic peptide is from +3 to +8 (such as +5) at neutral pH.

In some embodiments, the first amphiphilic cationic peptide comprises or consists of an amino acid sequence set forth as:

$$(XZ)_n X\text{-}[{}^DPP, {}^DPG, \text{ or } NG]\text{-}X(ZX)_n$$

wherein each X is individually selected from any one of F, I, L, M, T, V, W, and Y; each Z is individually selected from any one of H, K, Ornithine, and R; n is from 3 to 5; and the peptide has a net formal charge of from +7 to +10 at neutral pH. The C-terminus of the peptide is not carboxylate and comprises a peptide modification having a neutral or positive charge. In some embodiments, the first amphiphilic cationic peptide comprises or consists of an amino acid sequence set forth as: (1d) VKVKVKVKV$^D$PPTKVKVKVKV-NH$_2$ (MAX1 peptide).

In some embodiments, the second amphiphilic cationic peptide comprises or consists of an amino acid sequence set forth as:

$$(XZ)_n X\text{-}[{}^DPP, {}^DPG, \text{ or } NG]\text{-}X(ZX)_n$$

wherein each X is individually selected from F, I, L, M, T, V, W, and Y; each Z is individually selected from any amino acid; n is from 3 to 5; and the peptide has a net formal charge of from +3 to +8 at neutral pH. In some embodiments the second amphiphilic cationic peptide comprises or consists of an amino acid sequence set forth as:

VLTKVKTKV$^D$PPTKVEVKVLV-NH$_2$ (HLT2 peptide).

In some embodiments, the nucleic acid molecule complexed with the first amphiphilic cationic peptide is an antisense nucleic acid molecule. In some embodiments, the nucleic acid molecule complexed with the first amphiphilic cationic peptide is a miRNA or a mimic and/or mimetic thereof.

The peptide hydrogel can further comprise a heterologous anti-cancer agent (such as a chemotherapeutic agent) encapsulated within the peptide hydrogel.

Also provided are methods of treating or inhibiting a cancer in a subject, comprising administering an effective amount of a disclosed peptide hydrogel to a target location in the subject where the cancer is present or is at risk of being present. In such methods, the nanoparticles in the peptide hydrogel comprise a nucleic acid molecule (such as a miRNA or a mimic and/or mimetic thereof) that inhibits the cancer. The peptide hydrogel comprising the nanoparticles can be administrated to the subject by any suitable means, such as direct injection or spray delivery to the target location in the subject. In some embodiments, the target location is a serosal surface lined by mesothelial cells (for example, part of a serosal body cavity such as the pleural space) in the subject. In some embodiments, the cancer is a serosal cancer, such as malignant pleural mesothelioma.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1C. Schematic diagram showing the design of the nanoparticle hydrogel composite and its application for miRNA delivery to complex anatomical surfaces, such as plural cavity surfaces following tumor resection. (FIG. 1A) Two stage process to prepare nanoparticle-hydrogel composite. Nanoparticles are first formulated in Stage I by complexing miRNA to a first amphiphilic cationic peptide that is not in a β-hairpin conformation via electrostatic interaction between the cationic peptide and the anionic miRNA. To encapsulate the nanoparticles into the hydrogel (Stage II), the nanoparticle suspension is mixed with a second amphiphilic cationic peptide in a physiological buffer to induce β-hairpin folding and consequent self-assembly of the second peptide. This triggers formation of a fibrillar composite hydrogel network from the second peptide that homogeneously encapsulates the nanoparticles. (FIG. 1B) The nanoparticle-hydrogel composite can be applied by syringe injection or spray to locally deliver miRNA to cells of complex anatomic surfaces. (FIG. 1C) Application of nanoparticle-hydrogel composite to pleural space following surgical resection of plural mesothelioma tumor and subsequent release of nanoparticles to neighboring tissue and uptake into cells. The applied hydrogel covers the complex resected tissue surface and releases miRNA nanoparticles, which are internalized into remaining tumor cells through clathrin-mediated endocytosis.

(FIG. 2A) Amino acid sequences of peptides, their charges at physiological pH, and binding interaction between peptides and miRNA as monitored by fluorescence spectroscopy. A fixed concentration (30 nM) of FAM-labeled scrambled miRNA was titrated against varying concentrations of peptides. FAM label on miRNA was excited at 490 nm and fluorescence measured at 520 nm for each composition was normalized to that for free FAM-miRNA. (FIG. 2B) Transmission electron micrographs of nanoparticles consisting of miRNA complexed to Peptide 1. Complexation was performed in water at an N/P ratio (charge ratio) of 10:1 for Peptide 1 vs miRNA. Diameters of the particles calculated using ImageJ software is shown at the inset (n=30). (FIG. 2C) Circular dichroism spectra of Peptide 1 with and without complexed miRNA at various N/P ratio, recorded in water at 37° C. [θ] denotes Mean Residue Ellipticity. (FIG. 2D) Percentage of β-sheet present for Peptide 1 when complexed with miRNA at different N/P ratio in water. % β-sheet is derived from CD signal in FIG. 2C, which measures the increase in negative ellipticity at 198 nm. % β-sheet is plotted against zeta potentials of corresponding complexes measured in water.

(FIG. 3A) miRNA transfection efficiency of Peptide 1 as determined from flow cytometric analyses of H2052 cells after 1 h exposure to nanoparticles consisting of FAM-labeled scrambled miRNA. miRNA transfection efficiency of Peptide 1 as compared to commercially available transfection reagents. n=3, error bars in ±SD, **p<0.0001, ANOVA followed by Dunnett's multiple comparison test. (FIG. 3B) Mechanism of miRNA transfection by nanoparticles derived from Peptide 1 in H2052 cells. Median fluorescence intensities of internalized miRNA in presence of endocytic inhibitors were normalized to that in absence of inhibitors. n=3, error bars in ±SD, p<0.0001, p<0.005, *p<0.05, ANOVA & Dunnett's multiple comparison test. Confocal microscopy image of live H2052 cells treated for 0.5 h (FIG. 3C) and 4 h (FIG. 3D) with nanoparticles containing FAM-miRNA and Peptide 1. Co-localization of FAM-miRNA at each time point was determined for late endosome/lysosome marker lysotracker red (LysoT). Nuclei staining is shown. (FIG. 3E) Punctate calcein fluorescence in cells treated with calcein alone for 4 h. (FIG. 3F) Diffused calcein fluorescence in cells co-incubated with calcein and Peptide 1/miRNA nanoparticles (unlabeled scrambled miRNA) for 4 h. Final miRNA concentration is 40 nM in each. Scale bar 10 μm on each image.

FIGS. 4A-4I. Peptide 1 can functionally deliver miRNA-215 to H2052 cells and corresponding miRNA complex can be encapsulated within self-assembling β-hairpin peptide hydrogels for functional miRNA delivery in vitro. (FIG. 4A) Relative levels of cell-cycle transcripts in H2052 cells 48 h post-treatment with Peptide 1/miRNA-215 nanoparticles. Gene expression levels are shown as fold changes with respect to that for the scrambled miRNA treated group. Error bars are in ±SD for n=3. p<0.01, *p<0.001, #p<0.0001, student's t-test. (FIG. 4B) Cell viability of H2052 at 72 h and 120 h post-treatment with the nanoparticles. (FIG. 4C) Clonogenicity assay to determine proliferative capacity of cells treated with the nanoparticles 2 weeks post-treatment. (FIG. 4D) Anchorage-independent growth ability of similarly treated cells 6 weeks after treatment. Quantification of corresponding number of colonies is shown at the inset. (FIG. 4E) Apoptotic effect induced by the nanoparticles 96 h post-treatment, as determined by flow cytometric Annexin V-FITC/PI-based apoptosis assay. (FIG. 4F) Transmission electron micrographs of 0.5% (w/v) Peptide 3 hydrogel with encapsulated nanoparticles. (FIG. 4G) Cumulative release of FAM-miRNA from hydrogels formed via self-assembling Peptide 3 into an infinite sink (HBS) at 37° c. (FIG. 4H) FAM-miRNA was released from the gel composites separately for 24 h and H2052 cells were treated with the release supernatant for 4 h to visualize the uptake of released FAM-miRNA. Cell nuclei were stained. Scale bar 10 μm. (FIG. 4I) Gene silencing efficacies of cells treated with the release supernatant of the gel composites loaded with encapsulated miRNA-215, 48 h after transfection. Error bars are in ±SD for n=3. **p<0.01, #p<0.0001, student's t-test.

(FIG. 5A) Monitoring release of Cy3-labeled miRNA delivered in athymic nu/nu mice from hydrogel composites implanted by syringe injection versus soluble miRNA injected subcutaneously. (FIG. 5B) In vivo degradation of the gel composites as monitored by ultrasound. (FIG. 5C) cy3-labeled miRNA nanoparticle-hydrogel composite delivers miRNA into tumor cells when injected peritumorally in NOD/SCIDγ mice bearing subcutaneous H2373 tumors. Tumors were collected 24 h post-injection. Corresponding z-stacks are also shown. Scale bar 10 μm. (FIG. 5D) Subcutaneous tumor growth inhibition curve (n=5 for therapeutic miRNA treated groups, n=4 for control groups) for different treatment groups after a single peritumoral administration of hydrogel composites. Error bars in ±SEM, *p<0.001, p<0.01 (Student's t test). (FIG. 5E) Images of tumors excised from treated mice on week 4 post-hydrogel injection. (FIG. 5F) Gene expression profiles of cell-cycle transcripts in tumor tissue at week 1 and 2 post-hydrogel administration. Error bars are in ±SEM for n=3 mice, each measured in triplicate. *p<0.05, **p<0.01 (student's t test). Immunohistochemical evaluation of tumors treated with various hydrogel composites for Ki67 (FIG. 5G) to evaluate tumor cell proliferative capacity and for TUNEL (FIG. 5H) to determine apoptotic potential. Tumors were collected at week 4 post treatment. Nuclei in FIG. 5G were stained with DAPI and pseudo-colored to red to aid visualization. Scale bar 10 μm on each image.

(FIG. 6A) Time-line of monitoring tumor growth in mice bearing peritoneal H2373 tumor graft followed by administering a single intraperitoneal injection of hydrogel composites. (FIG. 6B) Tumor growth curve of mice in various treatment groups as determined by measuring luminescence of tumor tissue. Radiant flux around the tumor at each time point was normalized with respect to that on day 0 for each treatment group. Error bars in ±SEM, p<0.01, *p<0.001 (Student's t test, n=10 for therapeutic miRNA treated groups, n=8 for control groups). (FIG. 6C) Live-imaging of tumor luminescence in mice treated with hydrogel composites at different time points. (FIG. 6D) Kaplan-Meier survival curves of mice treated with hydrogel composites (n=10), *p<0.05, **p<0.01, Log-rank (Mantel-Cox) test. (FIG. 6E) Time-line of monitoring tumor growth in mice bearing peritoneal H2052 tumor graft and receiving a single intraperitoneal injection of hydrogel composites. (FIG. 6F) Tumor growth curve of mice in various treatment groups as determined by measuring luminescence of tumor tissue. Error bars in ±SEM, *p<0.05 (Student's t test, n=5 in each group). (FIG. 6G) Live-imaging of tumor luminescence in mice treated with hydrogel composites at different time points. (6H) Kaplan-Meier survival curves of mice treated with hydrogel composites, *p<0.05, Gehan-Breslow-Wilcoxon test.

(FIG. 7A) FAM label on miRNA was excited at 490 nm and fluorescence was measured at 520 nm for miRNA complex of Peptide 1 formulated at N/P ratio of 10:1. Complexation was performed in water and complex suspension was diluted with salt free HEPES (pH 7.4) in presence or absence of heparin before data acquisition. (FIG. 7B) Stability of Peptide 1/miRNA complex as determined by heparin displacement assay. Heparin sulfate solution was added into Peptide 1/FAM-miRNA complex diluted in 25 mM HEPES (pH 7.4) to a final heparin concentration of 50 μg/mL, incubated at 37° C. for 1 h and miRNA fluorescence was measured at 520 nm. (FIG. 7C) Circular dichroism spectra of Peptide 1 complexed with miRNA at N/P ratio 10:1 in presence or absence of increasing concentration of heparin, as recorded in water at 37° C. [θ] denotes Mean Residue Ellipticity.

(FIG. 9A) Overlaid flow cytometric histograms indicating miRNA transfection efficiency of Peptide 1 as compared to commercially available transfection reagents. (FIG. 9B) Percentage of cells transfected with miRNA delivered in each case for 1 h post-exposure. n=3, error bars in ±SD, ****p<0.0001, student's t-test.

FIGS. 11A-11C. Mechanism of miRNA transfection by nanoparticles derived from Peptide 1 in H2052 cells. (FIG. 11A) Percentage of cells labeled with FAM-miRNA at 1 h post-exposure to the nanoparticles in presence and absence of endocytic inhibitors. n=3, error bars in ±SD, ****p<0.0001, ANOVA followed by Dunnett's multiple comparison test with respect to "No inhibitor" group. (FIG. 11B) Structures and functions of endocytosis inhibitors used in current study, concentrations these are used in and corresponding references in the text. Flow cytometric histograms of cells treated with the nanoparticles for 1 h in presence or absence of Cytochalasin D, Dynasore, EIPA or Nystatin. (FIG. 11C) Flow cytometric histograms of cells treated with the nanoparticles for 1 h in presence or absence of Cytochalasin D, Dynasore, EIPA or Nystatin.

(FIG. 12C) Confocal microscopy image of live H2052 cells treated for 4 h with dually-labeled nanoparticles containing FAM-miRNA and Peptide 1. Nuclei were stained as shown. Final miRNA concentration is 40 nM in each panel. Scale bar 10 μm.

(FIG. 13A) Effects of transfected miRNA-215 on cellular signaling pathways of H2052 human mesothelioma. (FIG. 13B) Viability of H2052 cells treated with soluble Peptide 1 and Peptide 1/scrambled miRNA nanoparticles 4 h post-incubation as determined by MTT assay. (FIG. 13C) Cytotoxicity of soluble Peptide 1 and corresponding nanoparticles were determined in H2052 cells using Lactate Dehydrogenase assay 4 h post-incubation. In each case, Triton X-100 was taken as positive control.

(FIG. 15A) Images of hydrogel composites consisting of varying hydrogelating peptides and different nanoparticle-forming peptides. Peptide 1 when used as a self-assembling peptide, does not form a gel-like material 24 h post-assembly, irrespective of the nature of nanoparticle loaded. Transmission electron micrographs of 0.5% (w/v) Peptide 3 hydrogel with encapsulated nanoparticles consisting of Peptide 1 (FIGS. 15B-15D) and blank 0.5% (w/v) peptide 3 hydrogel (FIG. 15E).

(FIG. 16A) Shear-thin recovery ability of hydrogel composites containing 0.5% and 1% (w/v) Peptide 3 as determined via oscillatory rheology. Hydrogels were formed a day before within transwell inserts and transferred on rheometer plate just before measurement. A 10 minutes time-sweep (at frequency 6 rad/s, strain 0.2%) was followed by shear-thinning at 1000% strain for 30 s after which time the gels were allowed to recover for another 60 min by reducing the strain to 0.2%. Cumulative release of FAM-miRNA from hydrogels formed via self-assembling (FIG. 16B) Peptide 2 and Peptide 3 (0.5%, w/v, 1 µg miRNA loaded) and (FIG. 16C) Peptide 3 (0.5%, w/v, 10 µg miRNA loaded) peptides into an infinite sink (25 mM HEPES, 150 mM NaCl) at 37° C. Release was determined by measuring fluorescence of heparin-treated supernatant at each time point. (FIG. 16D) Size of nanoparticles (as determined via Dynamic Light Scattering experiments) present in release supernatant collected from Peptide 3 hydrogel composites on day 2 and 4. (FIG. 16E) Agarose gel electrophoretic mobility shift assay detects released nanoparticles on day 2 and 4 from Peptide 3 hydrogel composites. (FIG. 16F) Viability of H2052 cells treated with Peptide 3 hydrogel composites 48 h post-incubation as determined by MTT assay.

(FIG. 17A) Cumulative release of FAM-miRNA from Peptide 4 hydrogel composite into an infinite sink (25 mM HEPES, 150 mM NaCl) at 37° C. (FIG. 17B) FAM-miRNA (10 µg miRNA loaded) was released from Peptide 4 gel composites separately for 24 h and H2052 cells were treated with the release supernatant for 4 h to visualize the uptake of released FAM-miRNA. Cell nuclei were stained with Hoechst 33342. Scale bar 10 µm. (FIG. 17C) Flow cytometric histogram of H2052 cells treated with naked FAM-miRNA for 4 h indicating negligible degree of miRNA uptake.

(FIG. 18A) Monitoring body weights over 3 weeks for female SCID mice receiving hydrogel composites encapsulating cy3miRNA compared to those receiving naked cy3miRNA bolus injected subcutaneously. (FIG. 18B) Body weights of mice receiving hydrogel composites of scrambled miRNA administered via various routes. For intrathoracic, subcutaneous and intraperitoneal administrations, 100, 200 and 400 µL hydrogel composites were used, respectively.

(FIG. 19A) Quantification of release of cy3 miRNA as a function of time as determined by measuring total radiant efficiency. Radiant efficiency at each time point was normalized with respect to that on day 0 for each treatment group. Data points are in ±SD for n=3 animals for groups injected with gel composites and n=2 for animals injected with miRNA in a bolus. (FIG. 19B) Volume of the gel implants were calculated from 3D grayscale ultrasound images using Vevo LAZR Ultrasound Imaging Software at different time points. Data points are in ±SD for n=3 animals. (FIG. 19C) Hematoxylin and Eosin (H & E) staining of the histological sections collected at different time points from mice receiving subcutaneously injected hydrogel composites to monitor hydrogel degradation and immune cell infiltration. H & E images are displayed at 10× and 40× magnification.

(FIG. 20A) Abdominal region from female NOD/SCIDγ mouse bearing orthotopic H2052 xenograft in the peritoneal cavity 3 weeks after tumor cell inoculation. (FIG. 20B) Shows a control mouse for comparison that does not bear any tumor graft.

(FIG. 21B) cy3-labeled miRNA nanoparticle-hydrogel composites delivers miRNA into tumor cells when injected peritumorally in NOD/SCIDγ mice bearing subcutaneous H2373 tumor grafts. Tumors were collected 24 h post-injection and cy3 expression was monitored in fixed tumor sections using confocal microscopy. Nuclei were labeled using DAPI. Corresponding z-stacks are also shown. Scale bar 10 µm (FIG. 21C) Absence of fluorescence signal in tumor sections collected from mice injected with blank hydrogel rules out the possibility of tumor tissue autofluorescence.

FIG. 24A-24C. Peptide 1:miRNA-215 nanoparticles prepared with folded β-hairpin Peptide 1 do not affect expression of miR-215 target genes, indicating that these nanoparticles are unable to properly deliver miRNA-215 to silence the miRNA-215 responsive genes (FIG. 24A). Confocal microscopy image of live H2052 cells treated for 0.5 h (FIG. 24B) and 4 h (FIG. 24C) with nanoparticles containing FAM-miRNA and Peptide 1 in a 1:1 N/P ratio where folding of Peptide 1 is initiated on the surface of miRNA and all Peptide 1 molecule stay in a β-hairpin conformation. Co-localization of FAM-miRNA at each time point was determined for late endosome/lysosome marker lysotracker red (LysoT). Nuclei staining is shown.

SEQUENCE LISTING

Figure 1B:
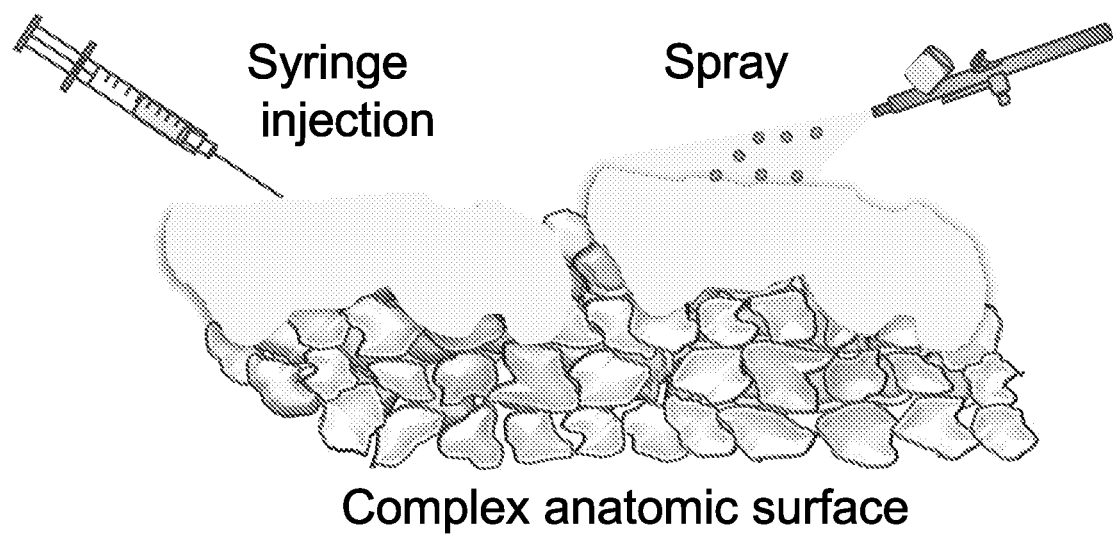

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~20 kb), which was created on Jul. 1, 2020, which is incorporated by reference herein. In the accompanying sequence listing:

DETAILED DESCRIPTION

Administration of heterologous nucleic acid molecules (such as miRNA) can alter cellular activity to provide a therapeutic effect. However, translating miRNA and other nucleic acid molecules into treatments for human disease has been hampered by the lack of clinical delivery vehicles. Described herein are embodiments of a novel nanoparticle-hydrogel composite that can deliver nucleic acid molecules (such as miRNA) to target tissue sites and facilitate transport of the nucleic acid molecule into cells. The nanoparticle-hydrogel composite includes nanoparticles comprised of an amphiphilic cationic peptide (e.g., MAX1) complexed to the nucleic acid molecule. The nanoparticles are encapsulated into a shear-thinning peptide-based hydrogel, which is comprised of a fibrillar network of self-assembled cationic amphiphilic peptides (e.g., HLT2).

Embodiments, of the disclosed nanoparticle-hydrogel composite display shear-thin/recovery mechanical properties, which allow the nanoparticle-hydrogel composite and any additional therapeutic dispersed within the hydrogel to be delivered locally to a body cavity via percutaneous or surgical access by syringe injection or sprayed to coat anatomic surfaces. For example, the nanoparticle-hydrogel composite can be applied in the space between the parietal and visceral pleura of the lung after surgical removal of mesothelioma tumor (see, e.g., FIG. 1C). After application, the nanoparticles are time-released from the hydrogel matrix to adjacent tissues and taken up by cells. Once internalized by cells, the nucleic acid molecule is released from the nanoparticle to affect cellular function. In addition to nucleic acid nanoparticles, the hydrogel can carry other biologic agents (e.g., encapsulated chemotherapeutics) permitting combinatorial therapies.

As discussed in the examples, several features of the disclosed nanoparticle hydrogel composite were unexpected and surprising. For example, it was found that if the nanoparticle was formed from miRNA complexed with the first amphiphilic cationic peptide (e.g., MAX1) in a folded β-hairpin conformation, the resulting nanoparticle poorly released functional miRNA after being internalized by cells relative to nanoparticles formed from miRNA complexed with the first amphiphilic cationic peptide (e.g., MAX1) not in folded β-hairpin conformation. This is surprising for at least two reasons. First, the MAX1 peptide has a strong propensity to adopt a β-hairpin conformation under many solution conditions. However, if complexed to miRNA in pure water, it remains unfolded. Second, although miRNA nanoparticles formed by MAX1 folded into a β-hairpin conformation entered cells as efficiently as nanoparticles formed by unfolded MAX1, the nanoparticles formed by MAX1 folded into a β-hairpin conformation had little to no effect on expression of genes targeted by the corresponding miRNA. In contrast, miRNA nanoparticles formed by unfolded MAX1 entered cells and disrupted expression of genes targeted by the corresponding miRNA in the nanoparticle.

Another surprising feature of the nanocomposite hydrogel is that delivery of functional miRNA was substantially better with hydrogels having a positively charged fibrillar network compared to hydrogels having a negatively charged fibrillar network. As shown in the Examples, if cationic peptide:miRNA nanoparticles are embedded into hydrogel formed from a negatively charged peptide network, the nanoparticles disassemble and prematurely release free naked miRNA which cannot enter cells. It is believed that when a negatively charged fibrillar hydrogel network is used to encapsulate cationic peptide:RNA nanoparticles, the cationic peptide dissociates from the miRNA and forms a tight complex with the negatively charged hydrogel network. This ejects free miRNA into solution.

Further, the hydrogel composite material remained highly localized to the anatomic site where it was deployed, there was specific and concentrated uptake of miRNA payload in cancer cells and not appreciable in other normal tissues, sustained release characteristics of the hydrogel composite established in vitro were replicated in vivo, and that the hydrogel composite was itself non-toxic to the subject (in this instance an experimental mouse model).

In an exemplified embodiment, the nanoparticle-hydrogel composite is used to treat malignant pleural mesothelioma, a complex surface cancer of the lung lining. This recalcitrant tumor is generally resistant to chemotherapy, radiation, and cannot be completely excised. Thus, there is an urgent need for improved malignant pleural mesothelioma treatment strategies. Beyond malignant pleural mesothelioma, the nanoparticle-hydrogel composite can be used to deliver nucleic acid molecule (such as miRNA) and/or other combination therapies to diverse types of surface cancers.

A. Summary of Terms

Unless otherwise noted, technical terms are used according to conventional usage. As used herein, the singular forms "a," "an," and "the," refer to both the singular as well as plural, unless the context clearly indicates otherwise. For example, the term "a peptide" includes single or plural peptides and can be considered equivalent to the phrase "at least one peptide." As used herein, the term "comprises" means "includes." Thus, "comprising a peptide" means "including a peptide" without excluding other elements. It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

About: Unless context indicated otherwise, "about" refers to plus or minus 5% of a reference value. For example, "about" 100 refers to 95 to 105.

Amphiphilic cationic β-hairpin peptide: A peptide that has a positive electrostatic charge at neutral pH and folds into a β-hairpin conformation under suitable conditions, such as when dissolved at 2.0% w/v in 50 mM Bis Tris Propane, pH 7.4, 150 mM NaCl, at 25° C. When folded into the β-hairpin conformation, one face of the hairpin is primarily hydrophobic, and the other is primarily hydrophilic. A non-limiting example of an amphiphilic cationic β-hairpin peptide is provided herein as HLT2 peptide.

Antisense nucleic acid molecule: An oligomeric compound that is at least partially complementary to the region of a target nucleic acid molecule (such as a RNA gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression.

Non-limiting examples of antisense nucleic acid molecules include antisense oligonucleotides, siRNAs, miRNAs, shRNAs and ribozymes. As such, these nucleic acid molecules can be introduced as single-stranded, double-stranded, circular, branched or hairpin nucleic acid molecules and can contain structural elements such as internal or terminal bulges or loops. Double-stranded antisense nucleic acid molecules can be two strands hybridized to form double-stranded compounds or a single strand with sufficient self complementarity to allow for hybridization and formation of a fully or partially double-stranded nucleic acid molecule.

β-hairpin conformation: A structural conformation of a peptide or protein. The β-hairpin conformation includes two β-strands linked by a β-turn to form a "hairpin"-like shape. The structure is amphiphilic; thus, one face of the hairpin is primarily hydrophobic, and the other is primarily hydrophilic. A limited number of the side chains of hydrophobic amino acids can exist on the hydrophilic face of the hairpin and vice versa, but not so many as to change the overall amphiphilicity of the folded structure. A non-limiting example of a peptide that can fold into an β-hairpin conformation is provided herein as HLT2.

Cancer: A malignant neoplasm (e.g., a tumor) that has undergone characteristic anaplasia with loss of differentiation, increased rate of growth, invasion of surrounding tissue, and is capable of metastasis. Metastatic cancer is a cancer at one or more sites in the body other than the site of origin of the original (primary) cancer from which the metastatic cancer is derived. In some examples, cancer is a condition in which expression of one or more miRNAs is altered (for example, increased or decreased) in the neoplasm, compared to normal or healthy tissue of the same tissue type.

Chemotherapeutic agent: Any chemical agent with therapeutic usefulness in the treatment of diseases characterized by abnormal cell growth. Such diseases include tumors, neoplasms, and cancer. In one embodiment, a chemotherapeutic agent is an agent of use in treating a serosal neoplasm, such as malignant pleural mesothelioma. Non-limiting examples of chemotherapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors.

Disperse: Distribute throughout a medium, such as a disclosed peptide hydrogel. In particular examples, nanoparticles composed of a miRNA complexed with an amphiphilic cationic peptide are dispersed in a peptide hydrogel and are distributed evenly throughout the peptide hydrogel. However, dispersal of the nanoparticles in a peptide hydrogel does not require absolute even distribution.

Effective amount: An amount of an agent (such as one or more miRNAs) that is sufficient to produce a desired response, such as reducing or inhibiting one or more signs or symptoms associated with a condition or disease. In some examples, an "effective amount" is an amount that treats or inhibits one or more signs or symptoms of a tumor. In some examples, an "effective amount" is a therapeutically effective amount in which the agent alone or with one or more additional therapies, induces the desired response, such as a decrease in size of a tumor in a subject, number of tumors in a subject, size or number of tumor metastases in a subject, and/or an increase in survival of a subject (such as disease-free survival, metastasis-free survival, or overall survival).

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Non-limiting examples of expression vectors include cosmids and DNA plasmids that incorporate the recombinant polynucleotide.

Isolated: An "isolated" biological component (such as a nucleic acid molecule, protein, or cell) has been substantially separated or purified away from other biological components (for example, in the cell or tissue of an organism, or the organism itself, in which the component naturally occurs, such as other chromosomal and extra-chromosomal DNA and RNA, proteins and cells). Nucleic acid molecules and proteins that have been "isolated" include those purified by standard purification methods. The term also embraces nucleic acid molecules (including miRNAs) and proteins prepared by recombinant expression in a host cell as well as chemically synthesized nucleic acid molecules and proteins.

microRNA (miRNA or miR): Single-stranded, small non-coding RNA molecules that regulate gene expression. miRNAs are generally about 16-27 nucleotides in length. miRNAs typically modulate gene expression (e.g., increase or decrease translation) by promoting cleavage of target mRNAs or by blocking translation of the cellular transcript. miRNAs are processed from primary transcripts known as pri-miRNA to short stem-loop structures called precursor (pre)-miRNA and finally to functional, mature miRNA. Mature miRNA molecules are partially complementary to one or more messenger RNA molecules, and their primary function is to down-regulate gene expression. As utilized herein, "miR nucleic acid" or "miRNA nucleic acid" refers to any of a pri-miRNA, a pre-miRNA, a miRNA duplex, or a mature miRNA.

A nomenclature scheme is established for miRNAs. For example, a miRNA name includes a three or four letter species prefix, such as "hsa" for Homo sapiens, and a numeric suffix, such as "1," resulting in a complete name of "hsa-miR-1." Mature miRNA sequences expressed from more than one hairpin precursor molecule are distinguished by "-1" and "-2" (such as hsa-miR-24-1 and hsa-miR-24-2). Related hairpin loci expressing related mature miRNA sequences have lettered suffixes (such as hsa-miR-26a and hsa-miR-26b). In some cases, mature miRNAs from both the 5' and 3' arms of the hairpin precursor are identified, which are designated "5p" or "3p", respectively (such as hsa-miR-27b-5p and hsa-miR-27b-3p).

Most known miRNA sequences are publicly available. For example, miRBase (mirbase.org) includes a searchable database of annotated miRNA sequences. miRNA sequences are also available through other databases known to one of ordinary skill in the art, including the National Center for Biotechnology Information (ncbi.nlm.nih.gov). One of ordinary skill in the art can also identify targets for specific miRNAs utilizing public databases and algorithms, for example at MicroCosm Targets (ebi.ac.uk/enright-srv/microcosm/htdocs/targets/), TargetScan (targetscan.org), and PicTar (pictar.mdc-berlin.de). Based on miRNA sequences from one organism (such as mouse), one of ordinary skill in the art can utilize the available databases to determine a corresponding miRNA from another organism (such as human).

miRNA Mimic or Mimetic: A miRNA mimetic includes a miRNA has the same sequence as the native or wild type miRNA, but has a modified backbone, a modified base, and/or a 5' or 3' end modification. In some examples a miRNA mimetic is may less susceptible to degradation or nuclease activity. A miRNA mimic is a miRNA with at least one sequence modification and having 75% or higher sequence identity to a native or wild type miRNA and that also binds to the same mRNA(s) with similar affinity as the wild type or native miRNA. The disclosed miRNAs may also be both a miRNA mimetic and a miRNA mimic, for example, a miRNA with at least one sequence modification (e.g., 75% or higher sequence identity) to a wild type miRNA, and also having a modified backbone, base, and/or end modification.

Nanoparticles: Solid colloidal particles that range in size from about 10-1000 nm. They can be made from biodegradable and biocompatible biomaterials. Nanoparticles used in the disclosed embodiments include a cationic peptide complexed with a nucleic acid molecule via electrostatic interactions that can be taken up into cells in vivo and in vitro.

Nucleic acid molecule: A deoxyribonucleotide or ribonucleotide polymer in either single or double stranded form, and unless otherwise limited, encompasses known analogues of natural nucleotides that hybridize to nucleic acids in a manner similar to naturally occurring nucleotides. A nucleic acid molecule includes both sense and anti-sense strands of RNA, cDNA, genomic DNA, and synthetic forms and mixed polymers of the above. A nucleic acid molecule is usually at least 10 bases in length, unless otherwise specified.

Peptide: A chain of amino acids, typically less than 75 amino acids in length, such as 20-50 amino acids in length. The residues in a peptide can include post-translational or secondary modifications, such as glycosylation, sulfation or phosphorylation, as well as chemical modifications. "Peptide" applies to naturally occurring amino acid polymers and non-naturally occurring amino acid polymers, including amino acid polymers in which one or more amino acid residues are non-natural amino acids. A "residue" refers to an amino acid or amino acid mimetic incorporated in a peptide by an amide bond or amide bond mimetic. A peptide has an amino terminal (N-terminal) end and a carboxy terminal (C-terminal) end.

Typically, the amino acids making up a peptide are numbered in order, starting at the amino terminus and increasing in the direction toward the carboxy terminus of the peptide. Thus, when one amino acid is said to "follow" another, that amino acid is positioned closer to the carboxy terminal end of the peptide than the preceding amino acid.

Peptide hydrogel: A colloid gel including an internal phase and a dispersion medium, in which an aqueous solution is the dispersion medium and a self-assembled network of peptides is the internal phase. The peptides in the hydrogel are self-assembled and are folded into an β-hairpin conformation in the fibrillar network that forms the internal phase of the hydrogel. The peptide hydrogels disclosed herein are made using peptides that form an β-hairpin conformation in an aqueous solution comprising 150 mM NaCl and a pH of 7.4 at 25-37° C. Thus, an aqueous solution containing 2% w/v of a disclosed peptide and 150 mM NaCl and a pH of 7.4 forms a peptide hydrogel comprising a fibrillar network of the peptide when incubated at 25-37° C. in a container. Peptide hydrogels include a sufficient elastic modulus or stiffness that allows them to maintain shape. In several embodiments, the peptide hydrogel has an elastic modulus of 40 Pascal or greater. Peptide hydrogels formed from the disclosed self-assembled peptides in an β-hairpin conformation can be characterized by shear-thin/recovery rheological properties. The hydrogel undergoes a gel-sol phase transition upon application of shear stress, and a sol-gel phase transition upon removal of the shear stress. Thus, application of shear stress converts the solid-like gel into a viscous gel capable of flow, and cessation of the shear results in gel recovery. General information concerning peptide hydrogels having shear-thin/recovery rheological properties and methods of making same is provided, for example, in Sathaye, et al. Biomacromolecules, 2014, 15(11):3891-3900; Hule et al., 2008, Faraday Discuss, 139: 251-420. In several embodiments, the peptide hydrogel can be a sterile hydrogel prepared with physiological and non-toxic dispersion medium for use to deliver therapeutics to a subject.

Polypeptide and peptide modifications: The present disclosure includes synthetic peptides, as well as derivatives (chemically functionalized polypeptide molecules obtained starting with the disclosed polypeptide sequences) and variants (homologs) of peptides described herein. The peptides disclosed herein include a sequence of amino acids that can include L- and/or D-amino acids, naturally occurring and otherwise.

Peptides can be modified by a variety of chemical techniques to produce derivatives having essentially the same activity as the unmodified polypeptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and R2 are each independently H or $C_1$-$C_{16}$ alkyl, or combined to form a heterocyclic ring, such as a 5- or 6-membered ring. Amino groups of the polypeptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the polypeptide side chains can be converted to $C_1$-$C_{16}$ alkoxy or to a $C_1$-$C_{16}$ ester using well-recognized techniques. Phenyl and phenolic rings of the polypeptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides of this disclosure to select and provide conformational constraints to the structure that result in enhanced stability. For example, a C- or N-terminal cysteine can be added to the polypeptide, so that when oxidized the polypeptide will contain a disulfide bond, generating a cyclic polypeptide. Other polypeptide cyclizing methods include the formation of thioethers and carboxyl- and amino-terminal amides and esters.

Subject: Living multi-cellular vertebrate organisms, a category that includes human and non-human mammals. In one example, a subject is a human.

Treating or preventing a disease: "Preventing" a disease refers to inhibiting the full development of a disease, for example in a person who is known to have a predisposition to a disease such as a cancer. "Treating" refers to a therapeutic intervention that ameliorates a sign or symptom of a disease or pathological condition after it has begun to develop. "Ameliorating" refers to the reduction in the number or severity of signs or symptoms of a disease, such as cancer. In several embodiments, treatment refers to a reduction in size of a tumor, a decrease in the number and/or size of metastases, or a decrease in a symptom of the tumor.

Tumor burden: The total volume, number, metastasis, or combinations thereof of tumor or tumors in a subject, or in an organ of a subject.

Under conditions sufficient for: A phrase that is used to describe any environment that permits a desired activity. In one example the desired activity is treatment of a tumor.

B. Nanoparticle-Hydrogel Composite for Nucleic Acid Delivery

Provided herein are embodiments of a nanoparticle-hydrogel composite material containing a colloidal peptide-nucleic acid molecule nanoparticle dispersed within a peptide hydrogel. The nanoparticle-hydrogel composite displays shear-thin/recovery mechanical properties, which allow the nanoparticle-hydrogel composite and any additional therapeutic dispersed within the hydrogel to be delivered locally to a body cavity, for example, via percutaneous or surgical access by syringe injection, or spray delivery to coat anatomic surfaces. After application, the nanoparticles time-release from the hydrogel matrix to adjacent tissues and are taken up by cells. Once internalized by cells, the nucleic acid molecule is released from the nanoparticle and (depending on the nucleic acid molecule) may affect cellular function.

The peptide-nucleic acid molecule nanoparticle comprises a nucleic acid molecule complexed with a first amphiphilic cationic peptide that is not in a β-hairpin conformation. The peptide hydrogel is formed from a fibrillar network of a second amphiphilic cationic peptides that is in a β-hairpin conformation.

The hydrogel can carry other biologic agents (e.g., encapsulated chemotherapeutics) permitting combinatorial therapies. A discussion of the components of the nanoparticle-hydrogel composite is provided below.

Nanoparticles

The nanoparticle encapsulated within the peptide hydrogel comprises a nucleic acid molecule complexed with a first amphiphilic cationic peptide that is not in a β-hairpin conformation.

The first amphiphilic cationic peptide is admixed with the nucleic acid molecule under conditions where the peptide is not in a β-hairpin conformation to form the complex of the nucleic acid molecule and the first amphiphilic cationic peptide. The nanoparticle component of the nanoparticle-hydrogel composite can readily be produced, for example, by mixing the first amphiphilic cationic peptide and the nucleic acid molecule in water under conditions sufficient to form the peptide-nucleic acid molecule nanoparticles. Any suitable ratio of the peptide to the nucleic acid molecule can be used that effectively forms the peptide:nucleic acid molecule nanoparticles in aqueous solution. The linear first amphiphilic cationic peptide and the nucleic acid molecule interact via electrostatic interaction between the cationic peptide and anionic nucleic acid to form the nanoparticle (see, e.g., FIG. 1A, Stage 1).

Once the nanoparticles are formed, they are mixed with the second amphiphilic cationic β-hairpin peptide under conditions sufficient for the second amphiphilic cationic β-hairpin peptide to fold into a β-hairpin conformation and form a peptide hydrogel that encapsulated the nanoparticles (such as 50 mM Bis Tris Propane, pH 7.4, 150 mM NaCl, at 25° C.). Under these conditions and following gelation, the first peptide-nucleic acid molecule complex is a colloidal nanoparticle dispersed within the peptide hydrogel.

When the nanoparticle is released from the peptide hydrogel and internalized by cells, the first amphiphilic cationic peptide disassociates from the nucleic acid molecule, allowing the nucleic acid molecule to mediate its biological action. It is believed that having the first amphiphilic cationic peptide not folded into a β-hairpin conformation promotes dissociation of the peptide from the nucleic acid molecule after the nanoparticle is internalized by cells.

The electrostatic charge of the first amphiphilic cationic peptide is equal to or more positive than the electrostatic charge of the second amphiphilic cationic peptide (used to form the peptide hydrogel) at neutral pH. In some embodiments, the electrostatic charge of the first amphiphilic cationic peptide is from +7 to +10 (such as +7, +8, +9, or +10) and the electrostatic charge of the second amphiphilic cationic peptide is from +3 to +8 (such as +3, +4, +5, +6, +7, or +8) at neutral pH. In some embodiments, the electrostatic charge of the first amphiphilic cationic peptide is +9 and the electrostatic charge of the second amphiphilic cationic peptide is +5 at neutral pH.

In some embodiments, the first amphiphilic cationic peptide comprises or consists of an amino acid sequence set forth as:

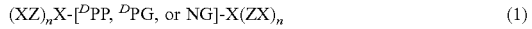

$$(XZ)_n\text{-}X\text{-}[^{D}PP, \,^{D}PG, \text{ or } NG]\text{-}X(ZX)_n \quad (1)$$

wherein each X is individually selected from any one of F, I, L, M, T, V, W, and Y; each Z is individually selected from any one of H, K, Ornithine, and R; n is from 3 to 5 (such as 3, 4, or 5); and the peptide has a net formal charge of from +7 to +10 (such as +7, +8, +9, or +10) at neutral pH. The C-terminus of the peptide is not carboxylate and comprises a peptide modification having a neutral or positive charge (for example, the C-terminus can be amidated). The peptide folds into an β-hairpin conformation when dissolved at 2.0% w/v in 50 mM Bis Tris Propane, pH 7.4, 150 mM NaCl, at 25° C., but does not fold into the β-hairpin conformation when dissolved in water.

In some embodiments of peptide (1), the first amphiphilic cationic peptide comprises or consists of an amino acid sequence set forth as:

$$(XZ)_n X^{D}PPX(ZX)_n; \quad (1a)$$

wherein each X is individually selected from any one of F, I, L, M, T, V, W, and Y; each Z is individually selected from any one of H, K, Ornithine, and R; n is from 3 to 5 (such as 3, 4, or 5); and the peptide has a net formal charge of from +7 to +10 (such as +7, +8, +9, or +10) at neutral pH. The C-terminus of the peptide is not carboxylate and comprises a peptide modification having a neutral or positive charge (for example, the C-terminus can be amidated). The peptide folds into an β-hairpin conformation when dissolved at 2.0% w/v in 50 mM Bis Tris Propane, pH 7.4, 150 mM NaCl, at 25° C., but does not fold into the β-hairpin conformation when dissolved in water.

In some embodiments of peptide (1), the first amphiphilic cationic peptide comprises or consists of an amino acid sequence set forth as:

(XZ)$_n$X$^D$PGX(ZX)$_n$; or  (1b)

wherein each X is individually selected from any one of F, I, L, M, T, V, W, and Y; each Z is individually selected from any one of H, K, Ornithine, and R; n is from 3 to 5 (such as 3, 4, or 5); and the peptide has a net formal charge of from +7 to +10 (such as +7, +8, +9, or +10) at neutral pH. The C-terminus of the peptide is not carboxylate and comprises a peptide modification having a neutral or positive charge (for example, the C-terminus can be amidated). The peptide folds into an β-hairpin conformation when dissolved at 2.0% w/v in 50 mM Bis Tris Propane, pH 7.4, 150 mM NaCl, at 25° C., but does not fold into the β-hairpin conformation when dissolved in water.

In some embodiments of peptide (1), the first amphiphilic cationic peptide comprises or consists of an amino acid sequence set forth as:

(SEQ ID NO: 1)
(1c)  (XZ)$_n$ X NGX(ZX)$_n$;

wherein each X is individually selected from any one of F, I, L, M, T, V, W, and Y; each Z is individually selected from any one of H, K, Ornithine, and R; n is from 3 to 5 (such as 3, 4, or 5); and the peptide has a net formal charge of from +7 to +10 (such as +7, +8, +9, or +10) at neutral pH. The C-terminus of the peptide is not carboxylate and comprises a peptide modification having a neutral or positive charge (for example, the C-terminus can be amidated). The peptide folds into an β-hairpin conformation when dissolved at 2.0% w/v in 50 mM Bis Tris Propane, pH 7.4, 150 mM NaCl, at 25° C., but does not fold into the β-hairpin conformation when dissolved in water.

In some embodiments of peptide (1), the first amphiphilic cationic peptide comprises or consists of an amino acid sequence set forth as:

(SEQ ID NO: 2)
(1d)  VKVKVKVKV$^D$PPTKVKVKVKV (1e)  VKVKVKVKV$^D$PGTKVKVKVKV (1f)  VKVKVKVKV NGTKVKVKVKV

The C-terminus of the peptide is not carboxylate and comprises a peptide modification having a neutral or positive charge (for example, the C-terminus can be amidated). The peptide folds into an β-hairpin conformation when dissolved at 2.0% w/v in 50 mM Bis Tris Propane, pH 7.4, 150 mM NaCl, at 25° C., but does not fold into the β-hairpin conformation when dissolved in water.

In some embodiments, the N-terminus of the first amphiphilic cationic peptide is acetylated. In some embodiments, the C-terminus of the first amphiphilic cationic peptide is amidated.

In several embodiments, the first amphiphilic cationic peptide does not contain any negatively charged amino acids, which are believed to disfavor binding to the nucleic acid molecule of the nanoparticle.

Nucleic Acid Molecule Included in the Nanoparticle

The nucleic acid molecule in the nanoparticle can be any appropriate nucleic acid molecule for delivery to cells in a nanoparticle context. Non-limiting examples include miRNA, plasmid DNA, siRNA, shRNA, long non-coding RNA.

In a non-limiting embodiment, the nucleic acid molecule is a plasmid DNA molecule encoding a therapeutic protein (e.g., a protein capable of inducing a desired therapeutic or prophylactic effect when administered to a subject). In some embodiments, the therapeutic protein is a vaccine antigen.

In some embodiments the nucleic acid molecule is an antisense nucleic acid molecule, such as a siRNA, shRNA, or antisense miRNA, or a mimic and/or mimetic thereof.

In a preferred embodiment, the nucleic acid molecule is a miRNA, or a or a mimic and/or mimetic thereof. The miRNA or mimic and/or mimetic thereof can be utilized, for example, in methods for treating cancer.

miRNAs are small non-coding RNA molecules that regulate gene expression. Mature miRNAs are generally about 17-25 nucleotides in length. miRNAs typically modulate gene expression (e.g., increase or decrease translation) by promoting cleavage of target mRNAs or by blocking translation of the cellular transcript. miRNAs are processed from primary transcripts known as "pri-miRNA" to short stem-loop structures called "precursor (pre)-miRNA." The pre-miRNA is processed to a miRNA duplex and finally to functional, mature single-stranded miRNA. During processing of the miRNA duplex, one strand (referred to as the "passenger" strand) is degraded, while the other strand (the "guide" strand) is the mature miRNA molecule. Mature miRNA molecules are partially complementary to one or more messenger RNA molecules, and their primary function is to down-regulate gene expression. As disclosed herein, a miRNA nucleic acid includes precursor miRNAs, as well processed or mature miRNA nucleic acids. For example, a miRNA nucleic acid may be a pri-miRNA, a pre-miRNA, a miRNA duplex, or a mature miRNA nucleic acid.

miRNA sequences are publicly available. One of ordinary skill in the art can identify miRNA precursors, as well as processed or mature miRNAs, for example, utilizing publicly available databases. For example, miRBase (mirbase.org) includes a searchable database of annotated miRNA sequences. miRNA sequences are also available through other databases known to one of ordinary skill in the art, including the National Center for Biotechnology Information (ncbi.nlm.nih.gov). One of ordinary skill in the art can also identify targets for specific miRNAs utilizing public databases and algorithms, for example at MicroCosm Targets (ebi.ac.uk/enright-srv/microcosm/htdocs/targets/), TargetScan (targetscan.org), and PicTar (pictar.mdc-berlin.de). Based on miRNA sequences from one organism (such as mouse), one of ordinary skill in the art can utilize the available databases to determine a corresponding miRNA from another organism (such as human).

In some examples, miRNA functions by activating cleavage or destabilization of a target mRNA or non-coding RNA, which can be detected by RT-PCR, is situ hybridization, FRET, northern blot, or sequencing. It may also function by inhibiting translation of a target mRNA into a protein, which may be detected by Western blot, immune blotting, florescence polarization assay, enzyme activity assay, FRET, immunofluorescence, immunohistochemistry, ELISA, or mass spectrometry. The resulting change in expression of targeted mRNAs or non-coding RNA may result in repression of a number of cancer relevant phenotypes including cell proliferation, resisting cell death, pro-inflammatory processes, increased migration and invasion, angiogenesis, evasion of immune destruction, replicative immortality, decreased genome stability, deregulated cellular energetics, and/or deregulation of epigenetic processes which effect tumor growth and progression.

In some examples, the miRNA nucleic acids of use in the nanoparticle-hydrogel composite and methods disclosed herein include the mature miRNAs listed in Table 1. In other examples, the miRNA nucleic acids include those with at least 75% sequence identity to those listed in Table 1 (e.g., miRNA mimics), as long as such modified miRNAs retain one or more functions of the unmodified miRNA. For example, the miRNA nucleic acid includes or consists of a nucleic acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% 99%, or 100% identical to the nucleic acid sequence of one of the miRNAs listed in Table 1. Additional miRNA nucleic acids of use in the disclosed compositions and methods include a miRNA including guide and/or passenger strands, as long as such modified miRNAs retain one or more functions of the unmodified miRNA. In some examples, the miRNAs with at least 75% sequence identity to those shown in Table 1, include at least one (such as 1, 2, 3, 4, 5, 6, 7, 8, 9, 10, or more) non-naturally occurring nucleotide.

TABLE 1

Exemplary mature huma miRNAs for use in the disclosed nanoparticle-hydrogel composite.

| Huma miRNA | Sequence | SEQ ID NO |
|---|---|---|
| hsa-miR-1 | ACAUACUUCUUUAUAUGCCCAU | 3 |
| hsa-miR-7 | UGGAAGACUAGUGAUUUUGUUGU | 4 |
| hsa-miR-10a | UACCCUGUAGAUCCGAAUUUGUG | 5 |
| hsa-miR-15 | UAGCAGCACAUAAUGGUUUGUG | 6 |
| hsa-miR-16 | UAGCAGCACGUAAAUAUUGGCG | 7 |
| hsa-miR-23a-3p | AUCACAUUGCCAGGGAUUUCC | 8 |
| hsa-miR-24-1 | UGCCUACUGAGCUGAUAUCAGU | 9 |
| hsa-miR-24-2-5p | UGCCUACUGAGCUGAAACACAG | 10 |
| hsa-miR-26a | UUCAAGUAAUCCAGGAUAGGCU | 11 |
| hsa-miR-26b | UUCAAGUAAUUCAGGAUAGGU | 12 |
| hsa-miR-27a-5p | AGGGCUUAGCUGCUUGUGAGCA | 13 |
| hsa-miR-27b-5p | AGAGCUUAGCUGAUUGGUGAAC | 14 |
| hsa-miR-27b-3p | UUCACAGUGGCUAAGUUCUGC | 15 |
| hsa-miR-29a | ACUGAUUUCUUUUGGUGUUCAG | 16 |
| hsa-miR-29b | GCUGGUUUCAUAUGGUGGUUUAGA | 17 |
| hsa-miR-29c | UGACCGAUUUCUCCUGGUGUUC | 18 |
| hsa-miR-30b-5p | UGUAAACAUCCUACACUCAGCU | 19 |
| hsa-miR-30c-1 | UGUAAACAUCCUACACUCUCAGC | 20 |
| hsa-miR-33a | GUGCAUUGUAGUUGCAUUGCA | 21 |
| hsa-miR-34a | UGGCAGUGUCUUAGCUGGUUGU | 22 |

TABLE 1-continued

Exemplary mature huma miRNAs for use in the disclosed nanoparticle-hydrogel composite.

| Huma miRNA | Sequence | SEQ ID NO |
|---|---|---|
| hsa-miR-95 | UCAAUAAAUGUCUGUUGAAUU | 23 |
| hsa-miR-96 | UUUGGCACUAGCACAUUUUUGCU | 24 |
| hsa-miR-100 | AACCCGUAGAUCCGAACUUGUG | 25 |
| hsa-miR-125a | UCCCUGAGACCCUUUAACCUGUGA | 26 |
| hsa-miR-127 | CUGAAGCUCAGAGGGCUCUGAU | 27 |
| hsa-miR-130a | UUCACAUUGUGCUACUGUCUGC | 28 |
| hsa-miR-130b | ACUCUUUCCCUGUUGCACUAC | 29 |
| hsa-miR-132-3p | UAACAGUCUACAGCCAUGGUCG | 30 |
| hsa-miR-133b | UUUGGUCCCCUUCAACCAGCUA | 31 |
| hsa-miR-134 | UGUGACUGGUUGACCAGAGGGG | 32 |
| hsa-miR-135a-1 | UAUGGCUUUUUAUUCCUAUGUGA | 33 |
| hsa-miR-136 | ACUCCAUUUGUUUUGAUGAUGGA | 34 |
| hsa-miR-139 | UCUACAGUGCACGUGUCUCCAGU | 35 |
| hsa-miR-143 | GGUGCAGUGCUGCAUCUCUGGU | 36 |
| hsa-miR-145 | GUCCAGUUUUCCCAGGAAUCCCU | 37 |
| hsa-miR-148a | AAAGUUCUGAGACACUCCGACU | 38 |
| hsa-miR-149 | UCUGGCUCCGUGUCUUCACUCCC | 39 |
| hsa-miR-181c | AACAUUCAACCUGCGGUGAGU | 40 |
| hsa-miR-181d | AACAUUCAUUGUUGUCGGUGGGU | 41 |
| hsa-miR-182 | UUUGGCAAUGGUAGAACUCACACU | 42 |
| hsa-mir-183 | UAUGGCACUGGUAGAAUUCACU | 43 |
| hsa-miR-190 | UGAUAUGUUUGAUAUAUUAGGU | 44 |
| hsa-miR-190b | UGAUAUGUUUGAUAUUGGGUU | 45 |
| hsa-miR-192 | CUGACCUAUGAAUUGACAGCC | 46 |
| hsa-miR-195 | UAGCAGCACAGAAAUAUUGGC | 47 |
| hsa-miR-194 | UGUAACAGCAACUCCAUGUGGA | 48 |
| hsa-miR-200 | CAUCUUACCGGACAGUGCUGGA | 49 |
| hsa-miR-206 | UGGAAUGUAAGGAAGUGUGUGG | 50 |
| hsa-miR-212 | ACCUUGGCUCUAGACUGCUUACU | 51 |
| hsa-miR-215 | AUGACCUAUGAAUUGACAGAC | 52 |
| hsa-miR-221 | ACCUGGCAUACAAUGUAGAUUU | 53 |
| hsa-miR-222-3p | AGCUACAUCUGGCUACUGGGU | 54 |
| hsa-miR-320d-1 | AAAAGCUGGGUUGAGAGGA | 55 |
| hsa-miR-370 | CAGGUCACGUCUCUGCAGUUAC | 56 |
| hsa-miR-375 | UUUGUUCGUUCGGCUCGCGUGA | 57 |
| hsa-miR-342 | AGGGGUGCUAUCUGUGAUUGA | 58 |
| hsa-miR-376a-1 | GUAGAUUCUCCUUCUAUGAGUA | 59 |
| hsa-miR-376b | CGUGGAUAUUCCUUCUAUGUUU | 60 |

TABLE 1-continued

Exemplary mature huma miRNAs for use in the
disclosed nanoparticle-hydrogel composite.

| Huma miRNA | Sequence | SEQ ID NO |
|---|---|---|
| hsa-miR-491 | AGUGGGGAACCCUUCCAUGAGG | 61 |
| hsa-miR-497 | CAGCAGCACACUGUGGUUUGU | 62 |
| hsa-miR-502 | AUCCUUGCUAUCUGGGUGCUA | 63 |
| hsa-miR-506 | UAUUCAGGAAGGUGUUACUUAA | 64 |
| hsa-miR-509-1 | UACUGCAGACAGUGGCAAUCA | 65 |
| hsa-miR-548 | CAAAACUGGCAAUUACUUUUGC | 66 |
| hsa-miR-643 | ACUUGUAUGCUAGCUCAGGUAG | 67 |
| hsa-miR-653 | GUGUUGAAACAAUCUCUACUG | 68 |
| hsa-miR-664 | ACUGGCUAGGGAAAAUGAUUGGAU | 69 |
| hsa-miR-668 | UGCGCCUCGGGUGAGCAUG | 70 |
| hsa-miR-676 | UCUUCAACCUCAGGACUUGCA | 71 |
| hsa-miR-939 | UGGGGAGCUGAGGCUCUGGGGGUG | 72 |
| hsa-miR-1245 | AAGUGAUCUAAAGGCCUACAU | 73 |
| hsa-miR-1287 | UGCUGGAUCAGUGGUUCGAGUC | 74 |
| hsa-miR-1293 | UGGGUGGUCUGGAGAUUUGUGC | 75 |
| hsa-miR-1294 | UGUGAGGUUGGCAUUGUUGUCU | 76 |
| hsa-miR-1538 | CGGCCCGGGCUGCUGCUGUUCCU | 77 |
| hsa-miR-2114 | UAGUCCCUUCCUUGAAGCGGUC | 78 |
| hsa-miR-3145 | AACUCCAAACACUCAAAACUCA | 79 |
| hsa-miR-3610 | GAAUCGGAAAGGAGGCGCCG | 80 |
| hsa-miR-3677 | CAGUGGCCAGAGCCCUGCAGUG | 81 |
| miRNA mimics | | |
| hsa-let-7c-5p | UGAGGUAGUAGGUUGUAUGGUU | 85 |
| hsa-miR-590-3p | UAAUUUUAUGUAUAAGCUAGU | 86 |
| hsa-miR-4472-1 | GGUGGGGGUGUUGUUUU | 87 |
| hsa-miR-8078 | GGUCUAGGCCCGGUGAGAGACUC | 88 |
| hsa-miR-4675 | GGGGCUGUGAUUGACCAGCAGG | 89 |
| AntagomiR/miRNA inhibitors | | |
| hsa-mir-155 | UUAAUGCUAAUCGUGAUAGGGGUU | 90 |
| hsa-mir-196b | UAGGUAGUUUCCUGUUGUUGGG | 91 |
| hsa-mir-4524a | AUAGCAGCAUGAACCUGUCUCA | 92 |
| hsa-mir-4524b | AUAGCAGCAUAAGCCUGUCUC | 93 |

In some embodiments, the nucleic acid molecule included in the nanoparticle-hydrogel composite is a miRNA, or a mimic and/or mimetic thereof, selected from any one of the mature miRNAs listed in Table 1, or a mimic and/or mimetic thereof. In some embodiments, the nanoparticle-hydrogel composite comprises a mixture of different nanoparticles comprising two or more (such as 2, 3, 4, 5, 6, 7, 8, 9, or 10) miRNAs, or a mimic and/or mimetic thereof, selected from the mature miRNAs listed in Table 1, or a mimic and/or mimetic thereof.

In a preferred embodiment, the nucleic acid molecule included in the nanoparticle-hydrogel composite is a miRNA selected from any one of hsa-miR-1, hsa-miR-24-1, hsa-miR-26a, hsa-miR-26b, hsa-miR-30b, hsa-miR-130a, hsa-miR-134, hsa-miR-145, hsa-miR-148a, hsa-miR-149, hsa-miR-192, hsa-miR-194, hsa-miR-206, hsa-miR-215, hsa-miR-342, and hsa-miR-370, or a mimic and/or mimetic thereof. In some embodiments, the nanoparticle-hydrogel composite comprises a mixture of different nanoparticles comprising two or more (such as 2, 3, 4, 5, 6, 7, 8, 9, or 10) miRNAs, or a mimic and/or mimetic thereof, selected from hsa-miR-1, hsa-miR-24-1, hsa-miR-26a, hsa-miR-26b, hsa-miR-30b, hsa-miR-130a, hsa-miR-134, hsa-miR-145, hsa-miR-148a, hsa-miR-149, hsa-miR-192, hsa-miR-194, hsa-miR-206, hsa-miR-215, hsa-miR-342, and hsa-miR-370, or a mimic and/or mimetic thereof.

In additional examples, the miRNA nucleic acid is slightly longer or shorter than the nucleotide sequence of any one of the miRNA nucleic acids disclosed herein, as long as the miRNA nucleic acid retains a function of the particular miRNA, such as hybridization to a miRNA target sequence or formation of a miRNA duplex. For example, a miRNA nucleic acid can include a few nucleotide deletions or additions at the 5'- or 3'-end of the nucleotide sequence of a miRNA described herein, such as addition or deletion of 1, 2, 3, 4, or more nucleotides from the 5'- or 3'-end, or combinations thereof (such as a deletion from one end and an addition to the other end). In particular examples, modified miRNAs described herein include addition of one or more nucleotides at the 3' end, such as addition of one or more nucleotides (for example, 1, 2, 3, or more nucleotides) at the 3' end of a miRNA passenger strand.

Also provided by the present disclosure are miRNAs that include variations to a disclosed miRNA sequence, as long as such modified miRNAs retain one or more functions of the unmodified miRNA. In some examples, the modifications provide increased stability of a guide strand-passenger strand duplex. In some examples, the modifications include substitutions at one or more nucleotides (such as 1, 2, 3, 4, 5, or more nucleotides) in a miRNA.

Also provided are miRNA mimetics, such as miRNA nucleic acids that include one or more modified nucleotides or nucleic acid analogs. In some embodiments, the isolated miRNA includes at least one nucleobase modification, for example to increase nuclease resistance, enhance half-life and/or improve efficacy. Nucleobase modifications suitable for application to miRNAs are known in the art (see, for example, U.S. Patent Application Publication Nos. 2010/0298407; 2007/0213292; 2006/0287260; 2006/0035254; 2006/0008822; and 2005/0288244).

In some examples (for example, to increase nuclease resistance and/or binding affinity to a target nucleic acid molecule), a miRNA of the disclosure includes 2'-O-methyl, 2'-fluorine, 2'-O-methoxyethyl, 2'-0-aminopropyl, 2'-amino sugar modifications and/or phosphorothioate linkages. Inclusion of locked nucleic acids (LNA), ethylene nucleic acids (ENA) (e.g., 2'-4'-ethylene-bridged nucleic acids) and certain nucleobase modifications can also increase binding affinity to the target. The inclusion of pyranose sugars in the oligonucleotide backbone can also decrease endonucleolytic cleavage. Additional modifications include morpholinos, peptide nucleic acids (PNA), unlocked nucleic acids (UNA), α-L-LNA, 4'-C-hydroxymethyl-DNA, 2'-N-adamantylmethylcarbonyl-2'-amino-LNA, 2'-N-pyren-1-ylmethyl-2'- amino-LNA, E2'-aminoethyl, 2'-guanidinoethyl, 2'-cyanoethyl, 2'-aminopropyl, oxetane-LNA, 2',4'-carbocyclic-LNA-locked nucleic acid, 2',4'-carbocyclic-ENA-locked nucleic acid, 2'-deoxy-2'-N,4'-C-ethylene-LNA, altritol nucleic acid, hexitol nucleic acid, 2'-aminoethoxymethyl, and 2'-aminopropoxymethyl.

Additional miRNA mimetics include miRNAs with modified backbones or non-natural internucleoside linkages. Oligomers having modified backbones include those that retain a phosphorus atom in the backbone and those that do not have a phosphorus atom in the backbone. Modified oligonucleotides that do not have a phosphorus atom in their internucleoside backbone are generally referred to in the art as nucleobase oligomers. Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriesters, and boranophosphates. Various salts, mixed salts and free acid forms are also included.

miRNAs having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other examples, the modified miRNAs (e.g., miRNA mimetics) include one or more substituted sugar moieties. Such modifications include 2'-O-methyl, 2'-methoxyethoxy, 2'-dimethylaminooxyethoxy, 2'-aminopropoxy, and 2'-fluoro modifications. Modifications may also be made at other positions on an oligonucleotide or other nucleobase oligomer, particularly the 3' position of the sugar on the 3' terminal nucleotide. Nucleobase oligomers may also have sugar mimetics such as cyclobutyl moieties in place of the pentofuranosyl sugar.

In further examples, a modified miRNA (e.g., a miRNA mimetic) includes a modification at the 5' or 3' end. Such modifications include a primary amino group (for example, with a carbon spacer, such as amino-C3, amino-C6, or amino-C12) at the 5' end of the miRNA. Additional end modifications include UNAs, methylphosphonate, phosphithorate, an inverted base, or an N-methyl-G cap.

In other embodiments, the miRNA includes two or more modifications, such as two or more modifications selected from a base substitution, a modification at an internucleoside linkage, a modified sugar, or a modification at the 5' and/or 3' end. For duplex miRNA molecules, the modification(s) may be present on the guide strand, the passenger strand, or both.

In some examples, the modified (e.g., mimic or mimetic) miRNA nucleic acids disclosed herein include a 5' end amino modification, such as a 5'-amino C6 modification (such as a 5'-amino C6 modified passenger strand). In other examples, the modified (e.g., mimic or mimetic) miRNA nucleic acid includes one or more nucleotides (such as 1, 2, 3, 4, 5, 6, 7, 8, or more nucleotides) with a 2' modification (such as 2'-O-Me). The 2' modified nucleotides may be internal to the miRNA (none of the modifications are on the 5' or 3' end nucleotide) or may include the 5' and/or 3' end nucleotides. In some examples, a miRNA guide strand includes one or more nucleotides (such as 3-10, 4-9, or 5-8 nucleotides) having a 2' modification. In specific examples, a guide strand includes 2' modifications on one or more internal nucleotides, and in some examples, not on a 5' or 3' end nucleotide. In other examples, a miRNA passenger stand includes one or more nucleotides (such as 3-10, 4-8, or 5-7 nucleotides) having a 2' modification. In specific examples, a passenger strand includes 2' modifications on a 5' or 3' end nucleotide, but may also include 2' modification of one or more internal nucleotides.

In some embodiments, the disclosed miRNA nucleic acids or modified (e.g., mimetic or mimic) miRNA nucleic acids are associated with a detectable label. In some examples, the miRNA nucleic acid is conjugated to a fluorescent label (such as fluorescein isothiocyanate, coumarin, Cy3, Cy5, Cy7, or Alexa Fluor® dyes), a hapten (such as digoxigenin or Myc), or a radioactive label. In other embodiments, the miRNA nucleic acid is associated with a peptide or protein (for example, to facilitate targeted delivery), such as tat, MACV GP1, folate receptor, penetratin, mesothelin, or epidermal growth factor receptor. One of skill in the art can select additional detectable labels or peptides depending on the particular circumstances.

In some embodiments, the nucleic acid molecule included in the nanoparticle is a plasmid DNA molecule encoding one or more of the disclosed miRNA nucleic acids or a mimic or mimetic thereof. The miRNA nucleic acid or a mimic or mimetic thereof encoded by plasmid DNA molecule can be operably linked to any suitable promoter for expression. Suitable promoters for expressing RNA from a plasmid include, for example, the U6 or H1 RNA pol III promoter sequences, a cytomegalovirus promoter, an SV40 promoter or metallothionein promoter. Selection of other suitable promoters is within the skill in the art. The recombinant plasmids can also comprise inducible or regulatable promoters for expression of the miRNA gene products. In one non-limiting embodiment, the miRNA nucleic acid is expressed as an RNA precursor molecule from a plasmid, and the precursor molecule is processed into a functional or mature miRNA within the target cell. Selection of plasmids suitable for expressing the miRNAs, methods for inserting nucleic acid sequences into the plasmid to express the gene products, and methods of delivering the recombinant plasmid to the cells of interest are within the skill in the art (see, for example, Zeng et al., *Mol. Cell* 9:1327-1333, 2002; Tuschl, *Nat. Biotechnol.*, 20:446-448, 2002; Brummelkarnp et al., *Science* 296:550-553, 2002; Miyagishi et al., *Nat. Biotechnol.* 20:497-500, 2002; Paddison et al., *Genes Dev.* 16:948-958, 2002; Lee et al., *Nat. Biotechnol.* 20:500-505, 2002; and Paul et al., *Nat. Biotechnol.* 20:505-508, 2002).

Peptide Hydrogel

The peptide hydrogel component of the nanoparticle-hydrogel composite material is formed from a fibrillar network of the second amphiphilic cationic peptide that is in a β-hairpin conformation.

The β-strand regions of the hairpin contain alternating sequences of hydrophobic (e.g., valine) and hydrophilic (charged) residues (e.g., lysine) such that in the folded state, one face (e.g., the valine-rich face) of the peptide is hydrophobic and the opposing face (e.g., the lysine rich face) is lined with positively charged side chains and is hydrophilic.

This amphiphilic arrangement facilitates inter-molecular peptide interactions, and the fibril arrangement necessary for hydrogel formation.

Self-assembly is facilitated facially by hydrophobic association of the hydrophobic faces of folded hairpins and laterally via H-bond formation and hydrophobic van der Waals contacts between neighboring hairpins. Detailed knowledge of these parameters allows control the self-assembly process and thus the ultimate hydrogel material properties. For example, under folding conditions peptides may adopt a desired secondary structure (e.g., may adopt an amphiphilic β-hairpin structure where one face of each β-strand in the hairpin is lined with hydrophobic residues and the other face is lined with hydrophilic residues). For example, intramolecular folding is dictated by the alleviation of charge density on the hydrophilic face upon folding, the formation of intramolecular hydrophobic van der Waals interactions, the formation of intramolecular hydrogen bonds between β-strands within the hairpin, and the turn propensity of the β-turn sequence included in the peptide.

Thus, peptides for use in the hydrogel component of the nanoparticle-hydrogel composite can be constructed to have desired characteristics by varying one or more of at least the following parameters: 1) electrostatics, for example, by varying the charge within the peptide intramolecular folding and self-assembly rates can be varied; 2) van der Waals interactions, for example, constructing peptides having varying a) lateral and facial intermolecular hydrophobic interactions and/or b) intramolecular hydrophobic interactions, allows varying the folding and self-assembly of the peptides as well as the material properties of the hydrogel; 3) hydrogen bonding, for example peptides may be constructed with varying a) intramolecular and/or b) intermolecular hydrogen bond formation to vary the folding, self-assembly and final material properties; and 4) turn sequence, for example, the turn region of peptides of the invention may be designed to control folding and thus trigger self-assembly.

In several embodiments, the peptide includes high β-sheet propensity residues flanking an intermittent four residue turn sequence. Polar and apolar residues may be arranged sequentially in the strand regions to afford amphiphilic surfaces when the peptide is folded in a β-hairpin conformation. For the four residue turn sequence, the peptide typically includes four residues (termed i, i+1, i+2, and i+3) that form a type II' β-turn. In the disclosed MAX1 peptide, these four residues are V$^D$PPT, and the type II' β-turn is defined by the dihedral angles (Phi and Psi) adopted by the $^D$PP portion of the turn sequence, where "$^D$" denotes D-stereochemistry of the first proline residue. The preferred Phi and Psi dihedral angles (degrees) that define a type II' turn are: residue i+1 (60,–120); residue i+2 (–80,0). However, these values can vary by +/–20 degrees and the peptide can still form the appropriate β-turn structure.

In one particular embodiment, HLT2, a 20-residue peptide is composed of high β-sheet propensity valine, glutamate, and serine residues flanking an intermittent tetrapeptide -V$^D$PPT-designed to adopt type-II' β-turn structure. In addition to incorporating local design elements to stabilize hairpin structure, nonlocal effects were also considered by arranging the polar and apolar residues flanking the β-turn in an alternating fashion to favor β-hairpin formation in the self-assembled state. In addition, a β-branched residue was placed at the i-position of the turn to enforce a trans prolyl amide bond geometry at the i+1 position. This design element ensures that under folding conditions, intramolecular folding of monomeric hairpins is favored prior to self-assembly. A cis prolyl bond, which is designed against, could result in the presentation of individual β-strands within each monomer in an extended conformation. Peptides capable of adopting both cis and trans conformers could undergo indiscriminant self-association of extended and correctly folded monomers and may be actively designed against.

In some embodiments, the second amphiphilic cationic peptide comprises or consists of an amino acid sequence set forth as:

$$(XZ)_nX\text{-}[^DPP, {}^DPG, \text{ or } NG]\text{-}X(ZX)_n \tag{2}$$

wherein each X is individually selected from any one of F, I, L, M, T, V, W, and Y; each Z is individually selected from any amino acid; n is from 3 to 5 (such as 3, 4, or 5); and the peptide has a net formal charge of from +3 to +8 (such as +3, +4, +5, +6, +7, or +8) at neutral pH. The peptide folds into an β-hairpin conformation when dissolved at 2.0% w/v in 50 mM Bis Tris Propane, pH 7.4, 150 mM NaCl, at 25° C.

In some embodiments of peptide (2), the second amphiphilic cationic peptide comprises or consists of an amino acid sequence set forth as:

$$(XZ)_nX^DPPX(ZX)_n \tag{2a}$$

wherein each X is individually selected from any one of F, I, L, M, T, V, W, and Y; each Z is individually selected from any amino acid; n is from 3 to 5 (such as 3, 4, or 5); and the peptide has a net formal charge of from +3 to +8 (such as +3, +4, +5, +6, +7, or +8) at neutral pH. The peptide folds into an β-hairpin conformation when dissolved at 2.0% w/v in 50 mM Bis Tris Propane, pH 7.4, 150 mM NaCl, at 25° C.

In some embodiments of peptide (2), the second amphiphilic cationic peptide comprises or consists of an amino acid sequence set forth as:

$$(XZ)_nX^DPGX(ZX)_n \tag{2b}$$

wherein each X is individually selected from any one of F, I, L, M, T, V, W, and Y; each Z is individually selected from any amino acid; n is from 3 to 5 (such as 3, 4, or 5); and the peptide has a net formal charge of from +3 to +8 (such as +3, +4, +5, +6, +7, or +8) at neutral pH. The peptide folds into an β-hairpin conformation when dissolved at 2.0% w/v in 50 mM Bis Tris Propane, pH 7.4, 150 mM NaCl, at 25° C.

In some embodiments of peptide (2), the second amphiphilic cationic peptide comprises or consists of an amino acid sequence set forth as:

(SEQ ID NO: 94)
(2c)  (XZ)$_n$ X NGX(ZX)$_n$ wherein each X is individually selected from any one of F, I, L, M, T, V, W, and Y; each Z is individually selected from any amino acid; n is from 3 to 5 (such as 3, 4, or 5); and the peptide has a net formal charge of from +3 to +8 (such as +3, +4, +5, +6, +7, or +8) at neutral pH. The peptide folds into an β-hairpin conformation when dissolved at 2.0% w/v in 50 mM Bis Tris Propane, pH 7.4, 150 mM NaCl, at 25° C.

In some embodiments of peptide (2), the second amphiphilic cationic peptide comprises or consists of an amino acid sequence set forth as:

(SEQ ID NO: 82)
(2d)  VLTKVKTKV$^D$PPTKVEVKVLV (2e)  VLTKVKTKV$^D$PGTKVEVKVLV (2f)  VLTKVKTKV NGTKVEVKVLV

The peptide folds into an β-hairpin conformation when dissolved at 2.0% w/v in 50 mM Bis Tris Propane, pH 7.4, 150 mM NaCl, at 25° C.

In some embodiments, the N-terminus of the second amphiphilic cationic peptide is acetylated. In some embodiments, the C-terminus of the second amphiphilic cationic peptide is amidated.

The second amphiphilic cationic peptide can fold into an β-hairpin conformation comprising a β-turn, two β-strands, a hydrophobic face, and a hydrophilic face under appropriate conditions (e.g., 2.0% w/v peptide in 50 mM Bis Tris Propane, pH 7.4, 150 mM NaCl, at 25° C.). Under the appropriate conditions, the second amphiphilic cationic peptide self-assembles into a fibrillar network wherein the peptide is folded in an β-hairpin conformation in the fibrillar state.

The nanoparticle-hydrogel composite including a peptide hydrogel based on the second cationic amphiphilic peptide in a β-hairpin confirmation can readily be made by preparing an aqueous solution comprising one or more of the second cationic amphiphilic peptides (such as HLT2) and nanoparticle (such as a MAX1:miRNA particle) as disclosed herein and altering one or more characteristics of the solution, wherein a hydrogel is formed. The characteristic altered may be any characteristic that results in formation of a hydrogel upon its alteration. Suitable examples include, but are not limited to, ionic strength, temperature, concentration of a specific ion, and pH. In particular embodiments, the character altered may be the pH of the solution. The second cationic amphiphilic peptide forms a hydrogel at a pH of about 7 or higher. Increasing pH and increasing ionic strength both encourage hydrogel formation, and the two effects are roughly additive. Thus, the lower the pH, the higher the salt concentration necessary for hydrogel formation. In some embodiments, the hydrogel can be formed in a container (such as a syringe), for example a closed container.

In some embodiments, altering one or more characteristic of the solution results in a salt concentration of from about 10 mM to about 400 mM, such as about 50 to about 300 mM, about 100 to about 200 mM, or about 150 mM. Any salt may be used, for example, KCl, NaCl, $MgCl_2$, KF, $MgSO_4$, etc. In one embodiment, the salt may be NaCl. In some embodiments, the solution may have a desired pH, for example, a pH of from about 7 to about 9, a pH of from about 7.5 to about 8.5, a pH of from about 7.0 to about 8.0, or a pH of about 7.4, which may stay the same or be changed upon formation of the hydrogel.

In one non-limiting example, the hydrogel is formed in 50 mM Bis Tris Propane (BTP), 150 mM NaCl, pH 7.4. Any buffer system can be used except phosphate based buffer systems, as phosphate buffers are known to precipitate β-hairpin peptides. Accordingly, peptide hydrogels including second cationic amphiphilic peptide can simply be formed by, for example, adding buffer of appropriate ionic strength to an aqueous solution of unfolded peptide; drawing the resulting solution into a syringe; and allowing it to gel at 25° C. directly in the syringe.

The nanoparticle-hydrogel composite is a well hydrated solid material and have a stiffness greater than 40 Pascal (Pa), as measured by the storage modulus G' at a strain of 0.2%. Above approximately 40 Pa the material is a self-supporting solid gel material. The stiffness can reach greater than 10,000 Pa at higher peptide concentration. The nanoparticle-hydrogel composite typically contain at least 0.5 wt % of the second amphiphilic cationic peptide in an aqueous medium. For example, the disclosed nanoparticle-hydrogel composite may have varying amounts of second amphiphilic cationic peptide material. For example, the nanoparticle-hydrogel composite may be formed comprising a percent by weight of second amphiphilic cationic peptide of from about 0.25% w/v to about 4.0% w/v, from about 0.25% w/v to about 3.0% w/v, from about 0.25% w/v to about 2.0% w/v, from about 0.25% w/v to about 1.0% w/v, from about 0.5% w/v to about 4.0% w/v, from about 0.5% w/v to about 3.0% w/v, from about 0.5% w/v to about 2.0% w/v, from about 0.5% w/v to about 1.0% w/v, from about 1.0% w/v to about 4.0% w/v, from about 1.0% w/v to about 3.0% w/v, from about 1.0% w/v to about 2.0% w/v, from about 2.0% w/v to about 4.0% w/v, or from about 2.0% w/v to about 3.0% w/v.

In one aspect, the amount by weight of the second amphiphilic cationic peptide and the kinetics of gelation may be varied to produce a nanoparticle-hydrogel composite having a desired modulus (stiffness). Hydrogels of the invention may have a modulus from about 40 Pascal (Pa) to about 50,000 Pa, from about 40 Pa to about 25,000 Pa, from about 40 Pa to about 10,000 Pa, from about 40 Pa to about 5,000 Pa, from about 40 Pa to about 1,000 Pa, from about 40 Pa to about 500 Pa, from about 40 Pa to about 100 Pa, from about 100 Pa to about 50,000 Pa, from about 100 Pa to about 25,000 Pa, from about 100 Pa to about 10,000 Pa, from about 100 Pa to about 5,000 Pa, from about 100 Pa to about 2,000 Pa, from about 100 Pa to about 1,000 Pa, from about 100 Pa to about 500 Pa, or from about 100 Pa to about 250 Pa.

The resultant nanoparticle-hydrogel composite is mechanically rigid and displays shear-thinning/recovery behavior. This characteristic provides a free flowing suspension during the application of shear and complete reformation of the gel network (self-healing) after cessation of the shear. This combination of shear thinning and self-healing allows material formation in a spatially resolved manner. For example, in some embodiments, one of ordinary skill in the art can inject or spray (shear thin) a pre-formed nanoparticle-hydrogel composite into a target location in a subject where it self heals and reforms the nanoparticle-hydrogel composite. The shear stress converts the gel to a lower viscosity, flowable fluid. The shear stress is relieved when the fluid exits the syringe or spray nozzle and the gel quickly self-heals, recovering its original mechanical rigidity. This shear-thinning/recovery mechanism allows the nanoparticle-hydrogel composite to be easily delivered by syringe or spray to the target location in the subject.

Additional Description of Peptides in the Nanoparticle-Hydrogel Composite

The first and second amphiphilic cationic peptides for use in the disclosed embodiments can be any length appropriate for forming a nanoparticle complex with a nucleic acid molecule and for forming a peptide hydrogel, respectively. In some examples, the first and second peptides are from about 20 to about 75 residues (e.g., from about 20 to about 50 residues, from about 20 to about 40 residues, from about 20 to about 30 residues, from about 20 to about 25 residues, from about 20 to about 50 residues, from about 20 to about 40 residues, from about 20 to about 30 residues, or from about 20 to about 25 residues ("about" refers to plus or minus 2 residues). In some embodiments, the peptides for use in the disclosed embodiments can be from 20 to 75 residues (e.g., from 20 to 50 residues, from 20 to 40 residues, from 20 to 30 residues, from 20 to 25 residues, from 20 to 50 residues, from 20 to 40 residues, from 20 to 30 residues, or from 20 to 25 residues). In some embodiments, the peptide can be no more than 50 residues, such as no more than 30 residues or no more than 20 residues. In additional embodiments, the peptide can be 20, 25, 30, 35, 40, 45, or 50, residues in length. In some embodiments, the peptide can be 20 amino acids in length.

The first and second amphiphilic cationic peptides for use in the disclosed embodiments can be synthesized using any appropriate technique, such as automated solid phase procedures. The first and second amphiphilic cationic peptides may incorporate one or more modified amino acid residues (e.g., D-amino acids, homologs of naturally occurring amino acids, amino acids with modified side chains, etc.). Exemplary techniques and procedures for solid phase synthesis are described in *Solid Phase Peptide Synthesis: A Practical Approach*, by E. Atherton and R. C. Sheppard, published by IRL, Oxford University Press, 1989. Alternatively, apelin-36 (42-57) peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116: 4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). Other methods useful for synthesizing the apelin-36 (42-57) peptides of the disclosure are described in Nakagawa et al., *J. Am. Chem. Soc.* 107: 7087-7092, 1985.

Additional exemplary techniques for peptide synthesis are taught by Bodanszky, M. and Bodanszky, A., *The Practice of Peptide Synthesis*, Springer Verlag, New York, 1994; and by Jones, J., *Amino Acid and Peptide Synthesis*, 2nd ed., Oxford University Press, 2002. The Bodanszky and Jones references detail the parameters and techniques for activating and coupling amino acids and amino acid derivatives. Moreover, the references teach how to select, use and remove various useful functional and protecting groups. Peptides of the disclosure can also be readily purchased from commercial suppliers of synthetic peptides once the supplied is provided with the sequence of the peptide. Such suppliers include, for example, Advanced ChemTech (Louisville, KY), Applied Biosystems (Foster City, CA), Anaspec (San Jose, CA), and Cell Essentials (Boston, MA).

Following synthesis, exemplary techniques for peptide purification include reverse phase chromatography, high performance liquid chromatography, ion exchange chromatography, size exclusion chromatography, affinity chromatography, and gel electrophoresis. The actual conditions used to purify a particular peptide, or a modified form thereof, will depend, in part, on synthesis strategy and on factors such as net charge, hydrophobicity, hydrophilicity, and the like.

Additional Agents Encapsulated Within the Nanoparticle-Hydrogel Composite

In some embodiments, the disclosed nanoparticle-hydrogel composite includes one or more heterologous agents dispersed within the hydrogel.

For example, in some embodiments, the nanoparticle-hydrogel composite includes one or more heterologous anti-cancer agents dispersed within the hydrogel. Non-limiting examples of anti-cancer agents include a cytokine, a chemokine, an antibody, or a chemotherapeutic agent. The cytokine can be, for example, interleukin-2 (IL-2), granulocyte macrophage colony stimulating factor (GM-CSF), or interferon, such as interferon (IFN) β. In some embodiments, the antibody is a PD-1 antagonist, such as antibody that specifically binds PD-1 or PD-L1, such as MPDL3280A.

Non-limiting examples of chemotherapeutic agents that can be included in the nanoparticle-hydrogel composite include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and thioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

In a particular example, for a nanoparticle-hydrogel composite for use in treating malignant pleural mesothelioma, the heterologous anti-cancer agent included in the nanoparticle-hydrogel composite comprises pemetrexed, cisplatin, bevacizumab, carboplatin, gemcitabine, vinorelbine, or a combination of two or more thereof.

In a particular example, for a nanoparticle-hydrogel composite for use in treating cervical cancer, the heterologous anti-cancer agent included in the nanoparticle-hydrogel composite comprises cisplatin, fluorouracil, paclitaxel, bevacizumab, tototecan, carboplatin, gemcitabine, or a combination of two or more thereof.

In a particular example, for a nanoparticle-hydrogel composite for use in treating a thymoma or thymic carcinoma, the heterologous anti-cancer agent included in the nanoparticle-hydrogel composite comprises cisplatin, doxorubicin, cyclophosphamide, prednisone, vincristine, etoposide, ifosfamide, paclitaxel, or a combination of two or more thereof.

In a particular example, for a nanoparticle-hydrogel composite for use in treating ovarian cancer, the heterologous anti-cancer agent included in the nanoparticle-hydrogel composite comprises paclitaxel, cisplatin, carboplatin, docetaxel, bevacizumab, or a combination of two or more thereof.

In a particular example, for a nanoparticle-hydrogel composite for use in treating non-small cell lung cancer, the heterologous anti-cancer agent included in the nanoparticle-hydrogel composite comprises paclitaxel, cisplatin, carboplatin, docetaxel, bevacizumab, pemetrexed, etoposide, gemcitabine, vinorelbine, or a combination of two or more thereof.

In a particular example, for a nanoparticle-hydrogel composite for use in treating non-small cell lung cancer, the heterologous anti-cancer agent included in the nanoparticle-hydrogel composite comprises paclitaxel, cisplatin, carboplatin, docetaxel, bevacizumab, pemetrexed, etoposide, gemcitabine, vinorelbine, or a combination of two or more thereof.

The amphiphilic peptides disclosed herein are cationic. Accordingly, in typical embodiments involving a heterologous agent encapsulated within the peptide hydrogel, the heterologous agent has a neutral or net positive charge to prevent binding of the agent to the hydrogel matrix. Depending on the agent, the neutral or net positive charge may lead to varying retention time in the peptide hydrogel.

Peptide hydrogels including a heterologous agent can be readily produced by preparing an aqueous solution comprising the heterologous agent (such as a chemotherapeutic agent) and the second amphiphilic β-hairpin peptide (such as HLT2) and nanoparticle (such as a MAX1:miRNA particle) as disclosed herein and altering one or more characteristics of the solution, wherein a hydrogel is formed. As discussed above, the characteristic altered may be any characteristic that results in formation of a hydrogel upon its alteration, such as ionic strength, temperature, concentration of a specific ion, and pH. In some embodiments, the hydrogel including the heterologous agent can be formed in a container (such as a syringe), for example a closed container.

The peptide hydrogel including an encapsulated heterologous agent can be used for any suitable purpose. For example, peptide hydrogels with an encapsulated heterologous agent can be administered to a subject in need thereof (for example, by injection to a target location in the subject).

C. Treatment and Prevention of Cancer

It is shown herein that administration of an embodiment of the disclosed nanoparticle-hydrogel composite including HLT2-based hydrogel and MAX1:hsa-miR-215 nanoparticles inhibits the growth and metastasis of tumors in vivo. This observation supports the use of the disclosed nanoparticle-hydrogel composites as therapeutics for the treatment an inhibition of cancer.

Accordingly, methods are disclosed herein for treating or inhibiting cancer in a subject by administrating an effective amount of disclosed nanoparticle-hydrogel composite to the subject. The nanoparticles in the composite comprise a nucleic acid molecule that has an anti-cancer effect when introduced into cells. For example, the nucleic acid molecule can be a miRNA, or a mimic and/or mimetic thereof, with anti-cancer activity, or a plasmid DNA vector encoding a miRNA, or a mimic and/or mimetic thereof, with anti-cancer activity. In particular examples, the methods include administering to a subject with cancer an effective of a nanoparticle-hydrogel composite comprising nanoparticles containing one or more miRNAs that are down-regulated in the cancer, in order to treat or inhibit the cancer in the subject. In another example, the methods include administering to a subject with cancer an effective of a nanoparticle-hydrogel composite comprising nanoparticles containing one or more anti-miRs (miRNA Inhibitors) that specifically bind to miR-NAs that are up-regulated in the cancer, in order to treat or inhibit the cancer in the subject.

In some embodiments, the methods include treating an existing cancer in a subject. In additional embodiments, methods are disclosed herein are used for preventing metastasis of a cancer in a subject.

Subjects that can benefit from the disclosed methods include humans and veterinary subjects. A suitable administration format may be determined by a medical practitioner for each subject individually.

Subjects can be screened prior to initiating the disclosed therapies, for example to determine whether the subject has cancer, such as a serosal neoplasm (e.g., malignant pleural mesothelioma). The presence of the cancer in the subject indicates that the cancer can be treated using the methods provided herein. The presence of a cancer in a subject can be determined by methods known in the art, and typically include cytologic, morphologic, or molecular-based evaluation. The cancer can be one with an established tumor. The cells of the cancer that are screened can be in vivo or ex vivo, including cells obtained from a biopsy. In some embodiments, a subject can be selected for treatment that has, is suspected of having, or is at risk of developing, cancer, a serosal neoplasm (e.g., malignant pleural mesothelioma).

The cancer treated by the methods disclosed herein can be any cancer of interest, including, but not limited to, a serosal neoplasm (e.g., malignant pleural mesothelioma). Non-limiting examples of cancers that can be treated using the disclosed methods include skin cancers, breast cancers, brain cancers, cervical carcinomas, testicular carcinomas, head and neck cancers, gastrointestinal tract cancers, genitourinary system cancers, gynecological system cancers, endocrine system cancers, a sarcoma of the soft tissue and bone, a mesothelioma, a melanoma, and a neoplasm of the central nervous system. In some embodiments, the cancer is a head and neck cancer, such as cancers of the nasal cavity, paranasal sinuses, nasopharynx, oral cavity, oropharynx, larynx, hypopharynx, salivary glands, and paragangliomas. In other embodiments, the cancer is a lung cancer, such as a non-small cell lung cancer or a small cell lung cancer. In further embodiments, the cancer can be a cancer of the gastrointestinal tract, such as cancer of the esophagus, stomach, pancreas, liver, biliary tree, small intestine, colon, rectum and anal region. In yet other embodiments, the cancer can be a cancer of the genitourinary system, such as cancer of the kidney, urethra, bladder, prostate, urethra, penis and testis. In some embodiments, the cancer is a gynecologic cancer, such as cancer of the cervix, vagina, vulva, uterine body, gestational trophoblastic diseases, ovarian, fallopian tube, peritoneal, or breast. In other embodiments, the cancer is an endocrine system cancer, such as a thyroid cancer, parathyroid cancer, adrenal cortex cancer, pancreatic endocrine cancer, carcinoid cancer and carcinoid syndrome. The cancer can be a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of cancers, rhabdomyosarcoma. The cancer can be a lymphoma, comprising non-Hodgkin's lymphomas, cutaneous T-cell lymphomas, primary central nervous system lymphoma, and Hodgkin's disease. The cancer can be plasma cell neoplasms, a cancer of unknown primary site, a peritoneal carcinomastosis, a Kaposi's sarcoma, AIDS-associated lymphomas, AIDS-associated primary central nervous system lymphoma, AIDS-associated Hodgkin's disease and AIDS-associated anogenital cancers, a metastatic cancer to the liver, metastatic cancer to the bone, malignant pleural and pericardial effusions and malignant ascites. In specific non-limiting examples, the cancer is a serosal neoplasm (e.g., malignant pleural mesothelioma).

In some non-limiting embodiments, the method includes treating or inhibiting a cancer present or at risk of being present at a serosal surface (e.g., part of a serosal body cavity) lined by mesothelial cells in the subject. In some non-limiting embodiments, the method include treating or inhibiting a cancer present or at risk of being present in a serosal body cavity in the subject, such as a pleural cavity, a pericardial cavity, an anterior mediastinal cavity, a posterior mediastinal cavity, a peritoneal cavity, or a tunica vaginalis testis cavity. In some embodiments, the cancer is a serosal neoplasm, such as a pleural mesothelioma, a peritoneal mesothelioma, a thymic epithelial cancer (i.e. a thymoma, a thymic carcinoma), an ovarian carcinoma, a cervical cancer, a small-cell lung carcinoma, a non-small-cell lung carcinoma, an ovarian carcinoma, or an appendiceal cancer.

In a preferred embodiment, the disclosed methods are used to treat malignant pleural mesothelioma in a subject. Treatment of the malignant pleural mesothelioma can reduce a symptom of the malignant pleural mesothelioma in the subject. Symptoms include respiratory symptoms, such as coughing, coughing up blood, wheezing and/or shortness of breath, systemic symptoms such as weight loss, fever, or fatigue, or symptoms due to local compression, such as chest pain, bone pain, or difficulty swallowing. Generally, the methods include selecting a subject having a malignant pleural mesothelioma, and administering to the subject a therapeutically effective amount of a disclosed nanoparticle-hydrogel composite. Treatment of the malignant pleural mesothelioma is generally initiated after the diagnosis of the cancer. A subject with any stage of malignant pleural mesothelioma can be treated using the method disclosed herein. The presence of malignant pleural mesothelioma can be determined by methods known in the art, such as a chest x-ray, CT scan, a PET scan, MRI and/or endobronchial ultrasound. Pulmonary function tests can also be used. The malignant pleural mesothelioma can also be diagnosed by obtaining one or more biopsies and evaluating the cells in the biopsy.

Treatment of the cancer is generally initiated after the diagnosis of the cancer, or after the initiation of a precursor condition (such as metaplasia or dysplasia). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers. In some examples, treatment is administered to a subject with a pre-cancerous tumor that can convert into a malignant or even metastatic tumor.

Treatment initiated after the development of a condition, such as malignant cancer, may result in decreasing the severity of the symptoms of one of the conditions, or completely removing the symptoms, or reducing metastasis, tumor volume or number of tumors. In some example, the cancer becomes undetectable following treatment.

In one aspect of the disclosure, the formation of tumors in the treated subject, such as metastasis, is delayed, prevented or decreased. In another aspect, the size of the primary tumor in the treated subject is decreased. In a further aspect, a symptom of the tumor is decreased. In yet another aspect, tumor volume is decreased.

Treatment prior to the development of the condition, such as treatment upon detecting dysplasia or an early (benign) precursor condition, is referred to herein as treatment of a subject that is "at risk" of developing the condition. Administration to a target location in the subject where the cancer is "at risk of being present" refers to administration to a target location in the subject where a cancer has not formally been detected, but where there is a possibility of current cancer, or a possibility of developing a current cancer within a suitable time frame (such as within one year). This includes a site of dysplasia or an early (benign) precursor condition, and/or a site of pre-operative, intra-operative, or post-operative surgical treatment (such as tumor resection) of a cancer, for example, where there is concern that the cancer may not have been fully removed by the surgical procedure.

In some examples, treatment using the methods disclosed herein prolongs the time of survival of the subject (e.g., increases survival time by at least 6 months, at least 9 months, at least 12 months, at least 2 years, at least 3 years, or even at least 5 years relative to the absence of the therapy).

One skilled in the art can readily determine an effective amount of a disclosed nanoparticle-hydrogel composite to be administered to a subject, for example, taking into account factors such as the type of tumor being treated, the extent of disease progression, the age, health and sex of the subject, the size (e.g., weight and/or height) of the subject, and the route of administration. For example, the effective amount can be based on the approximate body weight of a subject to be treated. Such effective amounts can be administered by any suitable route. In some embodiments, the effective amount of the nanoparticle-hydrogel composite can be based on the amount/concentration of the nanoparticles dispersed within the nanoparticle-hydrogel composite containing therapeutic nucleic acid molecules.

An effective amount of the nanoparticle-hydrogel composite is that which provides either subjective relief of a symptom(s) or an objectively identifiable improvement as noted by the clinician or other qualified observer. In one embodiment, an effective amount of the nanoparticle-hydrogel composite is the amount necessary to inhibit tumor growth (such as growth of a lung tumor), metastasis of the tumor, or the amount that is effective at reducing a sign or a symptom of the tumor. The effective amount of the agents administered can vary depending upon the desired effects and the subject to be treated. In some examples, an effective amount is an amount that eliminates or reduces the patient's tumor burden, or that prevents or reduces the growth of metastatic cells.

In some examples, an effective amount of a disclosed nanoparticle-hydrogel composite comprises miRNA nucleic acid (or combination of miRNA nucleic acids) of from about 5 µg/kg to about 100 mg/kg of body weight, such as about 100 µg/kg to about 10 mg/kg, about 1 mg/kg to about 25 mg/kg, about 20 mg/kg to about 40 mg/kg, about 30 mg/kg to about 50 mg/kg, or about 40 mg/kg to about 100 mg/kg. In one non-limiting example, the amount administered is about 5 mg/kg of a miRNA nucleic acid (or a combination of miRNA nucleic acids).

The particular mode of administration and the dosage regimen will be selected by the attending clinician, taking into account the particulars of the case (e.g. the subject, the disease, the disease state involved, and whether the treatment is prophylactic). The nanoparticle-hydrogel composite can be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the nanoparticle-hydrogel composite to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. Administration may begin whenever appropriate as determined by the treating physician.

The disclosed nanoparticle-hydrogel composite can be administered to a subject in need of treatment using any suitable means. Methods of administration include, but are not limited to, intraductal, intradermal, intramuscular, intraperitoneal, intrapleural, subcutaneous, vaginal, rectal, intranasal, inhalation. One of skill in the art can select an appropriate route of administration, depending on the therapeutic agent(s), the condition being treated, the health and treatment history of the subject, and other relevant clinical factors.

The nanoparticle-hydrogel composite displays shear-thin/recovery mechanical properties, which allow the nanoparticle-hydrogel composite and any additional therapeutic dispersed within the hydrogel to be delivered locally to a body cavity, for example, via percutaneous or surgical access by syringe injection, or spray delivery to coat anatomic surfaces. After application, the nanoparticles time-release from the hydrogel matrix to adjacent tissues and are taken up by cells. Once internalized by cells, the nucleic acid molecule is released from the nanoparticle and (depending on the nucleic acid molecule) may affect cellular function.

In the case of malignant pleural mesothelioma, the nanoparticle hydrogel composite could be sprayed via a handheld device or through the tip of a minimally invasive surgical instrument during the conduct of surgical resection or diagnosis of this disease. Surgical approaches include open thoracotomy, VATS (video-assisted thoracoscopic surgery), and/or robotic-assisted thoracoscopic surgery. Administration onto the parietal and visceral body surfaces of the composite material could occur before planned surgical resection of tumor or after surgical resection. Depending on the clinical scenario, the nanoparticle hydrogel composite could be applied in this manner repeatedly.

In some embodiments, nanoparticle-hydrogel composite is delivered to a serosal surface (e.g., part of a serosal body cavity) in the subject where the cancer is present or is at risk of being present by direct syringe injection or spray delivery. For example, the serosal surface can be part of a pleural cavity, a pericardial cavity, an anterior mediastinal cavity, a posterior mediastinal cavity, a peritoneal cavity, or a tunica vaginalis testis cavity in the subject. Administration of the nanoparticle-hydrogel composite in this way coats all or a portion of the serosal surface in the subject where the cancer is present or is at risk of being present.

The present disclosure also includes methods of treating a subject with combinations of the nanoparticle-hydrogel composite (containing a therapeutic nucleic acid molecule) with one or more other agents useful in the treatment of a cancer. For example, the nanoparticle-hydrogel composite can be administered in combination with effective doses of one or more heterologous anti-cancer agents (such as a chemotherapeutic agent or anti-cancer protein) dispersed within the hydrogel. A skilled clinician can select an appropriate combination of therapies based on the type of tumor being treated, the subject's clinical history, overall condition, and other factors.

EXAMPLES

The following examples are provided to illustrate particular features of certain embodiments, but the scope of the claims should not be limited to those features exemplified.

Example 1 microRNA-Templated Peptide Assembly within a Nanocomposite Peptide Hydrogel Network This example illustrates a nanoparticle/hydrogel composite material that can be used to local delivery of therapeutic agents to complex anatomical surfaces in vivo. The nanoparticle/hydrogel composite material provides multiple benefits, including: (i) it is both syringe-injectable and sprayable to effectively cover complex tissue surface topology, (ii) it can be used to deliver nucleic acid (e.g., miRNA) in a sustainable manner to the tissue, (iii) it facilitates intracellular transport of the delivered nucleic acid (e.g., miRNA), (iv) it is biodegradable, and (v) it can be effective with a single administration to improve patient compliance.

In several examples, the nanoparticle/hydrogel composite material is useful for delivery of therapeutic miRNA for treatment of cancers or complex anatomical surfaces. Cancers that access anatomic surfaces such as the pleural or peritoneal cavities represent challenging clinical scenarios with limited curative interventions. Pleura involvement by thymoma, disseminated late stage ovarian cancer in the abdominopelvic region, or colon cancer peritoneal carcinomatosis, are a few common examples of surface malignancies without effective therapies. Quite remarkably, surface cancers represent an increasingly prevalent situation of modern oncology care. A consistent unifying feature of these diverse cancers is involvement of complex anatomic surfaces contributing to biologic behavior that eludes therapeutic interventions.

In contradistinction to surface malignancies that arise by metastasis, primary cancers that occupy large surfaces such as malignant mesothelioma represent a more formidable challenge. Mesothelioma is a recalcitrant, asbestos-related malignancy arising from mesothelial cells lining body cavity surfaces (pleural or peritoneal). Contrary to predictions, the worldwide incidence of pleural mesothelioma continues to rise with expected hundreds of thousands of future cases. Prognosis is dismal with a median survival of 12-18 months and 5-year survival of <5%, even though this cancer rarely metastasizes. Pleural mesothelioma remains incurable because: a) it is inherently chemoresistant (in part, driven by polyclonality) with a tumor response rate up to 30%, without any new FDA-approved drugs the past 15 years, b) modern hemithoracic radiation, although safe, is hampered by toxicity to critical organs and remains investigational, and c) radical surgery cannot achieve negative margins owing to complex anatomic surfaces. While the optimal therapeutic modality is debatable, recent meta-analyses show that surgical resection improves overall survival versus non-surgical approaches (radiation and/or chemotherapy). However, the major limitation of a macroscopic complete resection is local recurrence of disease in 75% or more of patients completing multi-modal surgery-based therapy. This is due to residual microscopic tumor foci regrowth left from resection procedure. Moreover, adjuvant intraoperative schemes, such as heated chemotherapy and photodynamic light, remain experimental without widespread adoption.

miRNAs are short noncoding RNA involved in critical biological processes where they participate in coherent regulation of multiple genes and pathways via base-pairing interactions with mRNA transcripts. In principle, miRNAs repurposed as therapeutics are less prone to tumor cell adaptive resistance while able to profoundly change intracellular phenotype upon expression or suppression in context-specific environments. Although a great deal of work has been done to generate systemic miRNA delivery systems, mesothelioma and other surface cancers necessitate devices that can deliver nucleic acids to anatomically complex tissue topology in a locoregional fashion. Tumor resection from a tissue surface such as pleural or peritoneal linings leave behind a tortuous complex exterior hindering effective delivery.

A feature of the engineered hydrogel involves pre-condensation of negatively charged miRNA into nanoparticles to overcome the delivery barrier through the cell membrane. Apart from utilizing a self-assembling peptide to constitute the hydrogel matrix, the soluble form of a positively charged peptide was employed to condense miRNA into nanoparticulates (FIG. 1). The amount of positive charge imbibed within the peptide composing the nanoparticles plays a role in effective complexation of miRNA. Further, the interplay of biophysical attributes between peptides in the hydrogel matrix and those in the nanoparticles can tune the overall miRNA delivery efficiency. Provided herein is evidence demonstrating the ability of this biodegradable hydrogel composite to induce sustained therapeutic effects with a single administration in several different microenvironments of mesothelioma via multiple preclinical models.

To prepare the nanoparticle-hydrogel composite, nanoparticles were first formulated by complexing miRNA to a linear Peptide 1 (MAX1, VKVKVKVKV$^D$PPTKVKVKVKV-NH$_2$) via electrostatic interaction between the cationic peptide and anionic RNA (see FIG. 1A, Stage 1). For miRNA-215, miRNA-206 and the other miRNAs, a molar ratio of Peptide 1 to miRNA was maintained at 50:1 irrespective of the amount of RNA complexed. However, this ratio can vary with the identity of the miRNA. As a specific example, to complex miRNA-215, 12.5 µL of a 300 µM Peptide 1 (MAX1) solution in RNase free water was added to a 12.5 µL of a 6 µM solution of miRNA-215 in RNase free water. The resulting suspension was incubated for 30 min at 37° C. with constant agitation to form the Peptide 1/MAX1:RNA nanoparticles (see the transmission electron microscope (TEM) image of nanoparticles in FIG. 2B). Particular features of the Peptide 1 (MAX1) relevant to complex the RNA are: 1) Peptide 1 (MAX1) has a formal charge of (+9) at neutral solution pH, this ensures moderate (but not too tight) binding of RNA, so that the particle stays intact (the Peptide 1 (MAX1)/RNA does not separate) while encapsulated in the peptide hydrogel during cellular uptake. However, once internalized by cells, the miRNA is released from the Peptide 1 (MAX1) peptide. 2) Peptide 1 (MAX1) remains in an unfolded state while complexed to the RNA. This helps the peptide dissociate from the RNA once internalized by cells. 3) Peptide 1 (MAX1) contains no negatively charged amino acids in its sequence, which disfavors RNA binding via electrostatic repulsion.

To encapsulate the nanoparticles into the hydrogel (FIG. 1A, Stage 2), 25 µL of the nanoparticle suspension was mixed with 25 µL of HEPES buffer (50 mM HEPES, 300 mM NaCl, pH 7.4). The resulting suspension was then added to a 50 µL solution of Peptide 3 (HLT2, VLTKVKTKV$^D$PLPTKVEVKVLV-NH$_2$, 3.5 mM in 25 mM HEPES, pH 7.4). This triggers self-assembly of the HLT2 peptide into a fibrillar network leading to gelation. Gelation was allowed to proceed for 18 hours at 37° C. to afford the final nanoparticle-hydrogel composite comprised of 0.5 wt % HLT2 gel containing the MAX1:RNA nanoparticles. 1 wt % Peptide 3 (HLT2) gels were also used successfully. The TEM micrograph at FIG. 4F shows Peptide 1:RNA nanoparticles encapsulated within the fibrillar hydrogel network of Peptide 3 (HLT2). Particular features of the Peptide 3 (HLT2) gel relevant for encapsulating the Peptide 1/MAX1-miRNA nanoparticles are: 1) At low wt % (0.5-1.0), it assembles into fibrillar networks characterized by mesh sizes of 100-500 nm, enabling the slow sustained-release of the 150-200 nm MAX1:RNA nanoparticles. 2) The fibrillar networks formed by the self-assembly of cationic HLT2 are positively charged, which provides a stable environment for the encapsulated nanoparticles. MAX1:RNA nanoparticles are not stable when encapsulated within negatively charged hydrogel networks, decomposing quickly to release free naked RNA to the solution, which is poorly internalized by cells.

Figure 1C:
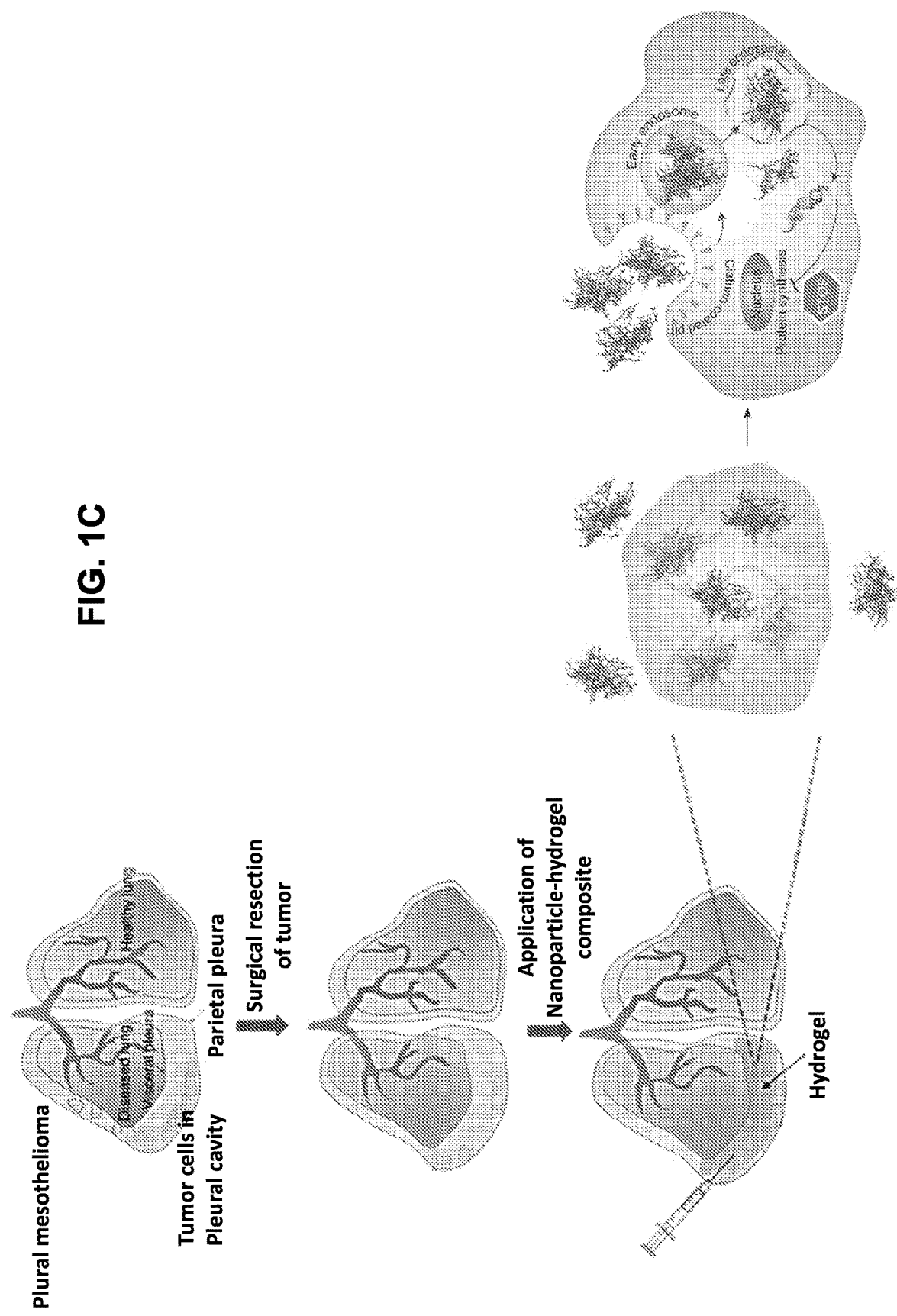

The nanoparticle-hydrogel composite material can be delivered either by shear-thin syringe delivery of by spray delivery to thoroughly coat complex anatomical surfaces (see, e.g., FIG. 1B). This allows the miRNA to be delivered to cells locally at the point of application in complex tissue environment often associated with surface cancers.

Figure 2A:
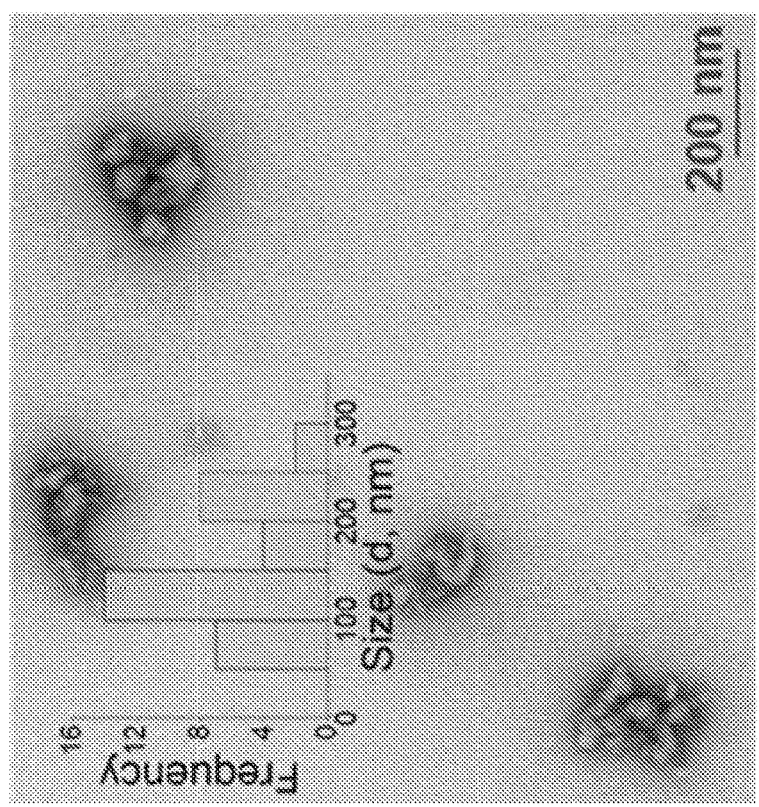
FIGS. 2A-2D. Biophysical characterization of peptide/miRNA nanoparticles.

Nanoparticles distributed around the hydrogel network is the main mediator of miRNA transfection once it releases from the gel assembly. The biophysical parameters and miRNA transfection efficiency of these nanoparticles was characterized. Three different peptides each having a four-residue type II' β-turn promoting region -V$^D$PPT- and varying positive charges (+9 to +5 at physiological pH) were initially used to condense miRNA (FIG. 2A). These peptides consist of two β-strands having alternating hydrophilic and hydrophobic residues (Schneider, et al. J Am Chem Soc, 124(50): 15030-15037, 2002). Peptide 2 (+7) contains a glutamic acid at position 15 to replace one lysine as present in Peptide 1 (+9) (Haines-Butterick, et al. Proc Natl Acad Sci USA, 104(19): 7791-7796, 2007). Replacement of two more lysine residues at position 2 and 19 with leucine along with substitution of a valine at position 3 generate Peptide 3 (+5). In aqueous solutions or in low ionic strength, these peptides stay in an ensemble of random conformations due to intra-strand electrostatic repulsions among the positively charged lysine residues (Sinthuvanich, et al. Biomaterials, 33(30): 7478-7488, 2012). Once in a solution of physiologically relevant ionic strength, salt ions help pacify the lysine-borne positive charges and result in folding the peptides into facially amphiphilic β-hairpin structures. Peptides studied herein to formulate nanoparticles were used in low micromolar concentrations in presence of water to avoid formation of self-assembled structures.

Figure 2B:
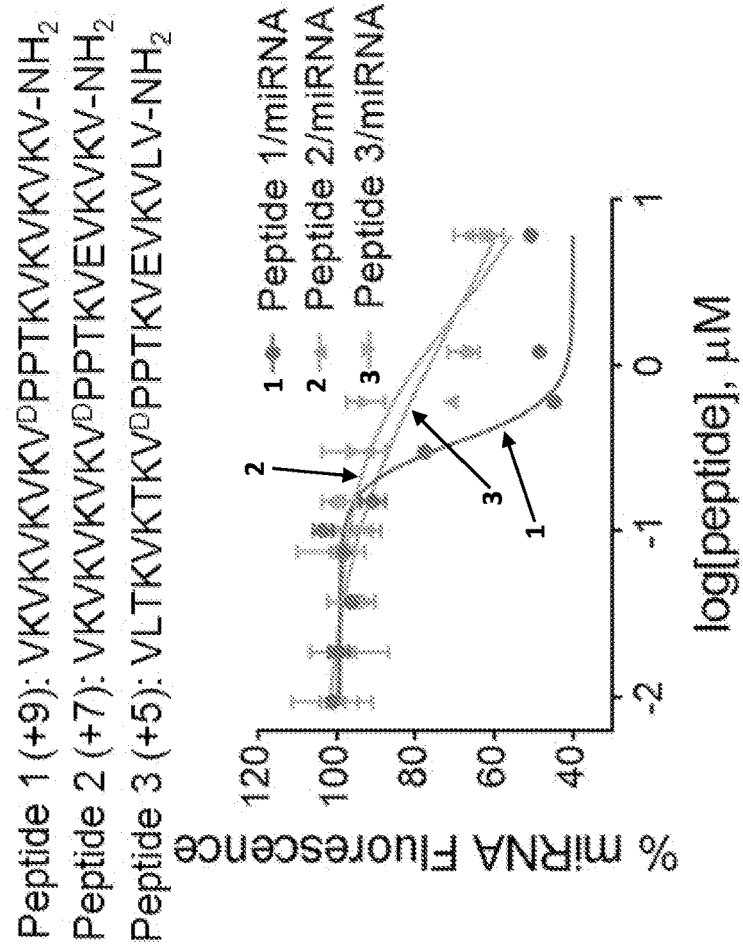
Figure 7A:
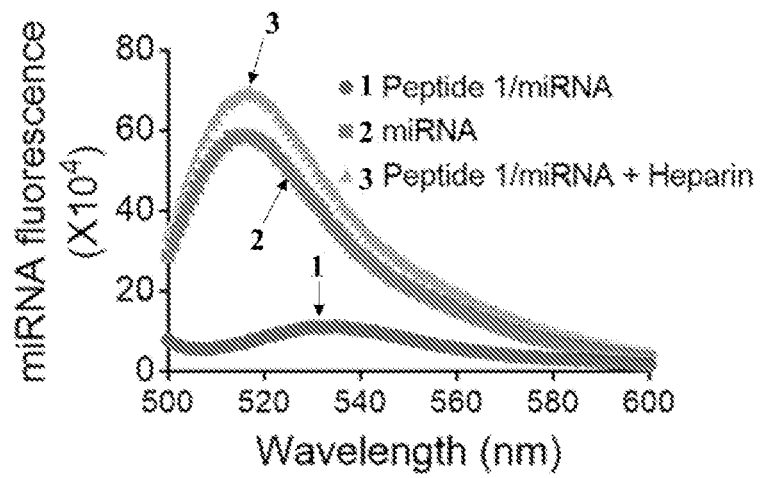
FIGS. 7A-7C. Biophysical investigation of binding between Peptide 1 and miRNA.

Binding interactions among peptides and miRNA were studied using a fluorescence measurement. Scrambled miRNA (sequence mismatched with all possible mRNAs in human) labeled with FAM (6-carboxyfluorescein, 5' end) was mixed with peptides having peptide vs miRNA molar ratio ranging from 0.3125 to 1000. Complexation was first performed in water, followed by dilution of the complex with HEPES (25 mM HEPES, pH 7.4) to keep pH of the suspension unaltered across all peptide concentrations. With increasing mole ratio, FAM fluorescence gradually gets quenched resulting from peptide-mediated condensation. Extent of quenching was found to be the maximal for Peptide 1 (FIGS. 2B, 7A). As expected, lower positive charge of Peptides 2 and 3 were not able to promote significant condensation of miRNA. Concentrations of Peptide 1 to induce maximum quenching were close to a molar ratio of 50:1 between Peptide 1 and miRNA which corresponds to an N/P ratio (charge ratio) of 10:1. Accordingly, a ratio of 10:1 as the N/P ratio was used for further assessment.

Figure 7B:
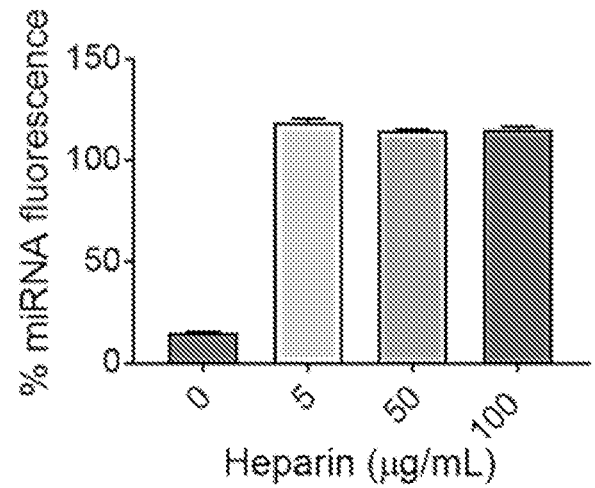
Figure 7C:
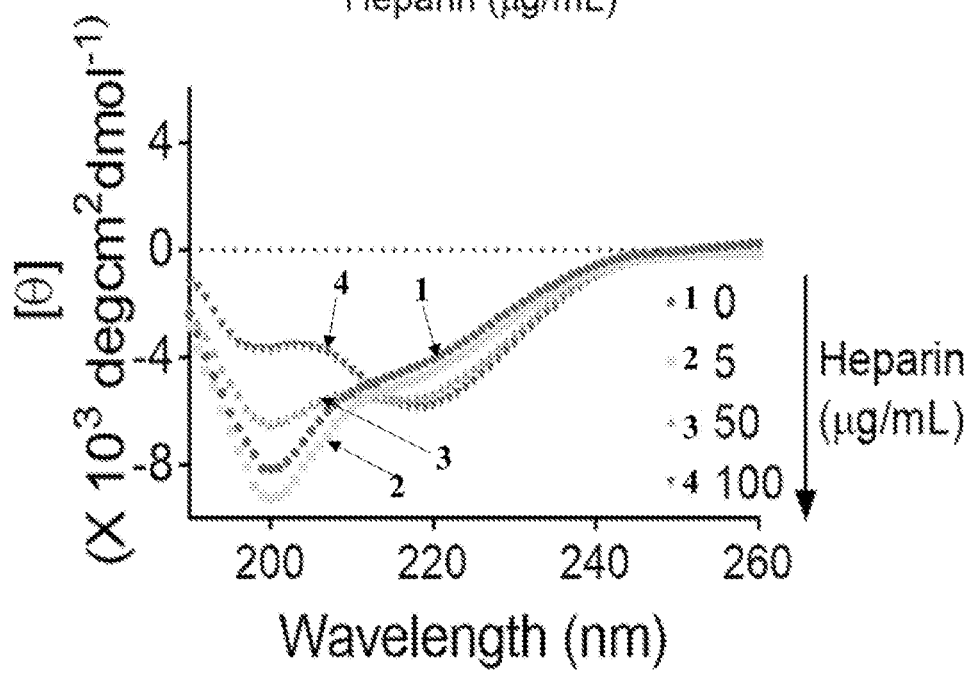

Measuring release of miRNA is an important step to determine the in vitro efficacy of the nanoparticle-loaded hydrogel composites. miRNA can be released from the nanoparticles by addition of heparin, a negatively charged cell-surface proteoglycan (FIGS. 7A-7C). Heparin sequesters positively charged peptides, helping miRNA to release, resulting in the recovery of previously quenched fluorescence. As shown in Figure FIGS. 7A-7B, addition of heparin to the nanoparticle suspension of Peptide 1/miRNA releases quantitative amount of miRNA, evident from recovered fluorescence. Addition of as little as 5 µg/mL of heparin was sufficient to release all miRNA, even though this concentration was not enough to induce significant structural change in Peptide 1. This is evident from CD spectra reported in FIG. 7C where evolution of β-sheet structure for Peptide 1 only starts at heparin concentration of 50 µg/mL. Accordingly, to determine release of miRNA, 50 µg/mL was chosen as the final heparin concentration to be added into the release supernatant of nanocomposite hydrogel.

Figure 8B:
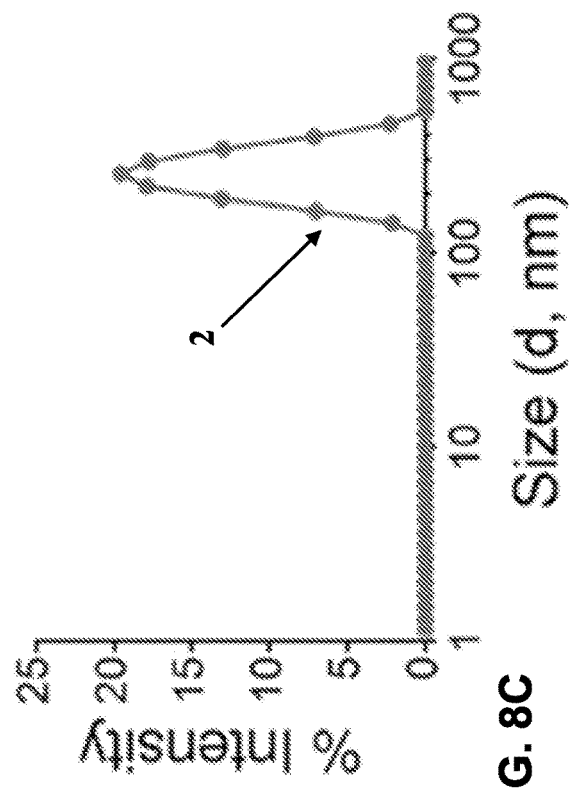
FIGS. 8A-8F. Biophysical characterization of Peptide 1/miRNA nanoparticles and Lipofectamine/miRNA complex. Dynamic Light Scattering-determined size distribution profiles of miRNA complexes of Peptide 1 and Lipofectamine were derived from correlation diagram as shown in (8A). Histograms showing (FIGS. 8B and 8C) particle size distribution and (FIGS. 8D and 8E) zeta potential for Peptide 1/miRNA and Lipofectamine/miRNA complexes in water at 25° C. Zeta potential distribution is shown in (FIG. 8F) for miRNA alone in water at 25° C. Lipofectamine/miRNA complex was formulated according to manufacturer's instructions.
Figure 8C:
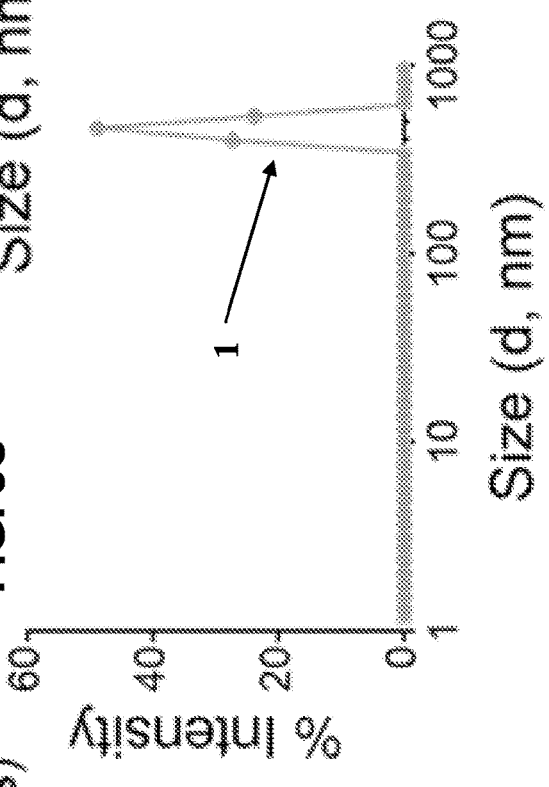
Figure 8A:
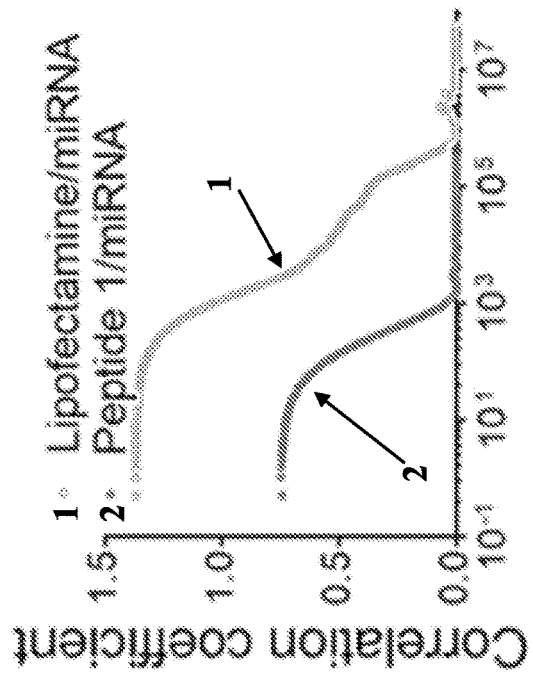
Figure 8D:
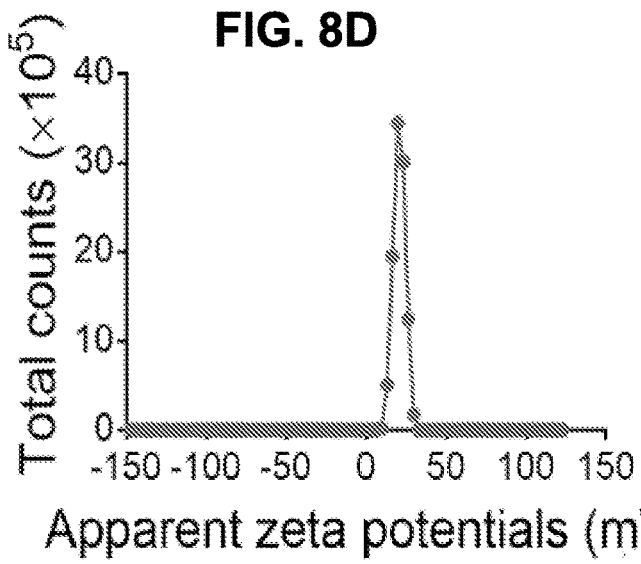
Figure 8E:
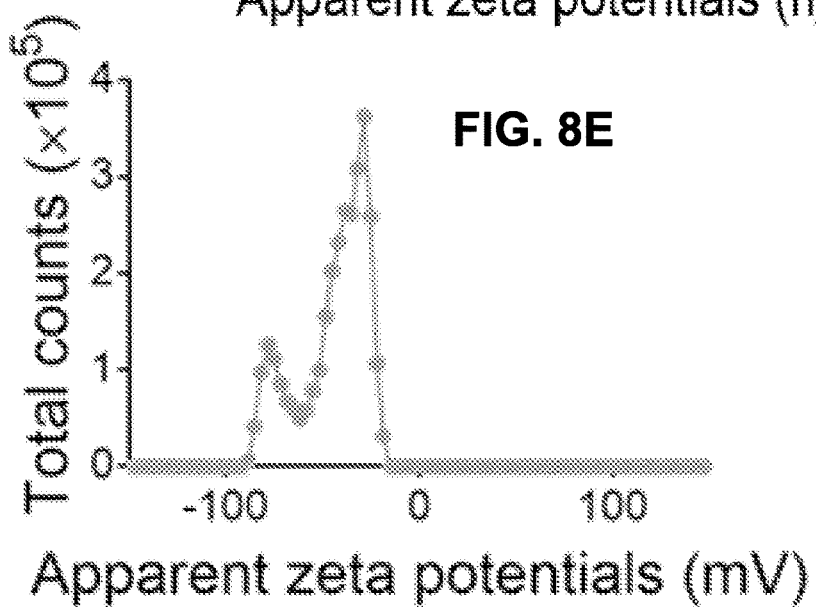
Figure 8F:
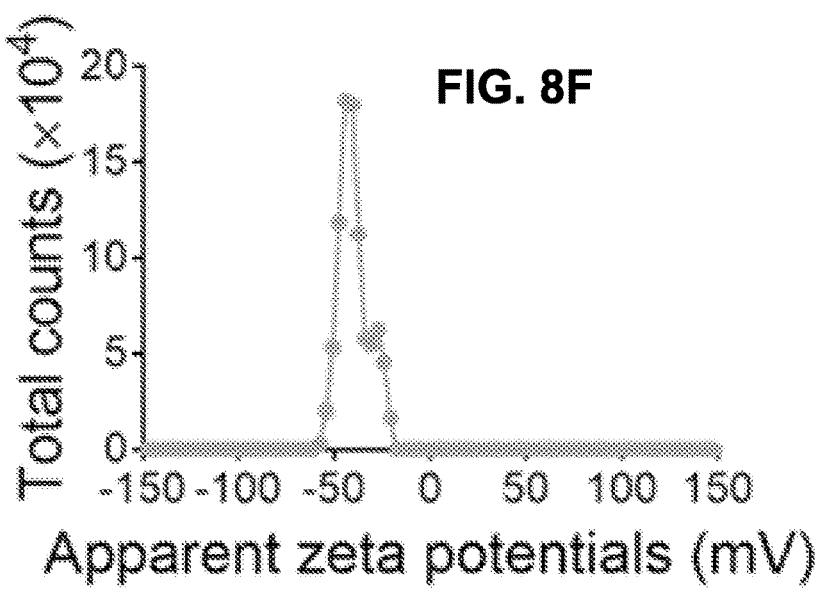

Size and zeta potential of Peptide 1/miRNA nanoparticles were compared to miRNA complexes of Lipofectamine RNAiMAX, a widely used commercially available transfection reagent. Corresponding complexes formed large aggregates with zeta potential of −39.9±7.8 mV (FIGS. 8A, 8C). zeta potential is described in Zhang, et al. (Nat Commun 7, 10376, 2016). Well-defined correlograms for Peptide 1/miRNA nanoparticles were commensurate with their Polydispersity indices of 0.08 (FIGS. 8A, 8B). Zeta potential of these nanoparticles were observed to be around 15.6±0.5 mV (FIG. 8D) as compared to −45.6±8.8 mV for naked miRNA (FIG. 8G).

Figure 9A:
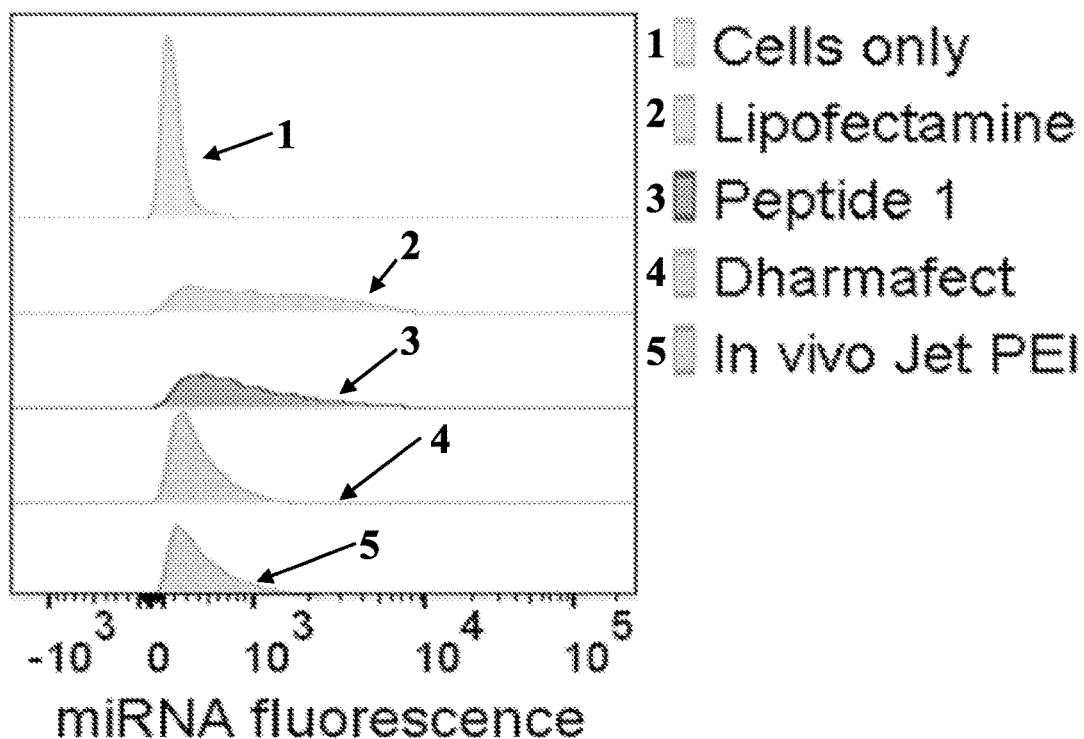
FIGS. 9A-9B. Intracellular delivery of miRNA by Peptide 1/miRNA nanoparticles in human pleural mesothelioma cell line H2052.

Hydrodynamic diameter of the nanoparticles made up of Peptide 1 were 263 nm (FIG. 9A). Positive surface charge of the peptide nanoparticles indicated adequate shielding of miRNA. Transmission electron micrographs (TEM) of these nanoparticles are shown in FIG. 2B. Size distribution calculated from TEM images shown at the inset indicates a size of ~200 nm for each set of particles.

Figure 2D:
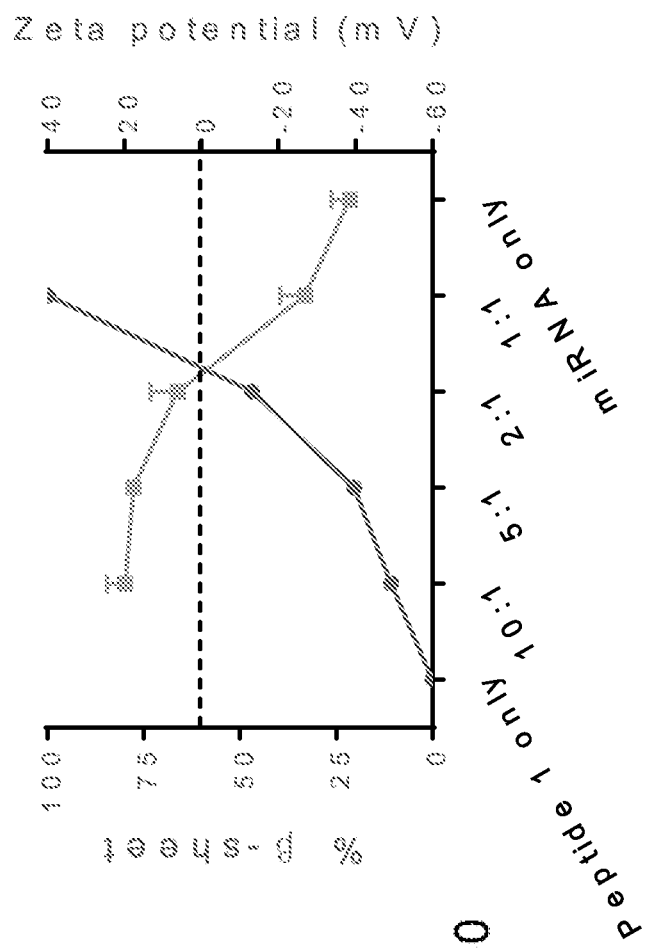
Figure 2C:
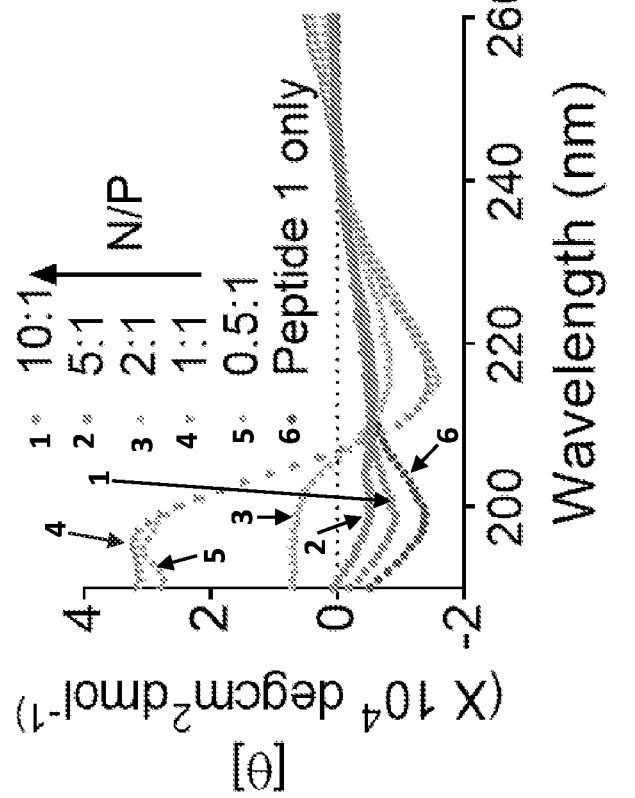

Circular Dichroism (CD) spectra was recorded to understand folding propensity of the peptides in the nanoparticles. Herein, complexation was performed in water and the particles were further diluted using water before recording CD spectra. At an N/P ratio of 10:1, negative charge of miRNA was not enough to induce any significant folding of the Peptide 1 (MAX1) into a β-hairpin structure (FIG. 2C), even though a decrease in negative ellipticity around 200 nm compared to the soluble peptide was observed. Interestingly, decreasing N/P ratio promoted the evolution of a hairpin structure with a gradual increase in negative ellipticity values at 218 nm. Decreasing N/P ratio beyond 1:1 did not alter ellipticity values further, indicating complete degree of folding was already achieved (FIGS. 2C and 2D). Across these N/P ratios, a clear trend was observed between zeta potential values of complexes formed and folding behavior of Peptide 1. Surface charge of the complex increases with addition of more Peptide 1 with decrease in folding propensity of the peptide (FIG. 2D). As N/P ratio increases, more Peptide 1 is added into the complexation medium which reduces the amount of accessible negative charge to each individual Peptide 1 molecule causing a largely unfolded state of Peptide 1 on the surface of miRNA.

Figure 3A:
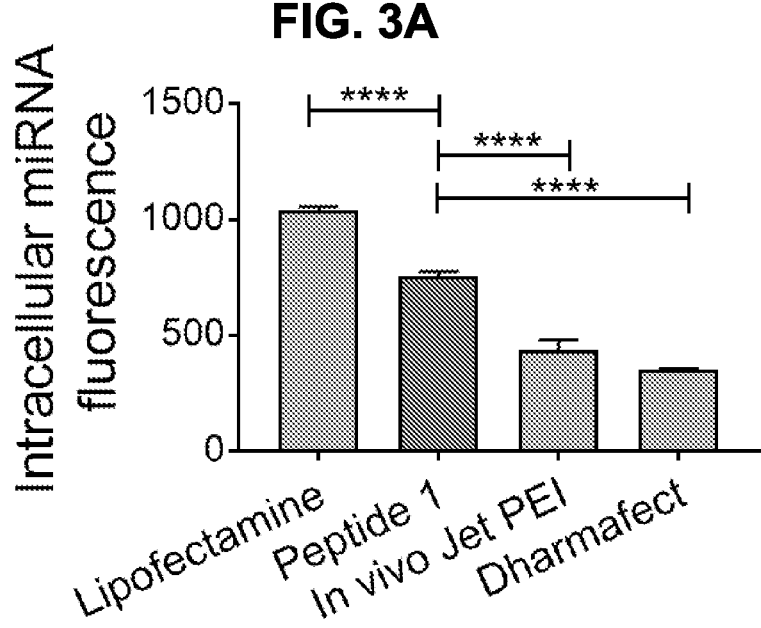
FIGS. 3A-3F. Cellular transfection and intracellular translocation of miRNA delivered via Peptide 1 in human mesothelioma cell line H2052.
Figure 3B:
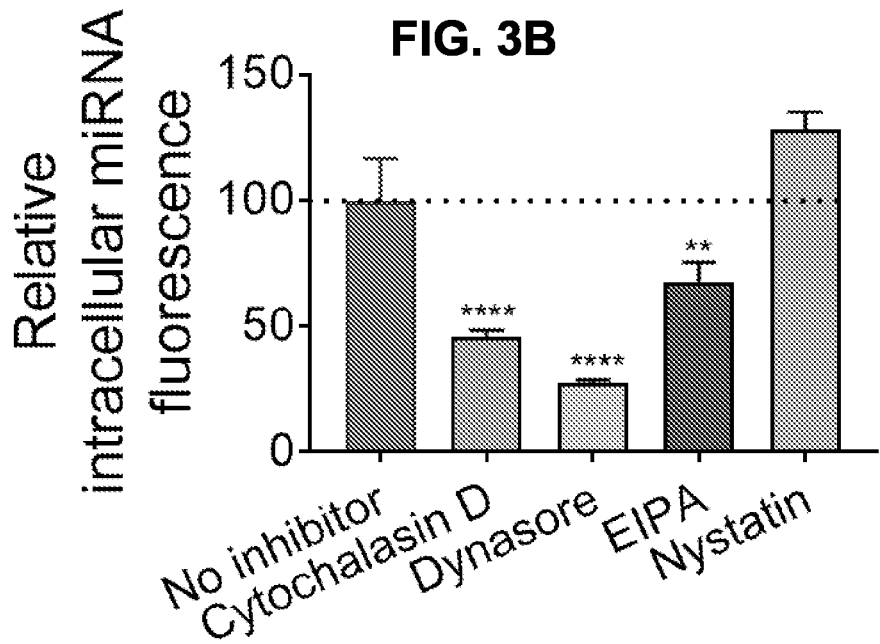
Figure 9B:
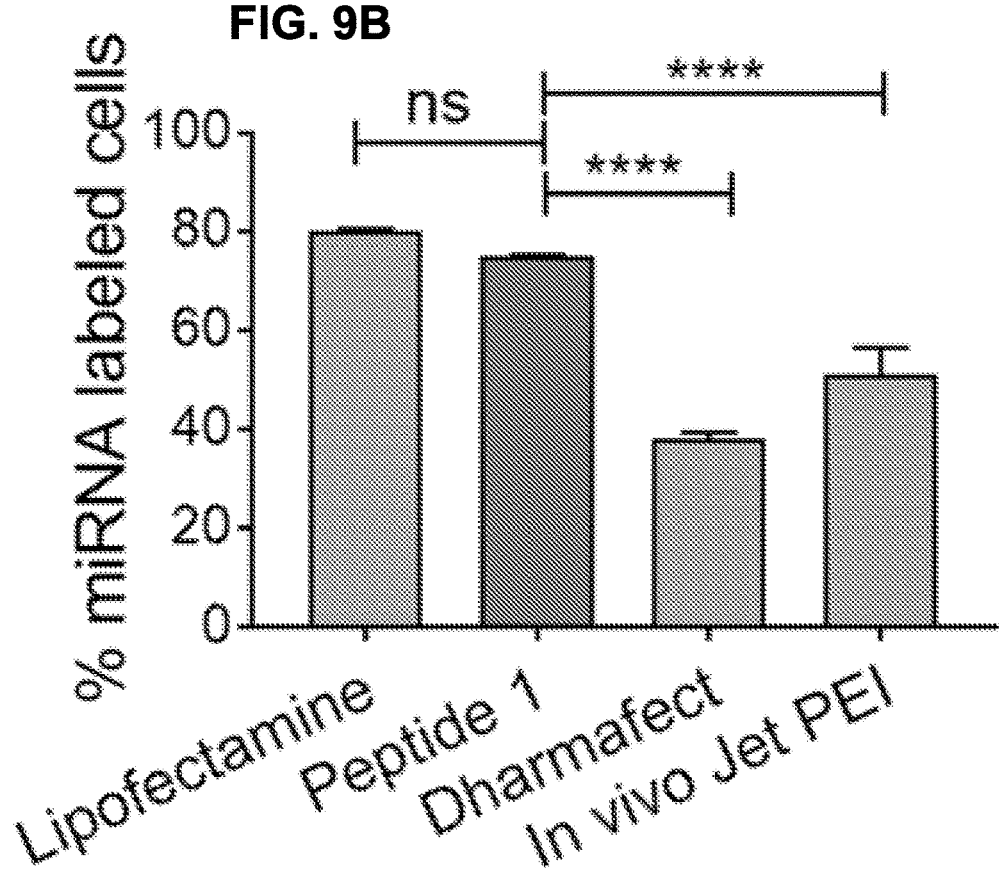
Figure 10A:
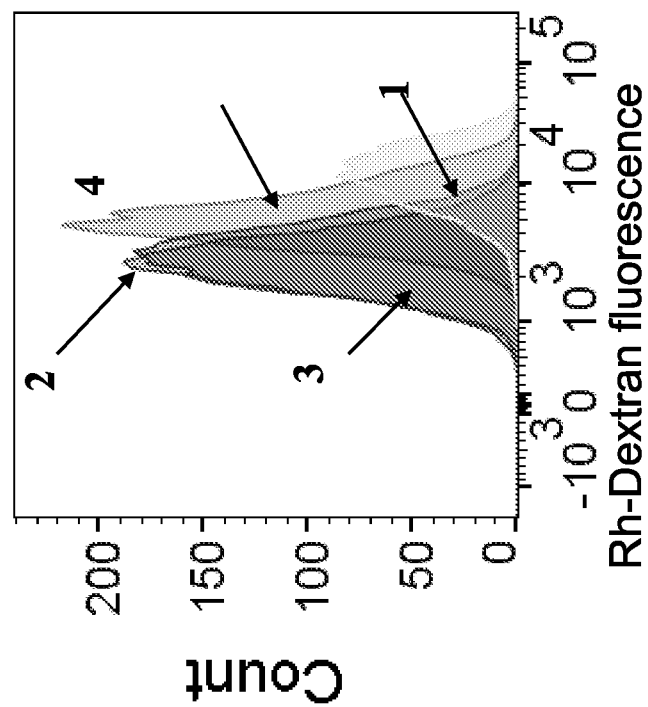
FIGS. 10A-10D. Determining the effect of chemical inhibitors on endocytic uptake of Transferrin and Dextran (70 kD), the markers for clathrin-dependent and macropinocytic pathways, in H2052 human mesothelioma cells. Flow cytometric histograms of cells treated with (FIG. 10A) Rhodamine-labeled Transferrin for 1 h in presence or absence of Cytochalasin D, Dynasore, EIPA and cells treated (FIG. 10B) with Rhodamine-labeled Transferrin for 1 h in presence or absence of Cytochalasin D, Dynasore, EIPA. Flow cytometric histograms of cells (FIG. 10C) treated with FITC-labeled Dextran and cells treated with FITC-labeled Dextran (FIG. 10D) for 1 h in presence or absence of Nystatin.
Figure 10B:
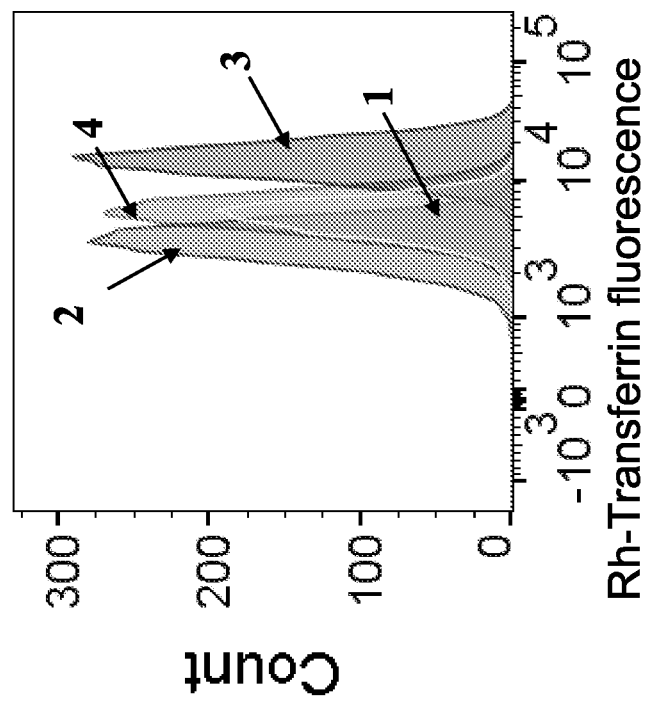
Figure 10D:
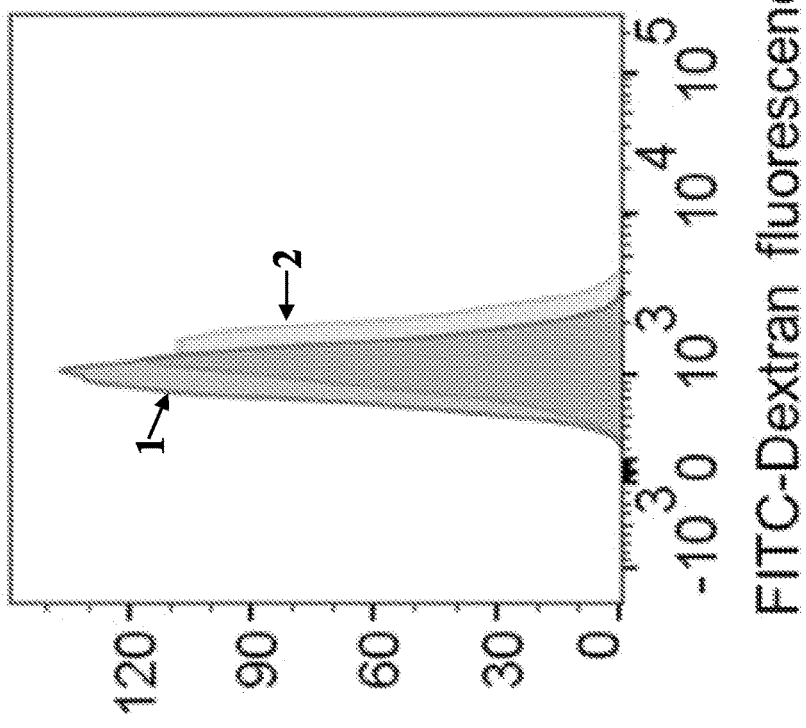
Figure 10C:
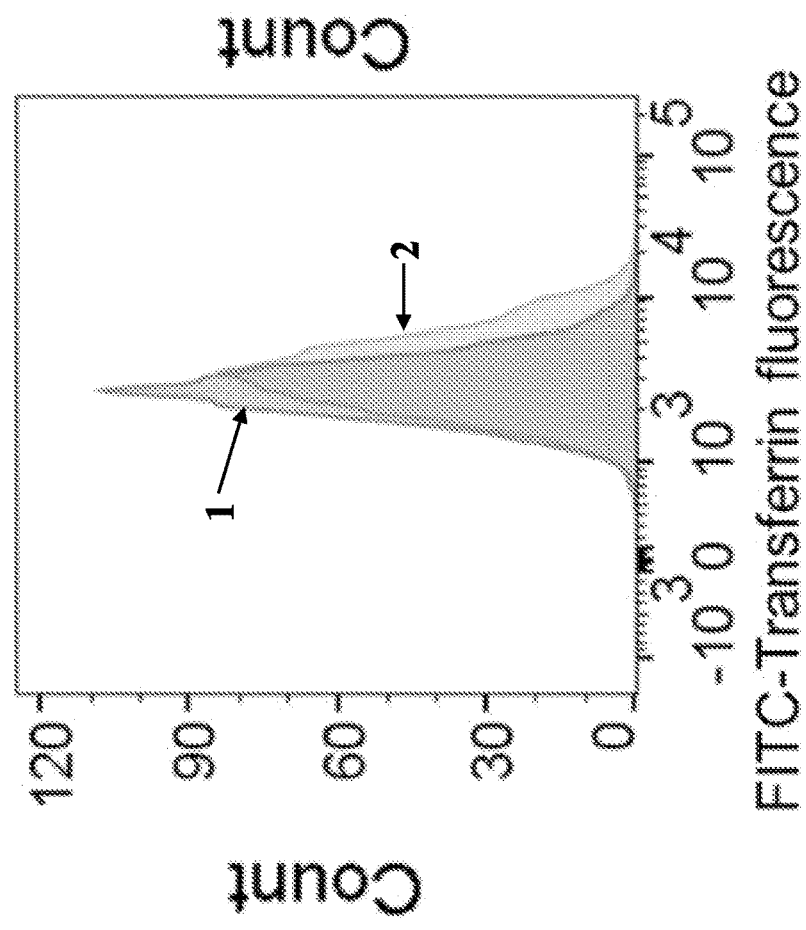
Figure 11C:
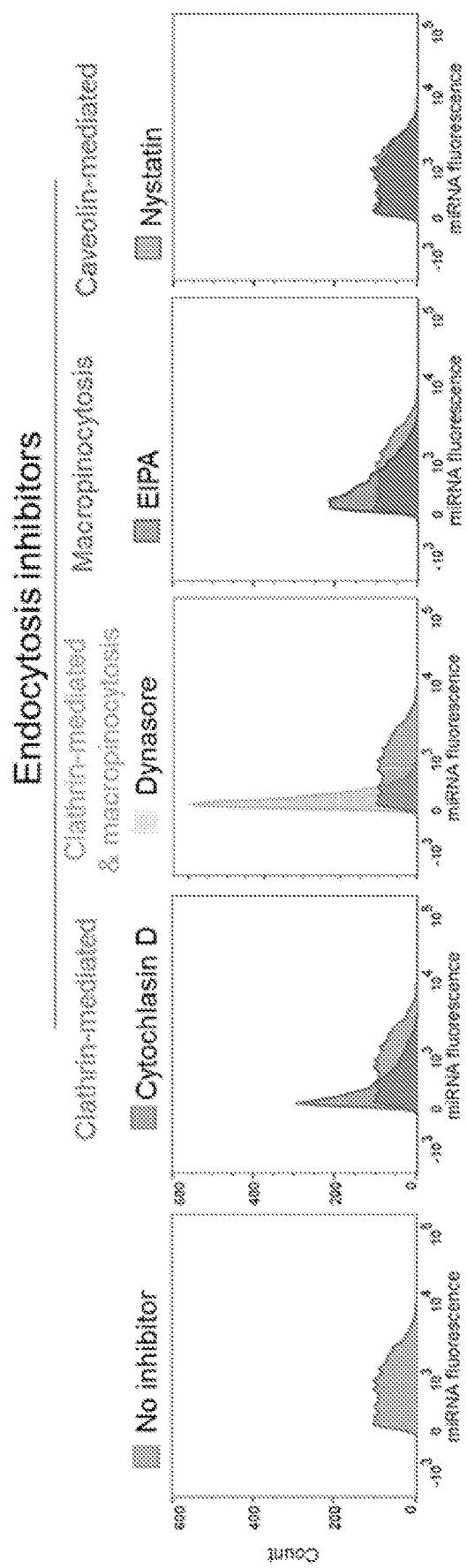

Ability of the peptides to intracellularly deliver miRNA into human mesothelioma cells H2052 (epithelioid subtype) was evaluated using FAM-labeled scrambled miRNA. When compared to the commercial transfection reagents, efficacy of the nanoparticles generated from Peptide 1/miRNA looked promising albeit slightly less than that for Lipofectamine (FIGS. 3A, 9A, 9B). To understand more into the mechanism of such miRNA transfection, the effect of chemical inhibitors of endocytic pathways on transfection efficacy was investigated using flow cytometry and confocal microscopy. EIPA was observed to be a selective inhibitor of micropinocytosis in H2052 cells while Cytochalasin D and Dynasore were considered as inhibitors for clathrin-dependent pathways (FIG. 10A-10D). Considering such mechanistic effects, MAX1/miRNA nanoparticles evidently internalized to H2052 cells predominantly through clathrin-dependent pathways as demonstrated by flow cytometric data (FIGS. 3B, 11A-11C).

Figure 3C:
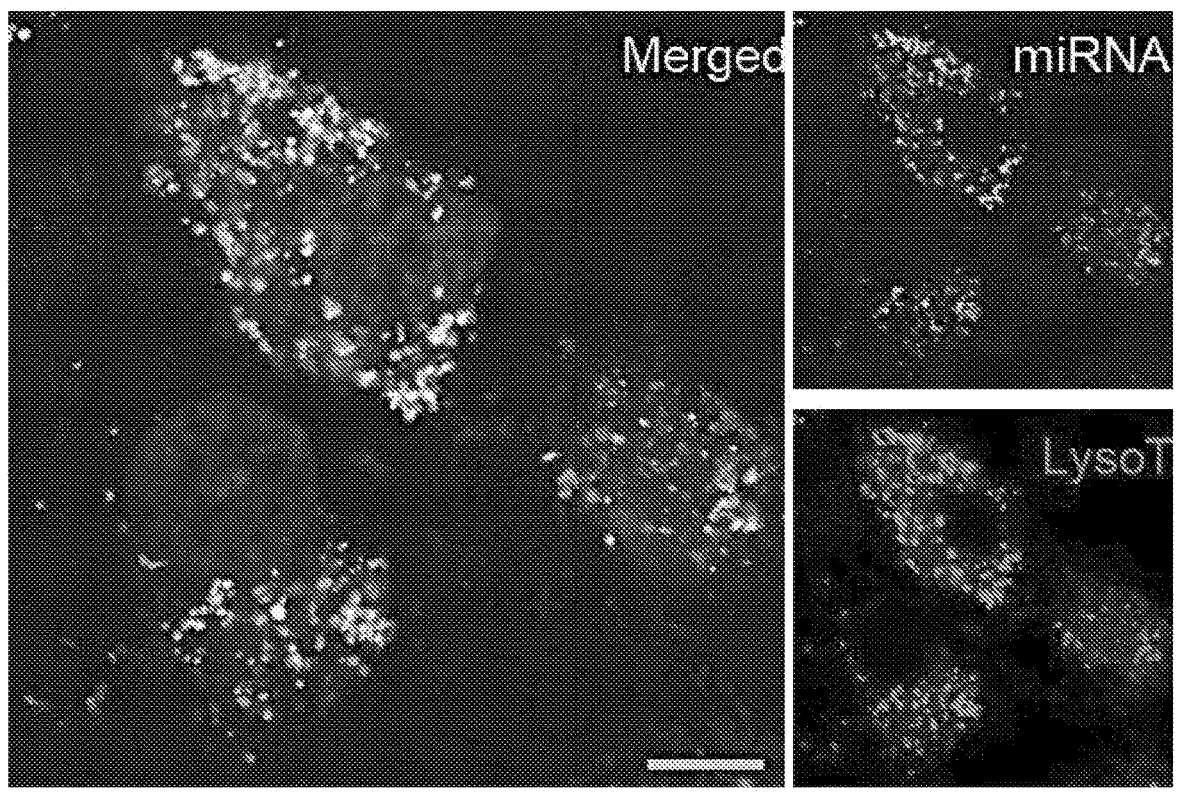
Figure 3D:
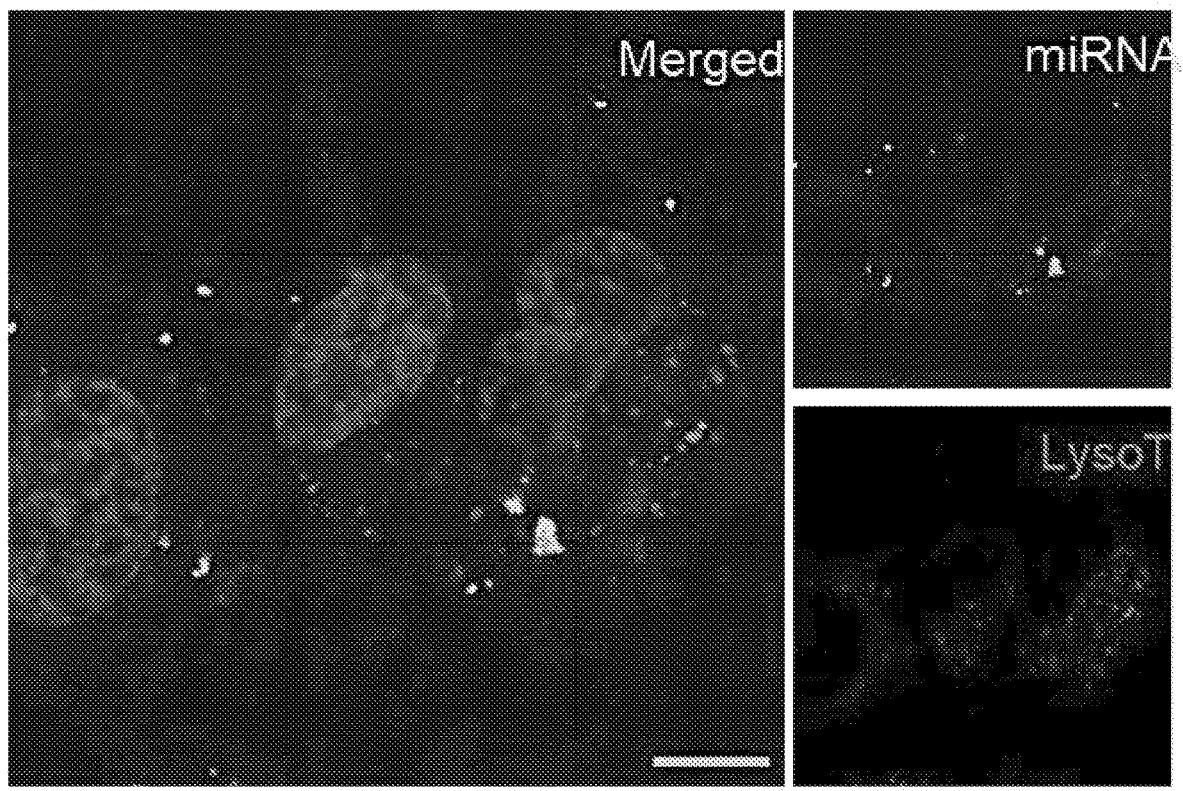
Figure 3E:
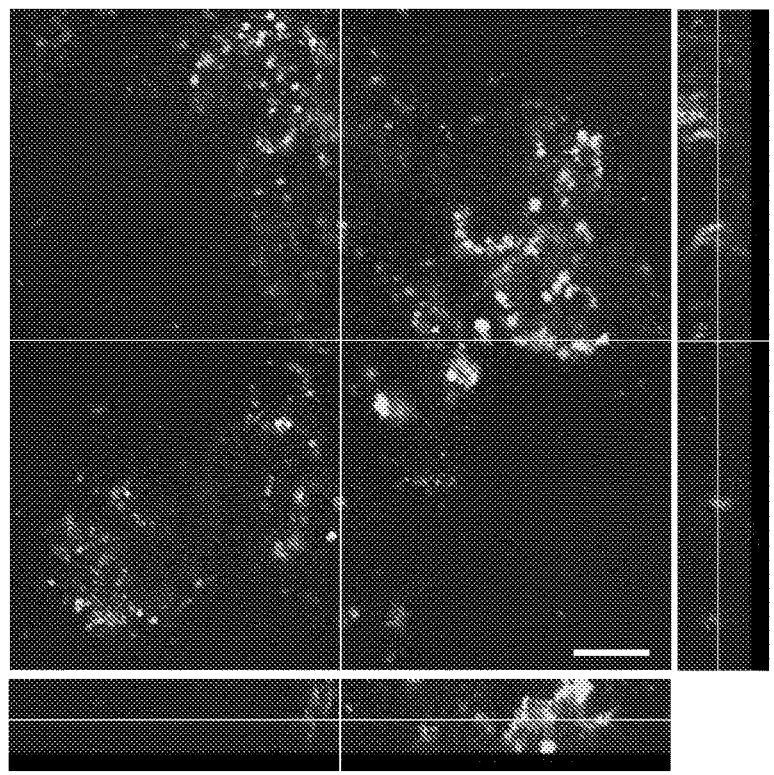
Figure 3F:
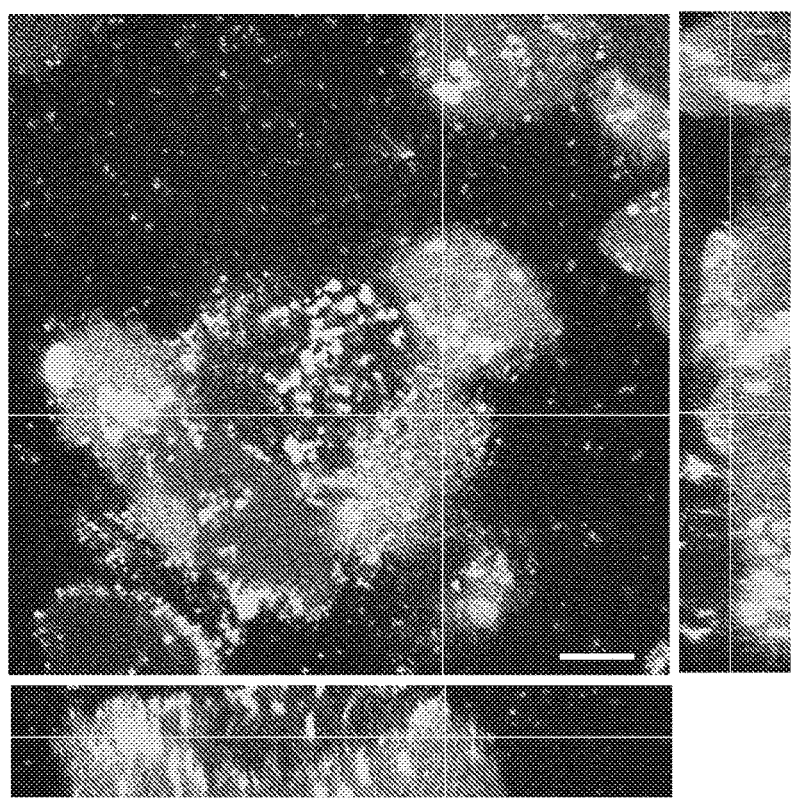
Figure 12A:
FIGS. 12A-12C. Intracellular distribution of Peptide 1/miRNA nanoparticles. Confocal microscopy image of live H2052 cells treated for 30 min (FIG. 12A) and 4 h (FIG. 12B) with nanoparticles containing cy3miRNA. Co-localization of cy3miRNA at each time point was determined for late endosome/lysosome marker lysotracker blue (LysoT).
Figure 12B:
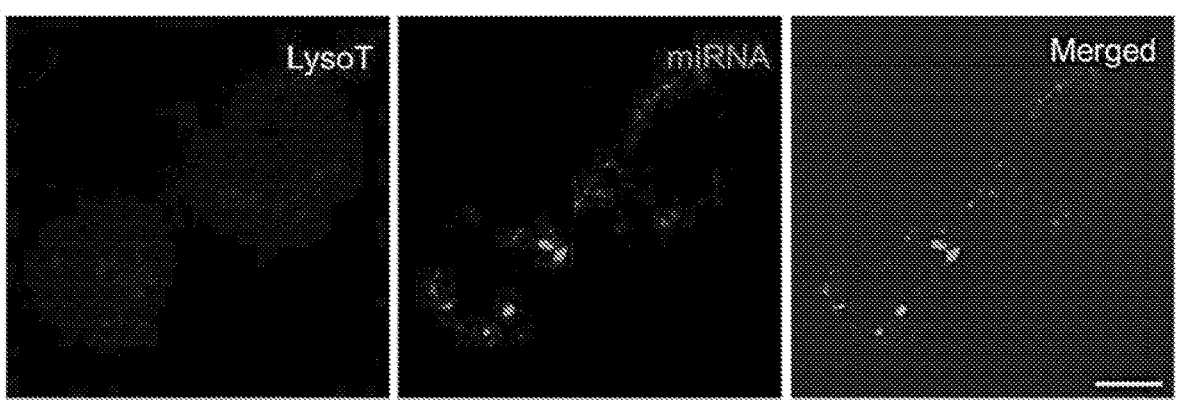
Figure 12C:
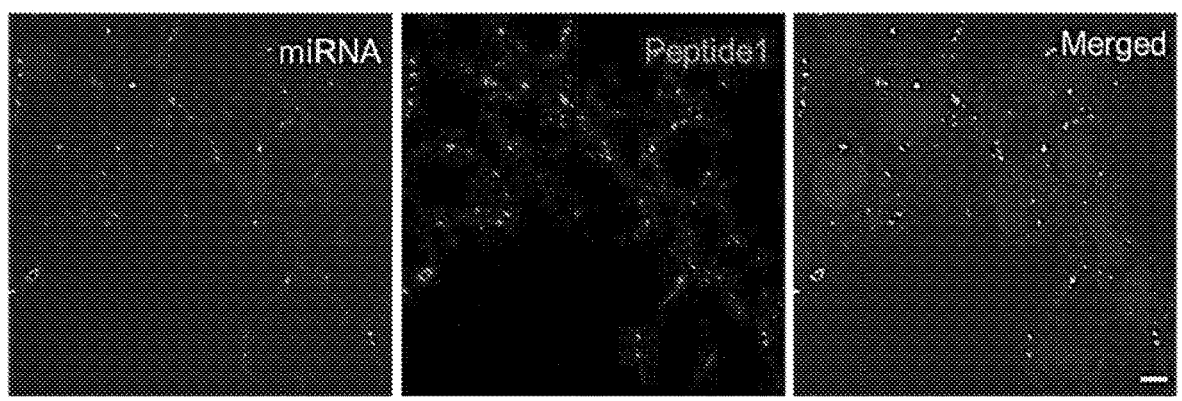

To understand the intracellular distribution of miRNA delivered using Peptide 1, confocal microscopy was performed on live H2052 cells. Co-localization studies were performed using lysotracker to assess sub-cellular localization of miRNAs. Images acquired at 30 min post-incubation with the nanoparticles indicated that internalized miRNAs (FAM) predominantly stayed localized in acidic endosomal compartments as evidenced via merged fluorescence (FIG. 3C). Interestingly, a clear separation was observed between labels at 4 h post-incubation, indicating miRNAs have been able to escape the endosomes (FIG. 3D). Notably, at 4 h, degree of Lysotracker staining was considerably decreased which possibly indicates partly endosomolytic behavior of the nanoparticles. In agreement with this, calcein release studies shown in FIGS. 3E-3F validate that co-incubation with nanoparticles facilitates release of calcein from the endosomes to access the cytoplasm (punctate fluorescence localized to endosome in FIG. 3E spills into the cytoplasm in FIG. 3F). A similar result was observed when cells were incubated with cy3-labeled miRNA and their colocalization was tracked with Lysotracker Blue (FIGS. 12A-12B). FIG. 12C demonstrates that miRNA payloads stay localized with the corresponding peptides when the cells were incubated with dually labeled nanoparticles for 4 h.

Figure 4A:
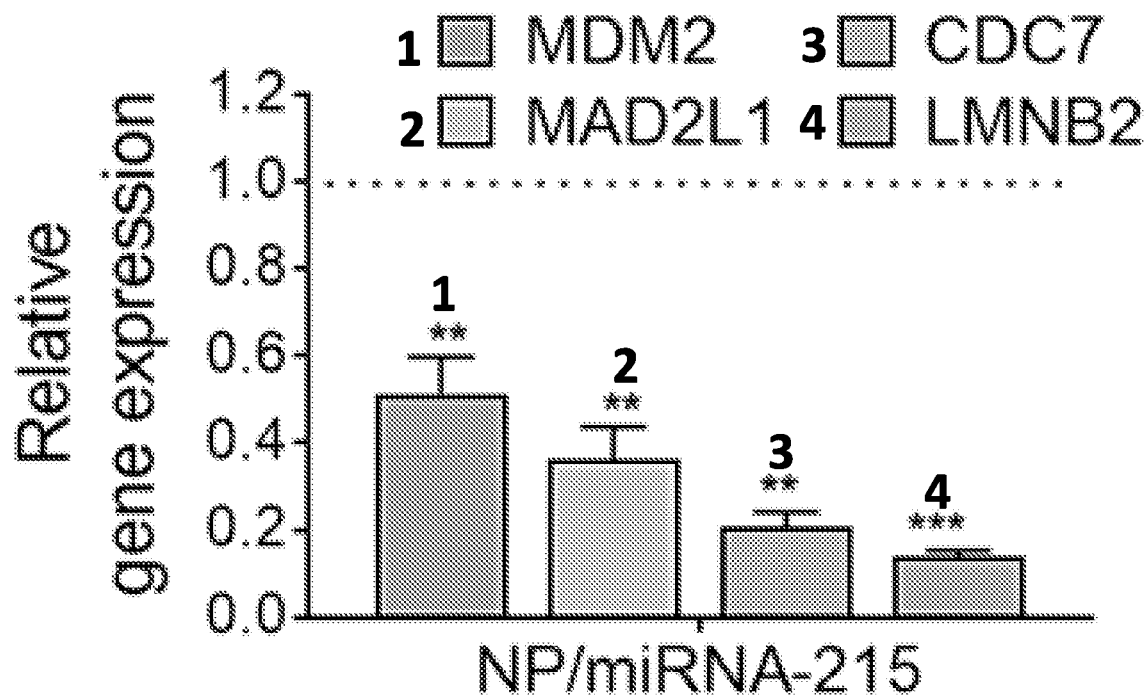
Figure 13A:
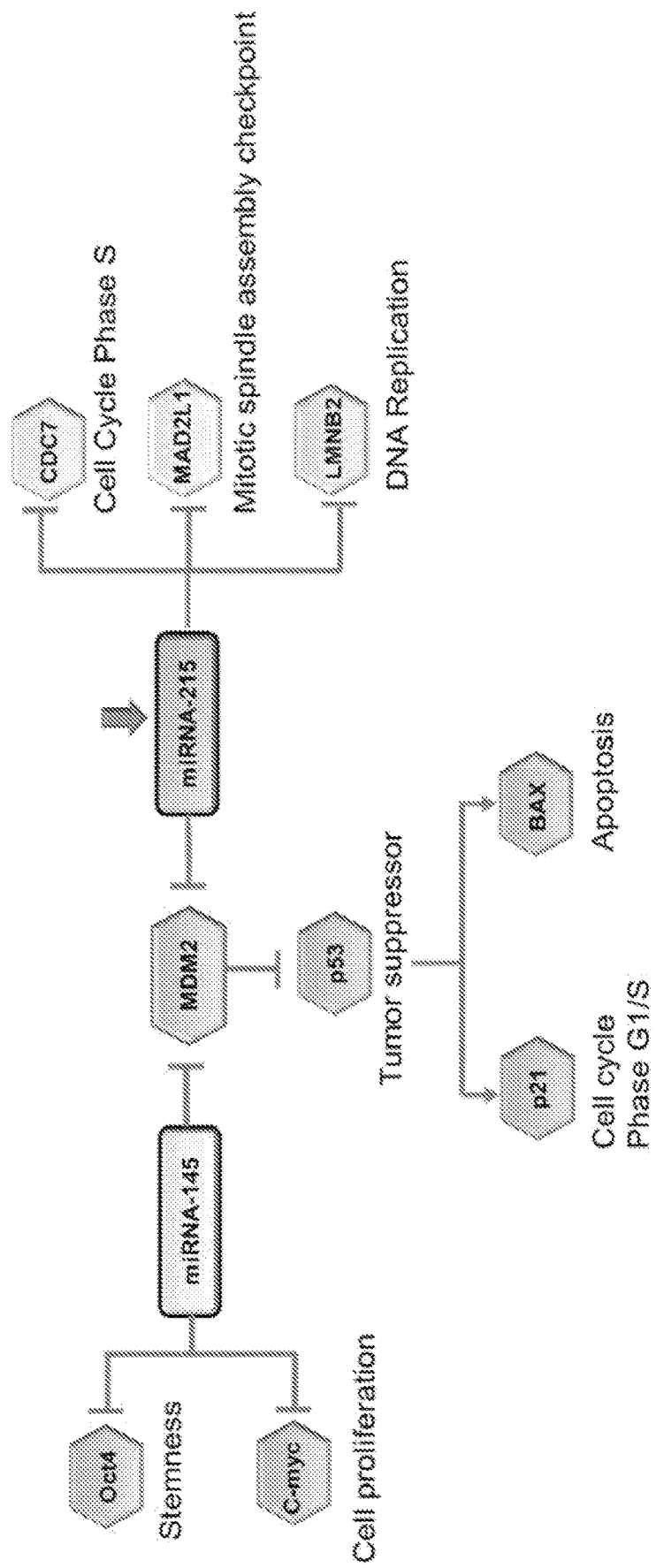
FIGS. 13A-13C.

To investigate the implications of such distinct intracellular miRNA distribution pattern on the therapeutic efficacy of the delivered payload, Peptide 1 was used to deliver miR-215 into H2052 cells in vitro. In vitro transfection of miR-215-5p into mesothelioma cells has been shown to mitigate cellular proliferation by inducing apoptosis via silencing MDM2, the main regulator of p53, as well as silencing multiple cell cycle-associated genes, e.g. CDC7, LMNB2, and MAD2L1 (FIG. 13A). Consistently, nanoparticles delivering miR-215-5p significantly silenced these same target genes as observed at the transcript level with qPCR (FIG. 4A).

Figure 13C:
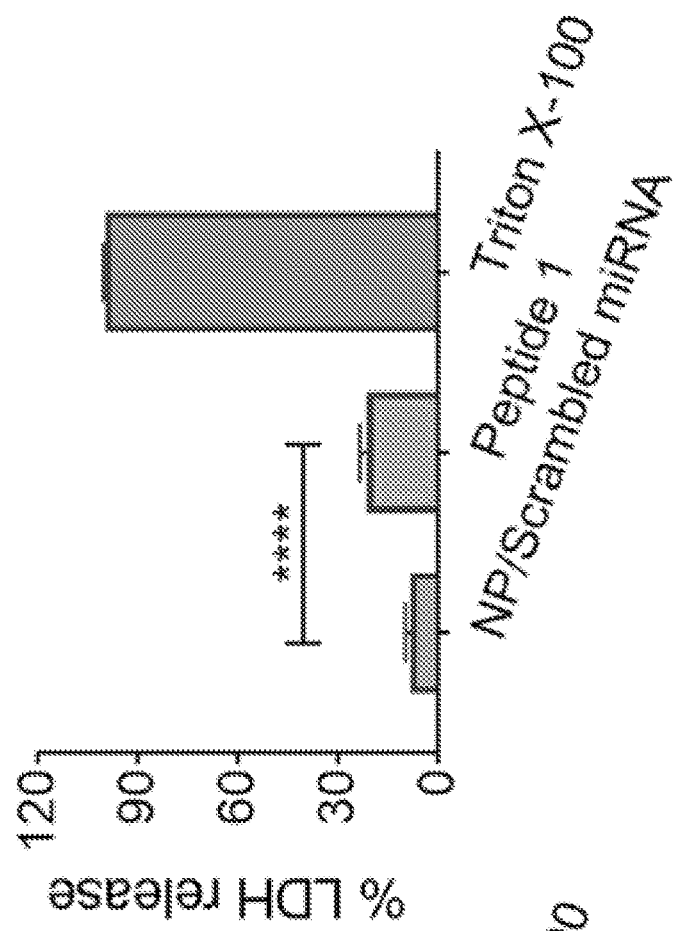
Figure 13B:
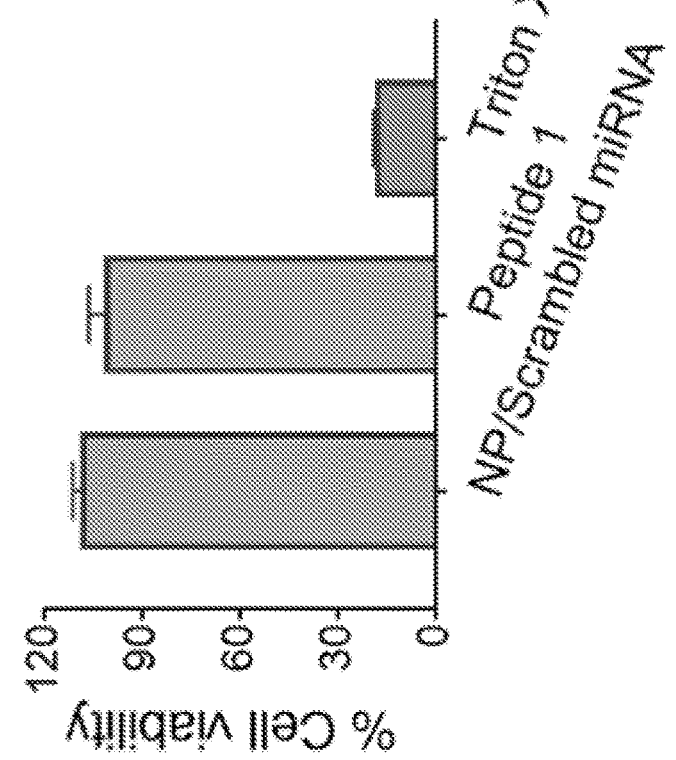

To evaluate any possible contribution of cytotoxicity of the nanoparticles towards non-specific gene silencing, cell viability and cytotoxicity parameters were assessed using MTT (FIG. 13B) and LDH assays (FIG. 13C), 4 h post-transfection, duration for which the nanoparticles are incubated with cells. Though the soluble peptide was found to have 20% cytotoxicity as compared to the positive control Triton X-100, complexation with miRNA resulted in a completely cytocompatible nanoparticle due to screening of lysine-borne positive charges (FIG. 13C).

Figure 4B:
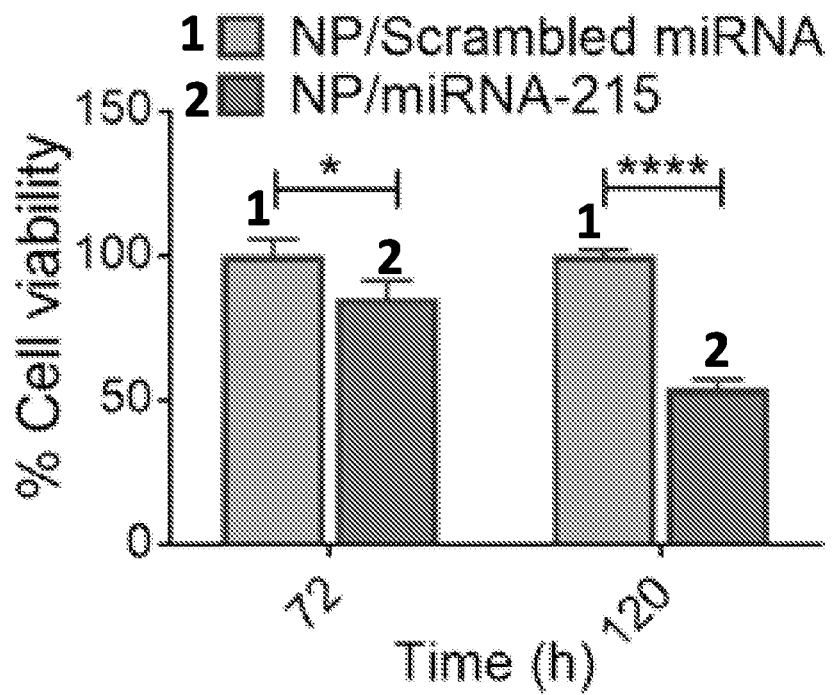
Figure 4C:
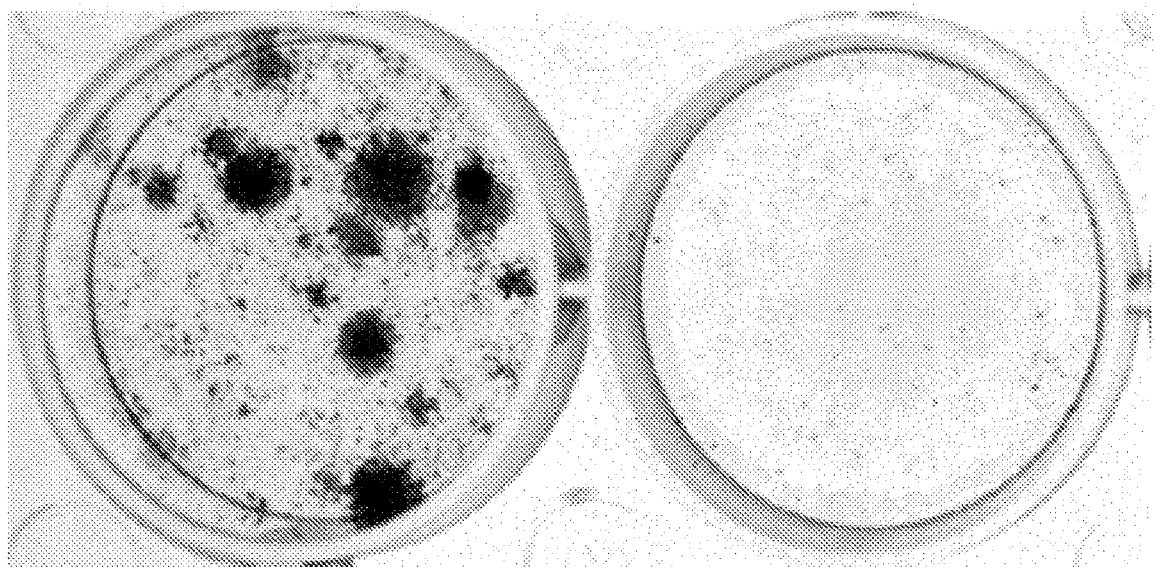
Figure 4D:
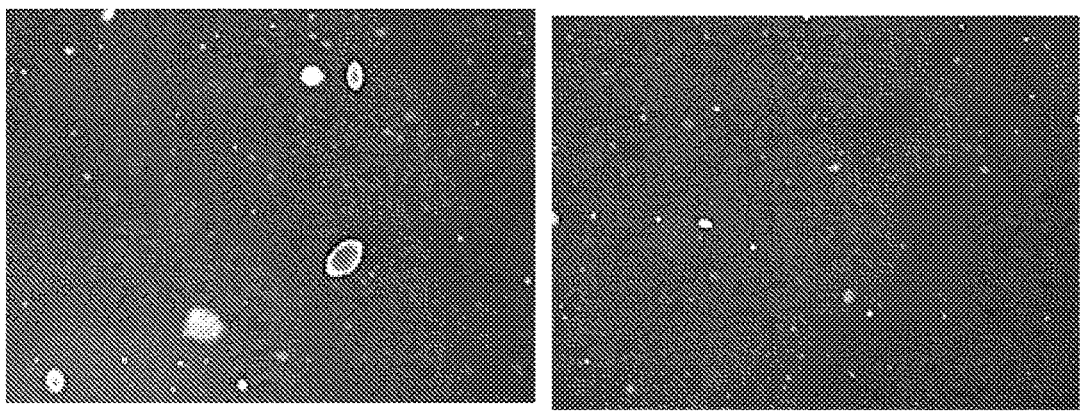
Figure 4D:
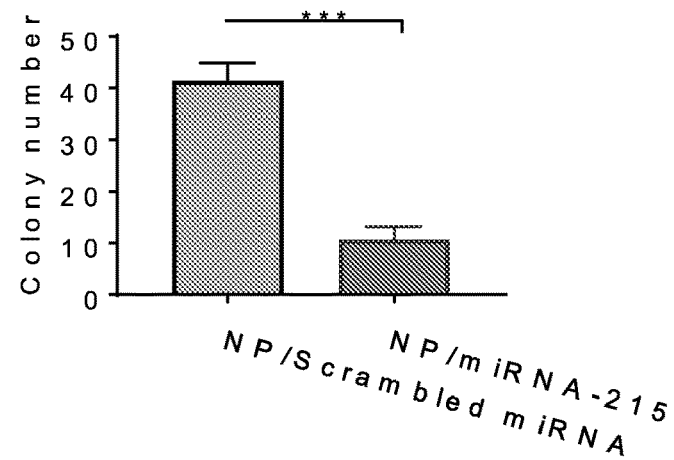
Figure 14:
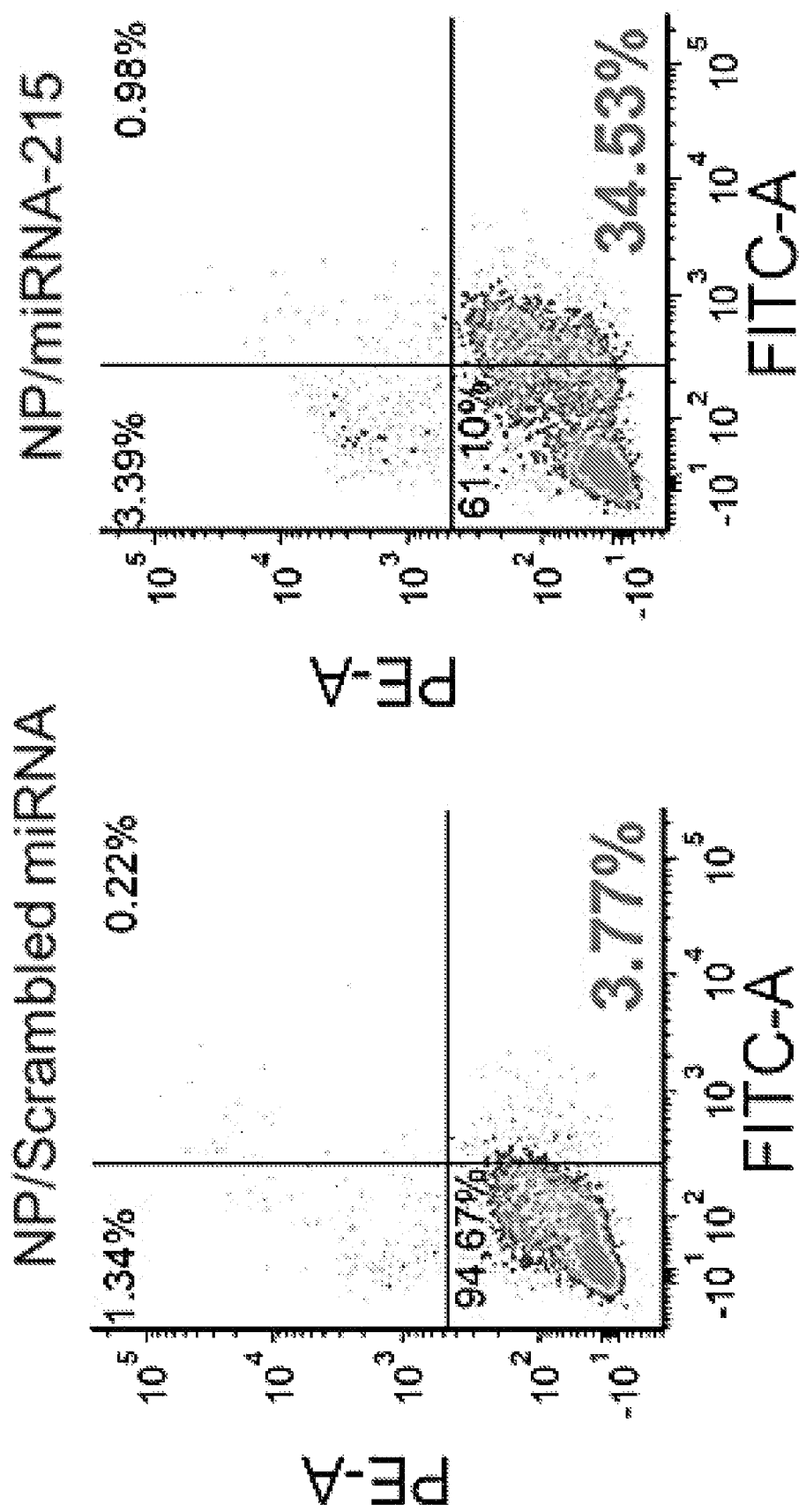
FIG. 14. Flow cytometric Annexin V-FITC/PI staining profiles of H2052 cells treated with nanoparticles composed of Peptide 1 and miRNA 96 h post-treatment indicating the extent of apoptosis induced.

Gene silencing efficacy of an equivalent Lipofectamine complex are described in FIGS. 14A-14B. Gene-silencing capacity of nanoparticles were found to be slightly better than that for Lipofectamine (FIG. 14A). Lipofectamine with its well-accounted toxicity altered cell-morphology 48 h post-incubation when treated into cells as complexed with scrambled miRNA (FIG. 14B). The potent gene-silencing effect resulted in a drastic drop in proliferative capacity of the cells. MTT assay results at 72 h and 120 h post-exposure (4 h direct incubation followed by chase) indicated a reduced cell-proliferation with 50% decrease in viability (FIG. 4B) for cells treated with nanoparticles bearing miR-215-5p. There was also a substantial drop in clonogenic potential of treated cells, as shown in 2D colony formation assay (FIG. 4C) and a significant reduction in anchorage-independent growth of H2052 cells (FIG. 4D). It was also observed that miR-215-treated cells lost their viability by increased apoptosis (FIGS. 4E and 14C).

Figure 15A:
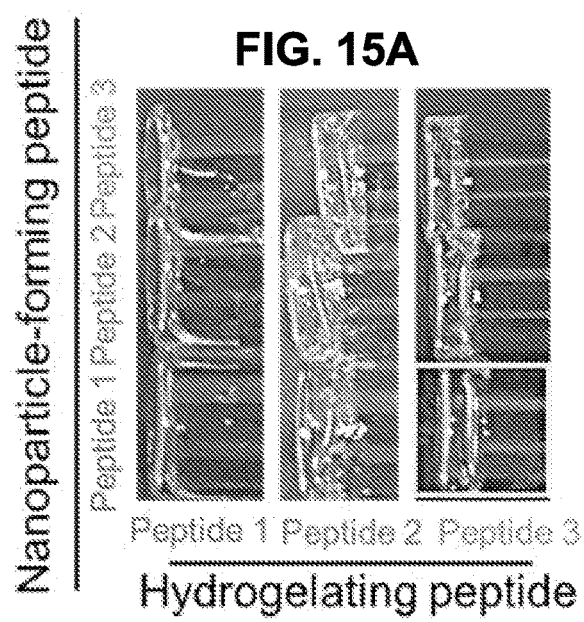
FIGS. 15A-15E. Biophysical characterization of hydrogel composites.
Figure 15B:
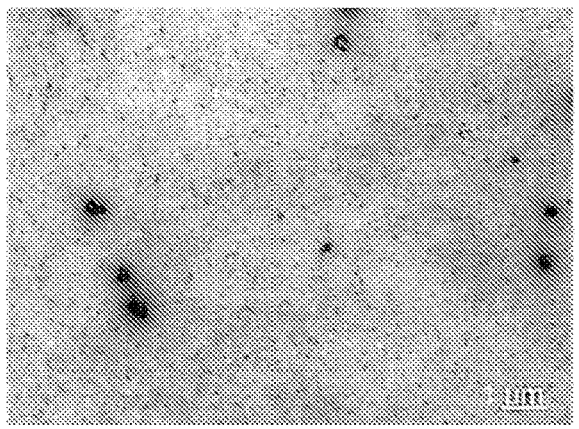
Figure 15C:
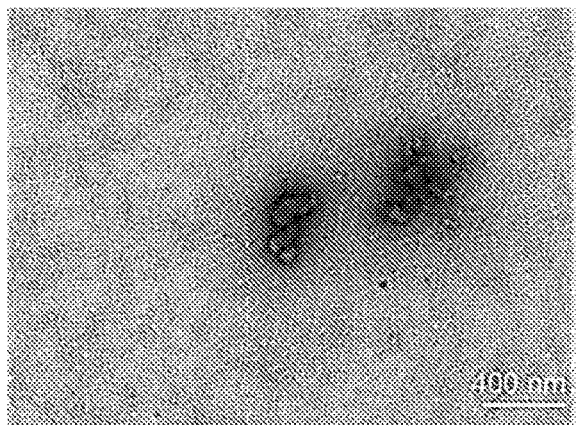
Figure 15D:
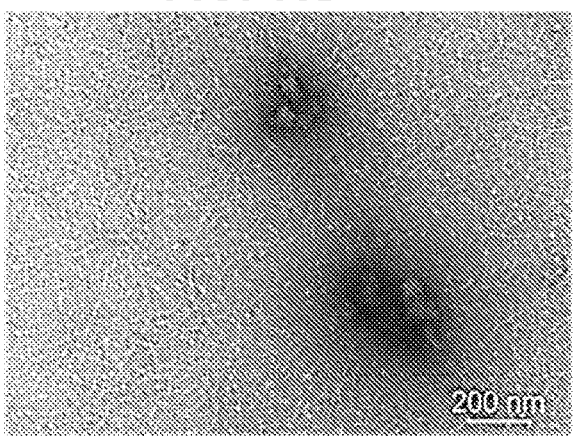
Figure 15E:
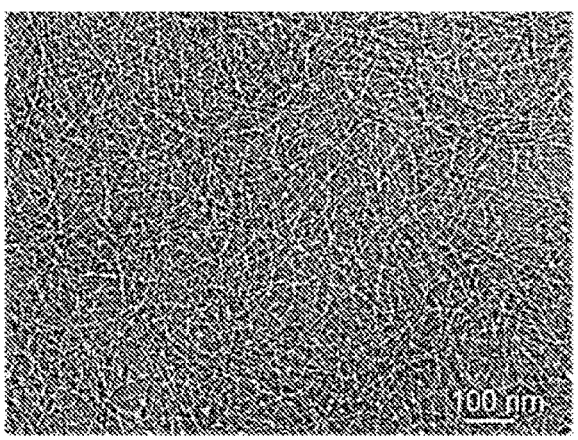

Recognizing the biophysical and cellular behavior of the nanoparticles (miRNA bound to disordered peptides), they were utilized in designing a local miRNA delivery system via engineering a composite hydrogel material. The gels were obtained by encapsulating the nanoparticles into a fibrillar network formed via a set of self-assembling β-hairpin peptides. First, the particles were encapsulates in hydrogel network constituted with Peptide 1, Peptide 2 and Peptide 3 (FIG. 15A). The hydrogelating peptide is first dissolved in low ionic strength buffer where the peptide stays in a random structure. Once mixed with the nanoparticle suspension (osmolarity adjusted to physiological condition), salt ions present in the medium cause the peptide to fold into a β-hairpin structure, followed by self-assembly into the hydrogel composite where nanoparticles stay uniformly distributed throughout the fibrillar network. Structure of the hydrogel composite formed via self-assembling Peptide 3 is shown in FIGS. 4F and 15B-15D. Nanoparticles are clearly observed here in addition to the fibrillar network of properly folded and self-assembled Peptide 3. TEM images of blank Peptide 3 hydrogel as a control is shown in FIG. 15E.

Figure 16A:
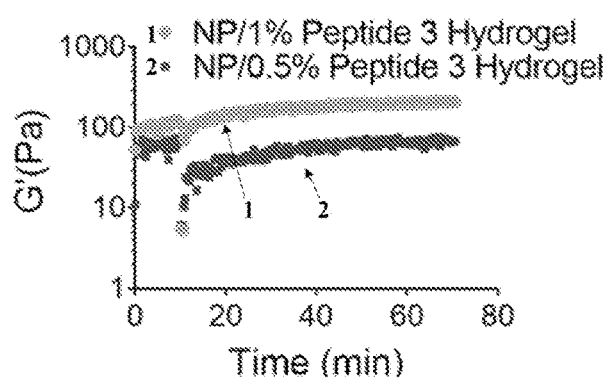
FIGS. 16A-16F. Hydrogel composites are shear-thin injectable and can release encapsulated nanoparticles slowly overtime.
Figure 16B:
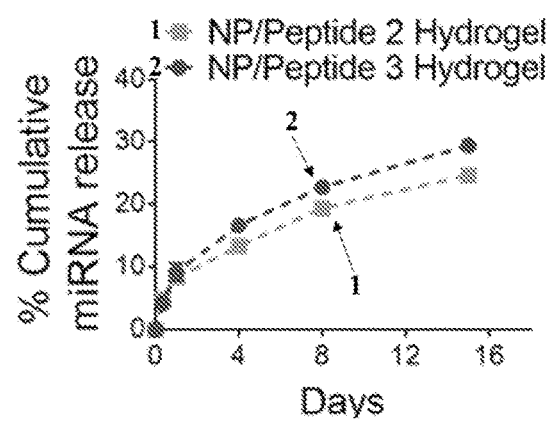

To understand more about the gel network characteristics, oscillatory rheology was performed on Peptide 3 gel composites (FIG. 16A). Gels were formed for 24 h in transwell inserts and transferred onto the rheometer plate. For the first 10 minutes, the storage moduli (G') is monitored as a function of time. In the next phase, the gels are shear-thinned and allowed to recover, applying similar conditions to what the gels are subjected to during in vivo administration via syringe injection. Both gel composites quickly recover after shear-thinning while 1% Peptide 3 gel reaches a final storage modulus of 212 Pa. As shown in FIG. 16B, release profiles of miRNA are compared between hydrogel composites consisting of Peptide 2 and Peptide 3, each used at 0.5% (w/v). Accounting for almost similar release profiles, Peptide 3 hydrogel composites were used for the subsequent experiments. The Peptide 3 hydrogel composite showed a shear-thinning and recovery property indicating the feasibility of these gels for syringe injection.

Figure 16C:
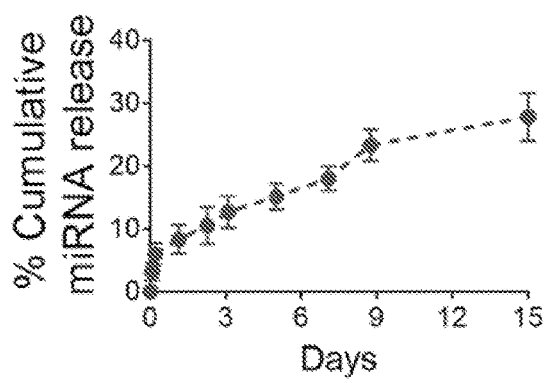
Figure 16D:
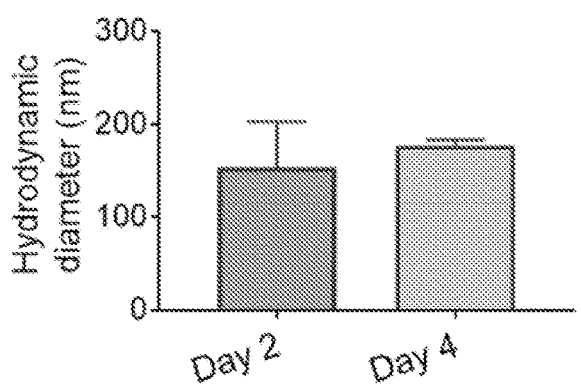

FIGS. 4G and 16B-16C show results of assays for monitoring the release of nanoparticles from Peptide 2 and Peptide 3 hydrogel composites. Supernatant from each hydrogel is isolated as a function of time and dissociated with heparin to release free miRNA, whose fluorescence is measured. As shown in FIG. 4G, Peptide 3 hydrogel composites containing 0.5% (w/v) Peptide 3 as the hydrogelating peptide released ~25-30% of the total encapsulated miRNA over a period of 10 days. Release rate could be even slower when mesh size of the hydrogel matrix is reduced upon using 1% (w/v) of Peptide 3.

Figure 16F:
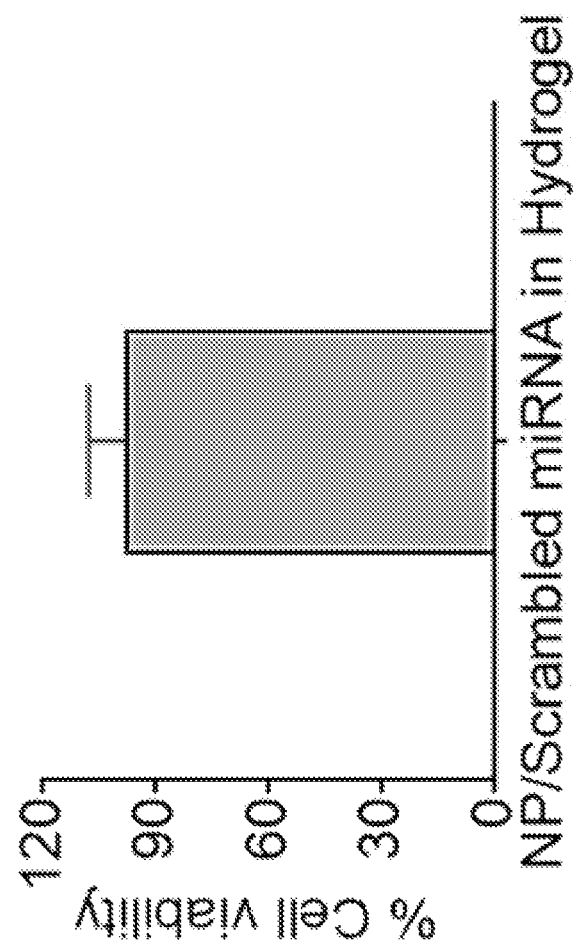
Figure 16E:
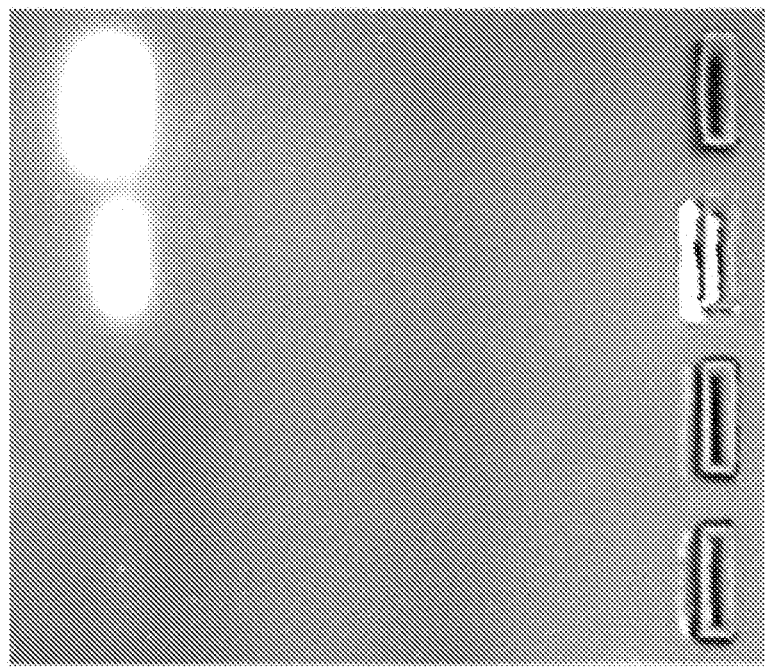

An agarose gel electrophoresis assay was performed to visualize the electrophoretic mobility of miRNA present in the release supernatant as compared to those for free miRNA and miRNA present in the nanoparticle before loading into the gel assembly. Freshly prepared nanoparticles containing 1 µg of loaded miRNA show two distinct bands in a 2% agarose gel (FIG. 16E). The band possessing similar mobility to that for naked miRNA might indicate presence of complexes of low molecular weight that might have been dissociated in the electric field. As demonstrated in fluorescence-based binding experiment (FIG. 2A), saturation in degree of fluorescence quenching for miRNA bound to the peptides at 10:1 N/P ratio, rules out possibility of having naked miRNA. Similar pattern was also evident for the release media collected at day 2 and day 4. Low intensity of the bands understandably indicates minute number of nanoparticles released from the gels.

Figure 4H:
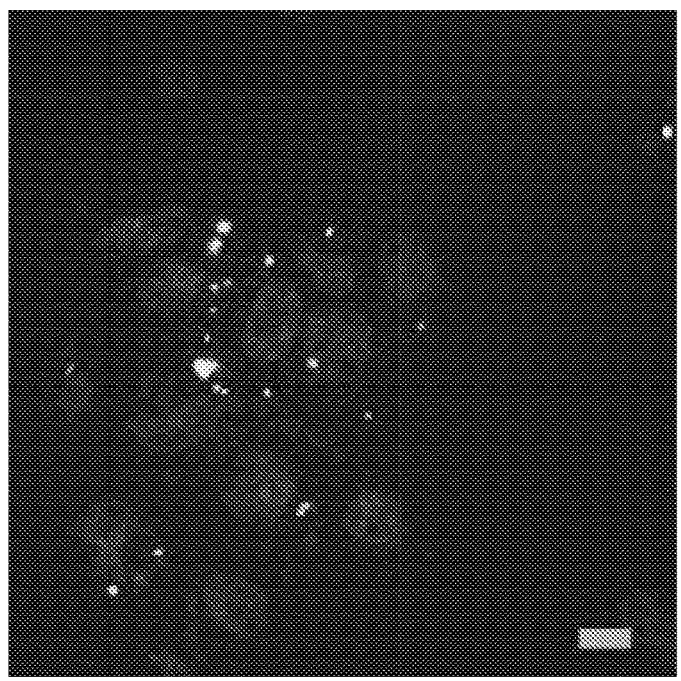
Figure 4I:
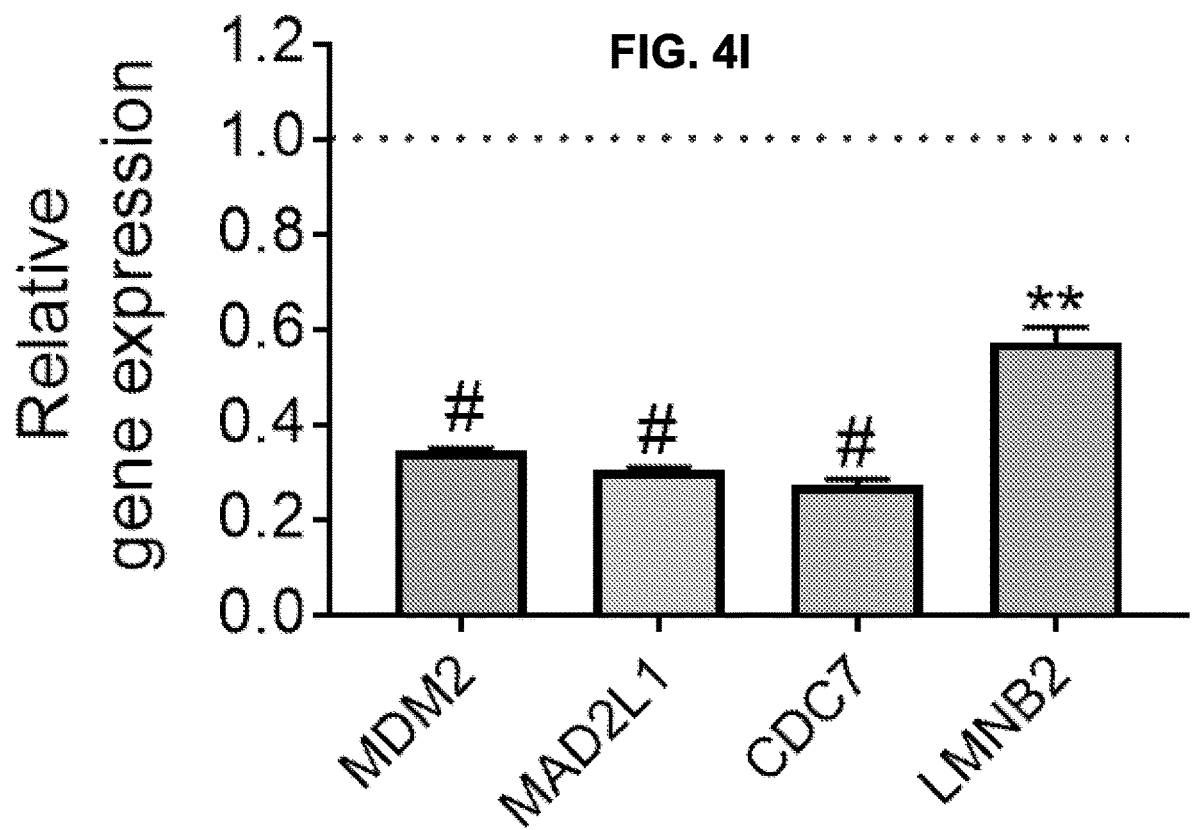

Encapsulation in the gel network does not cause the nanoparticles to lose their potential for miRNA transfection and gene silencing. FIG. 4H indicates that nanoparticles released from gel are as equally potent as their native counterpart to deliver miRNA intracellularly, which is evident from fluorescence of transfected FAM-miRNA. Similarly, gels loaded with miR-215-5p also release functional nanoparticles which stay active to silence all its target genes (FIG. 4I). These nanocomposite gels are cytocompatible (see FIG. 16F).

Figure 17A:
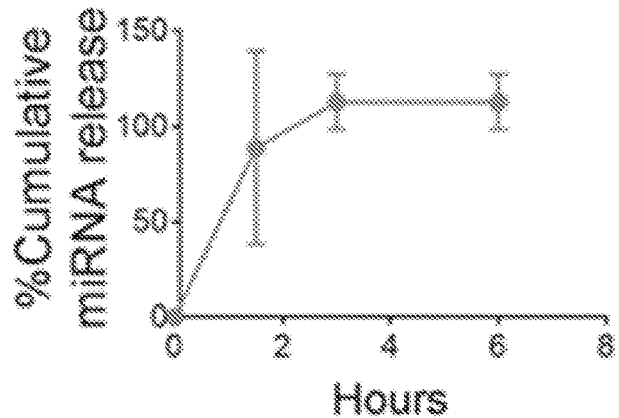
FIGS. 17A-17C. Nanoparticles consisting of Peptide 1 and miRNA when encapsulated within self-assembling β-hairpin Peptide 4-based hydrogels (with net negative charge of 5 per peptide molecule) releases in a burst and cannot functionally deliver miRNA into H2052 cells in vitro.
Figure 17B:
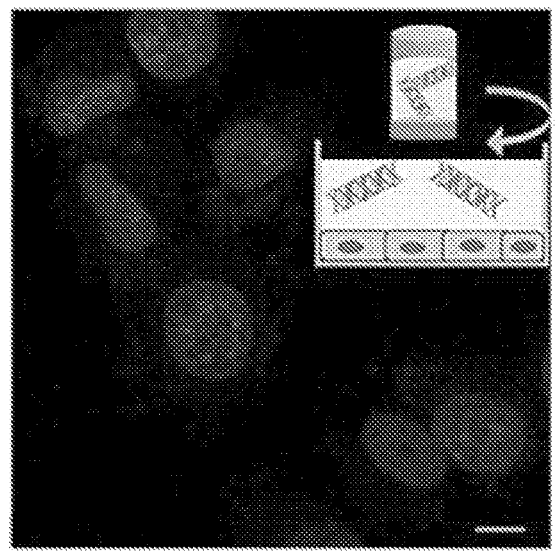
Figure 17C:
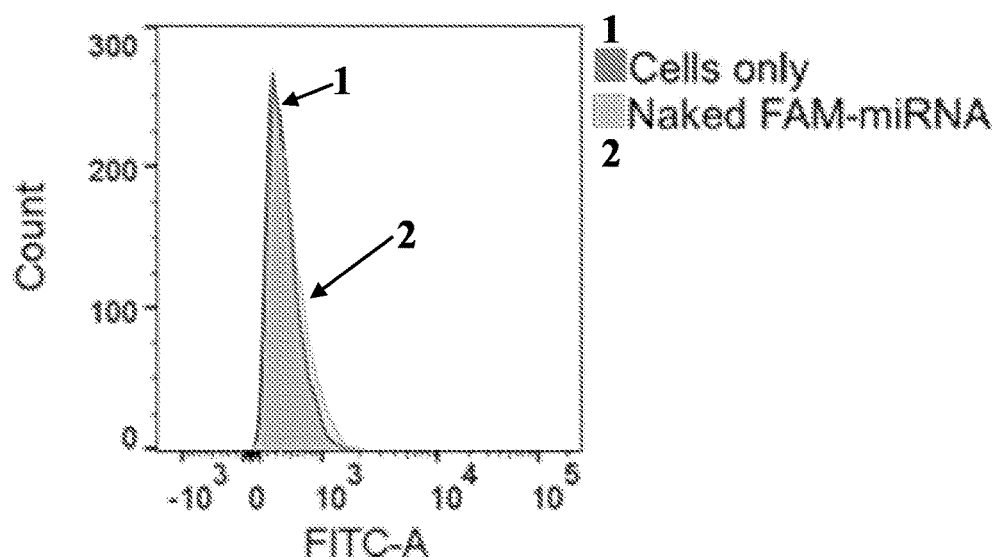

Interestingly, miRNA release from the gel composites is dictated by a competitive interaction between the hydrogelating peptide in the matrix and the peptide used to compose the nanoparticles. When a self-assembling peptide, Peptide 4 possessing 5 negative charge per monomer (at physiological pH) and the four residue β-turn -V$^D$PPT- was used to constitute the gel composites, miRNA was released rapidly within hours and the resulting gel was essentially incompetent to transfect miRNA (FIG. 17). Thus, Peptide 1:RNA nanoparticles encapsulated in the Peptide 4 gel network are unstable. The cationic Peptide 1-RNA complex rapidly dissociates, and the cationic Peptide 1 binds avidly to the anionic Peptide 4 gel network. This results in the release of free naked RNA from the hydrogel, which is unable to enter cells. In contrast, Peptide 3 hydrogel composites can stably encapsulate and slowly release functional nanoparticles for effective gene silencing in vitro (FIGS. 4F-4I, and 16-17).

Figure 18A:
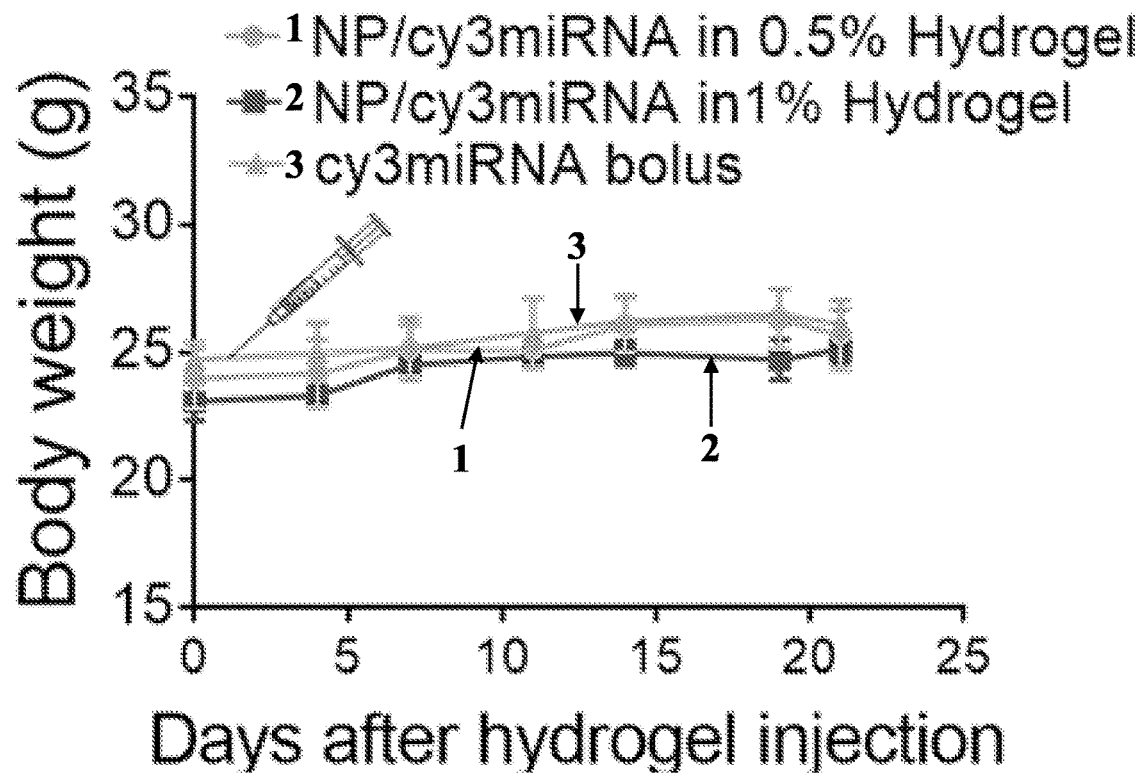
FIGS. 18A-18B. Measurement of body weight of mice as an indicator of cytocompatibility of hydrogel composite formulations.
Figure 18B:
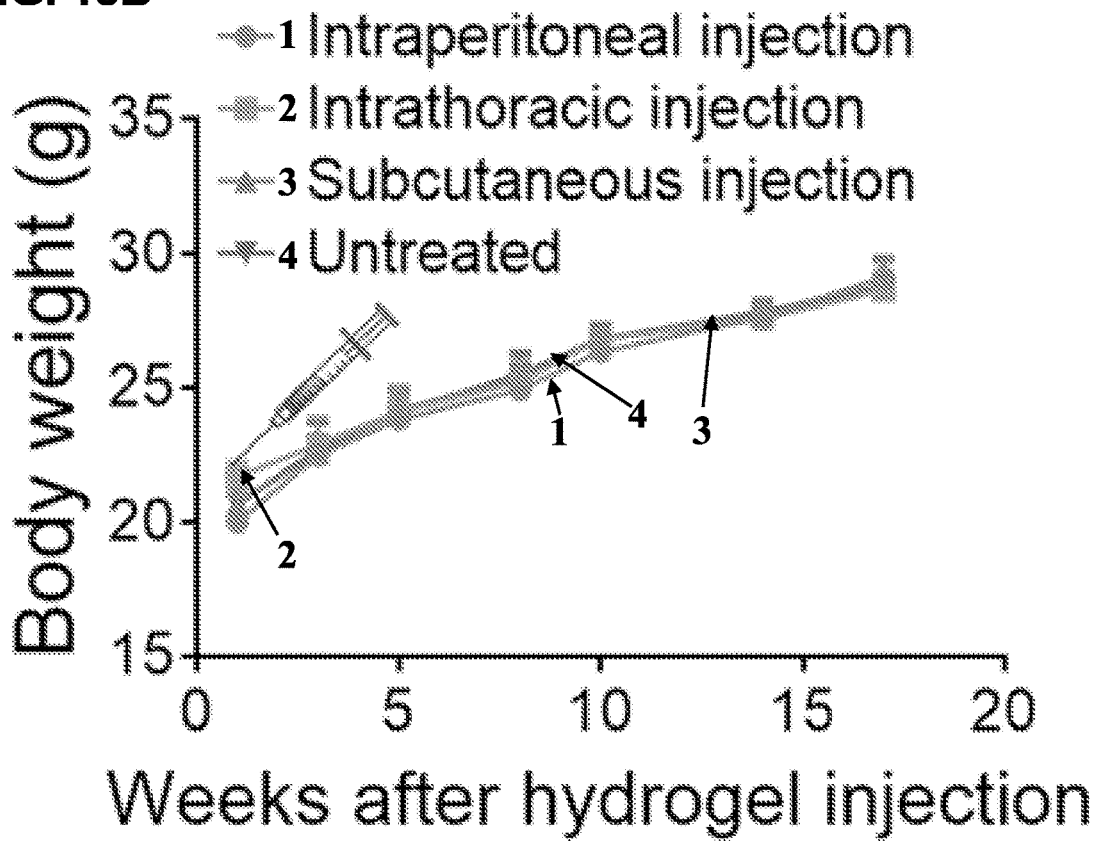

Efficacy of the hydrogel composites in cellulo prompted investigation of whether the gels can sustain the delivery of miRNA in vivo. As shown in FIG. 18, the gels are biocompatible in vivo. Body weights of mice receiving hydrogel composites were monitored to understand safety profiles of the designed material. As shown in FIG. 18A, there was no difference in body weights among mice receiving different hydrogel composites with encapsulated cy3miRNA and those injected with miRNA bolus dose. Similarly, hydrogel composites of scrambled miRNA administered via subcutaneous, thoracic and intraperitoneal modes did not affect body weights of mice (FIG. 18B), indicating no apparent systemic toxicity of the gel composites.

Figure 5A:
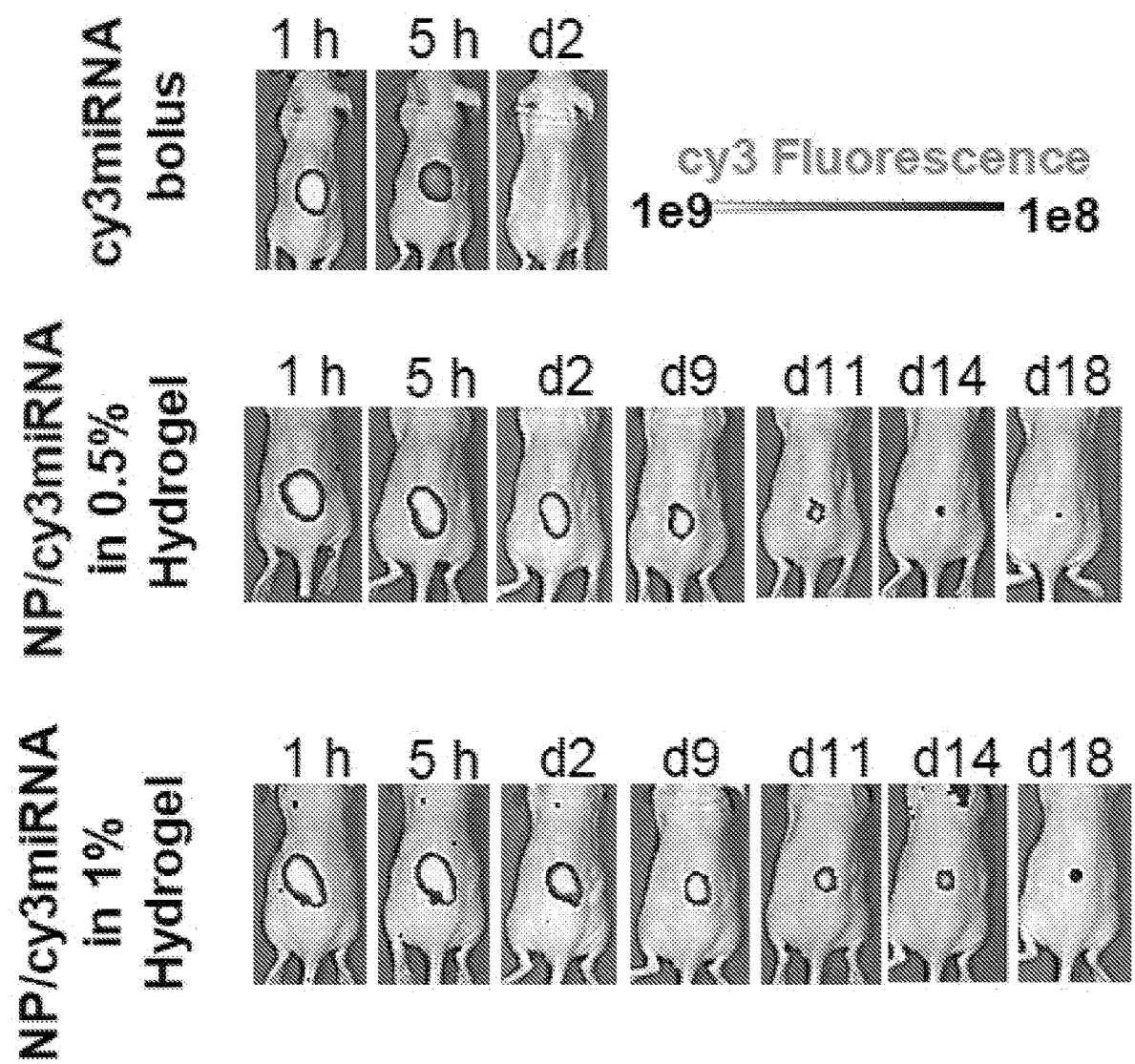
FIGS. 5A-5H. Nanoparticle-hydrogel composite offers slow sustained delivery of miRNA locally to tissue in vivo and reduces tumor growth in subcutaneous mesothelioma tumors upon a single injection.
Figure 5B:
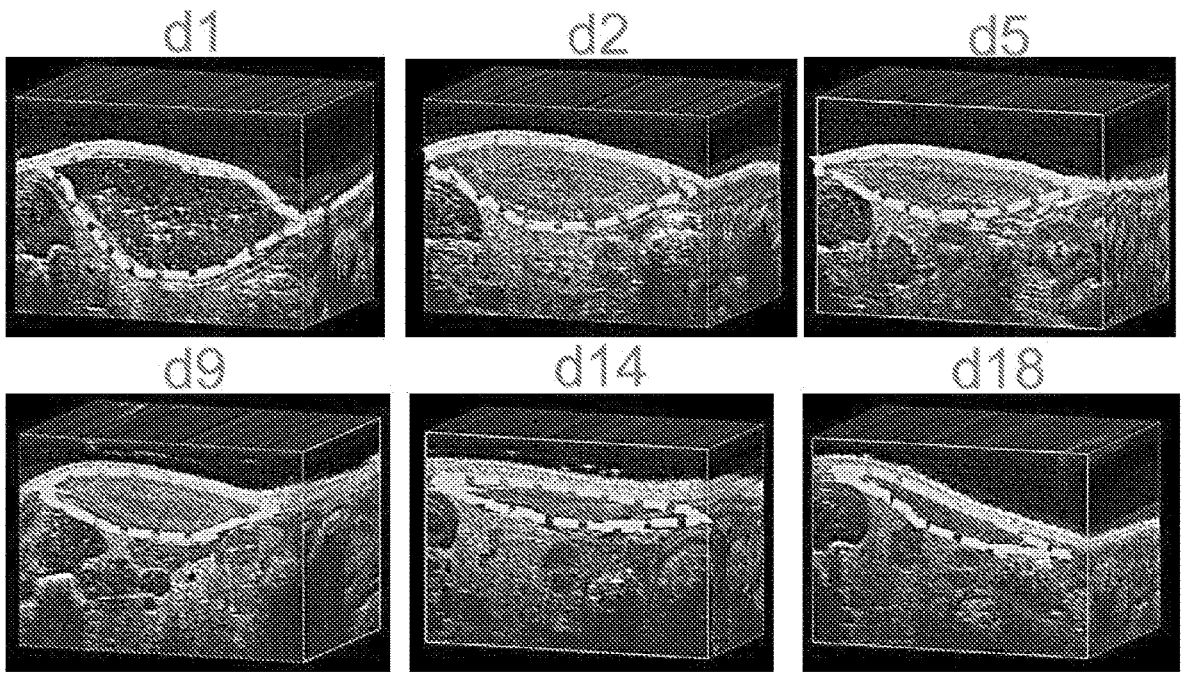
Figure 19A:
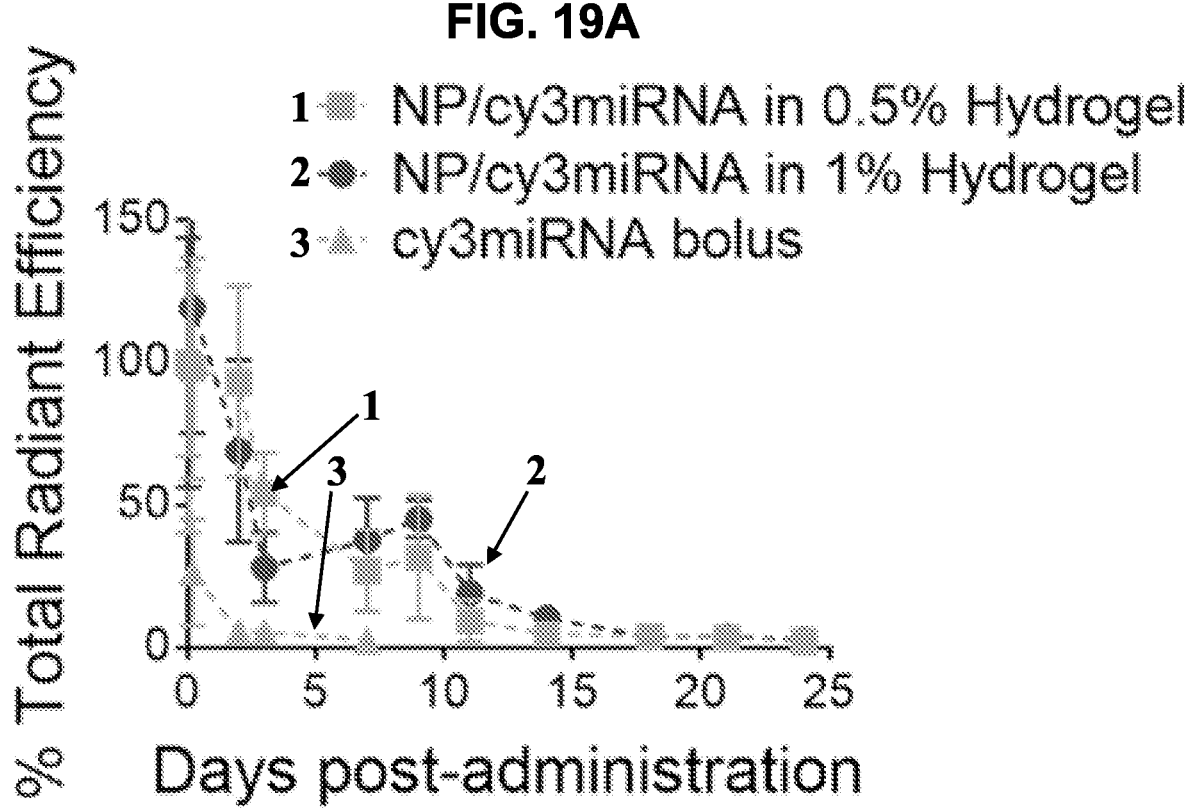
FIGS. 19A-19C. Biodegradable Peptide 3 hydrogel composite promotes sustained delivery of miRNA upon a single subcutaneous injection in athymic nu/nu mice.
Figure 19B:
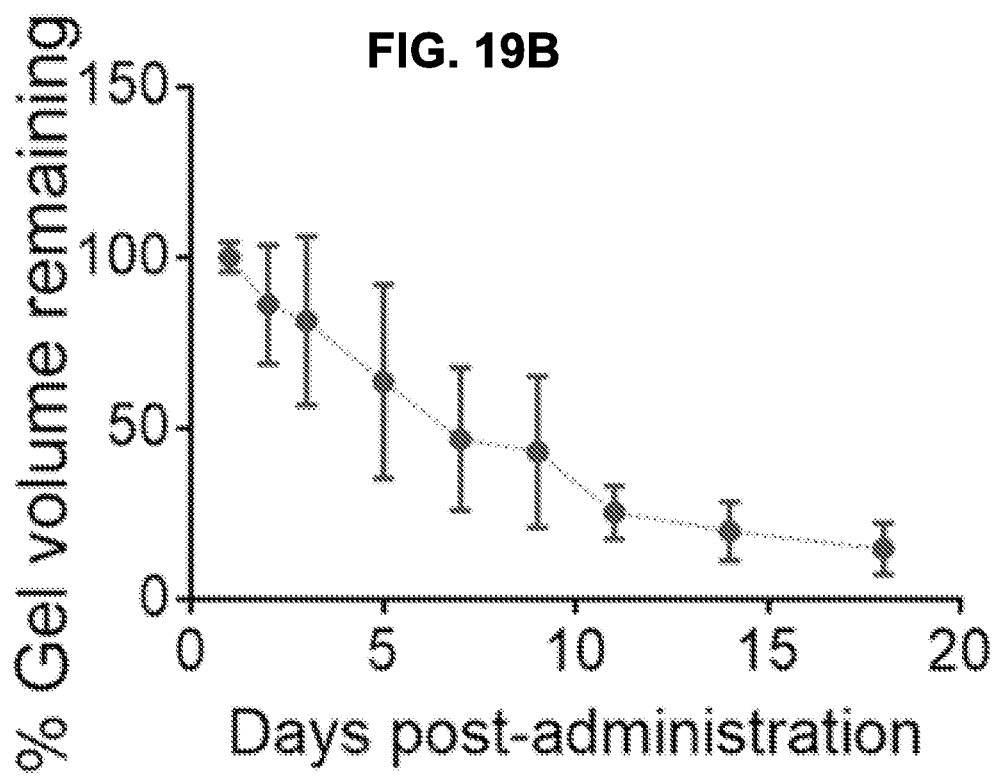
Figure 19C:
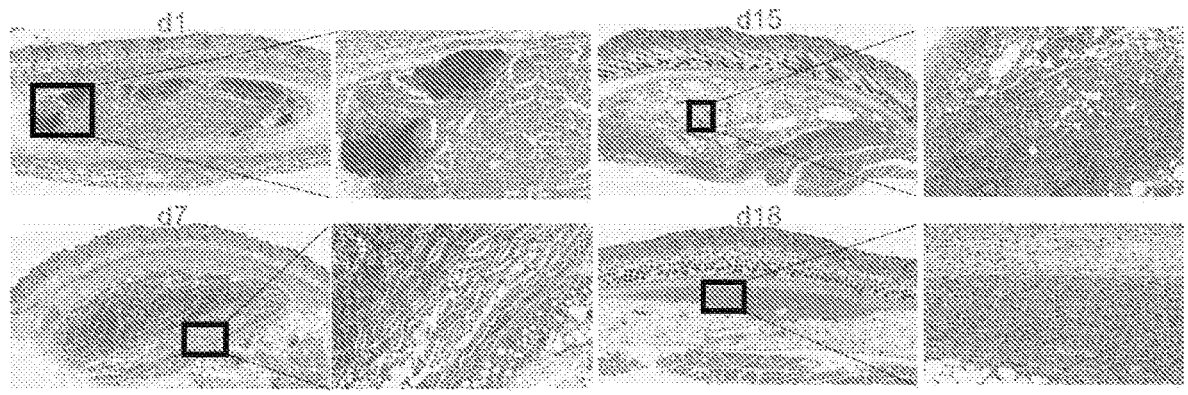

To monitor release of miRNA payload in athymic nude mice, cy3-conjugated miRNA was loaded into gel networks composed of 0.5% and 1% (w/v) Peptide 3. The composite gel stayed localized at the point of administration when injected subcutaneously and can deliver Cy3-labeled miRNA locally to tissue for over two weeks (FIG. 5A). In contrast, miRNA delivered as a bolus rapidly clears out within a day. Accounting for the slower release rate, 1% gel composites were used for subsequent in vivo experiments. To understand whether the release of miRNA is also accompanied with biodegradation of the hydrogel, the degradation rate of hydrogel composites was monitored using 2D ultrasound (FIG. 5B) (for a description of 2D ultrasound, see Leng, et al. J Tissue Eng Regen Med, 11(3): 822-830, 2017). While monitoring biodegradation of the hydrogel using 2D ultrasound, difference of echogenicity between gel and the surrounding tissue provided adequate contrast while the hydrogel could be visualized with a well-defined boundary. Immediately after injection, gel appeared to be hypoechoic or low-level gray, while the echogenicity increased at day 1, possibly indicating solidification of the assembly post shear-thinning delivery. Volume of the 3D implant gradually decreased over time, indicating that the gel persisted for at least 18 days in vivo (FIG. 19B). Such observation correlates with the results of hematoxylin and eosin staining of the isolated tissue surrounding the injection site at day 1, 7, 15 and 18 post-subcutaneous administration (FIG. 19C). Gel composite sustains at the injection site for at least 18 days (FIG. 19). Thus, the hydrogel composites act as a localized miRNA depot releasing miRNA payload for at least 2 weeks with subsequent bio-resorption of the gel.

Figure 5C:
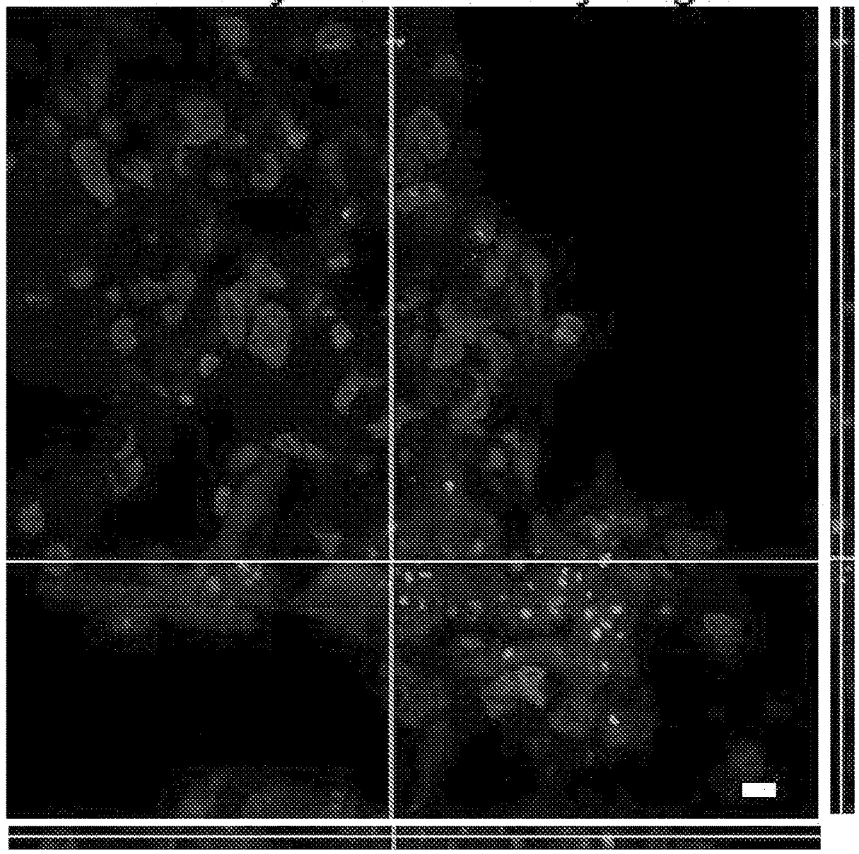
Figure 20A:
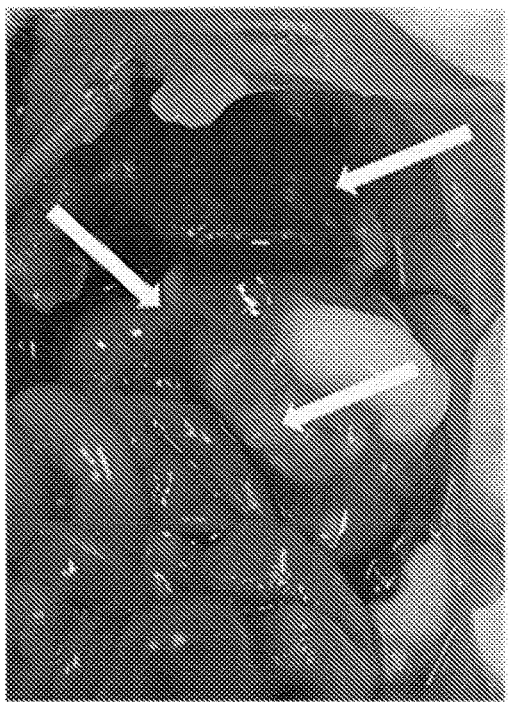
FIGS. 20A-20B.
Figure 20B:
Figure 21A:
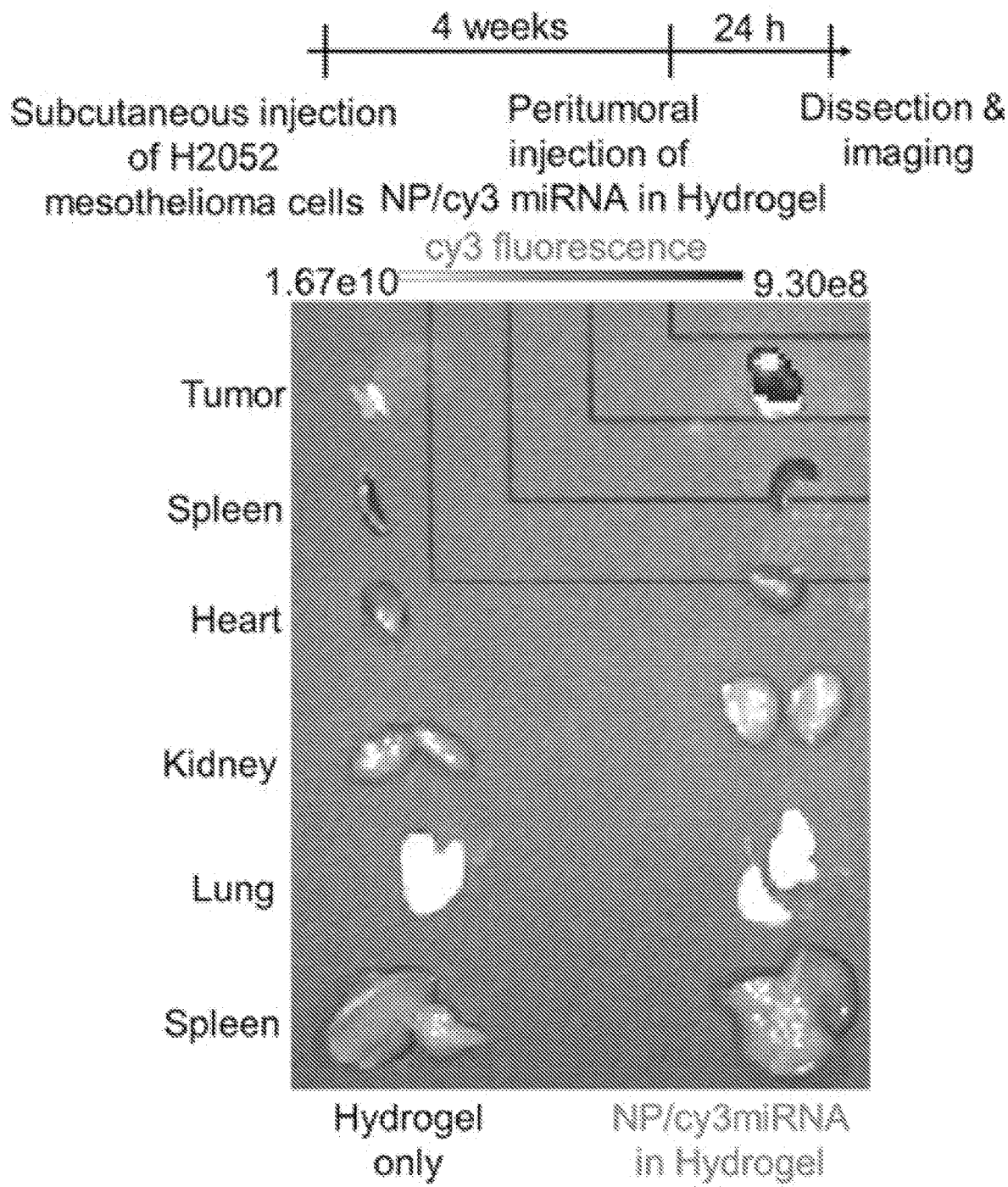
FIGS. 21A-21C. Ex vivo biodistribution of cy3miRNA when injected as a nanoparticle in complexation with Peptide 1 and encapsulated within 1% Peptide 3 hydrogel. Hydrogel composites were peritumorally administered in NOD/SCIDγ mice bearing subcutaneous H2373 tumor grafts. Tumors and vital organs were collected 24 h post-injection for imaging cy3 fluorescence in an IVIS Xenogen imaging system. Corresponding images from a control mouse receiving blank hydrogel at the same time are also shown.
Figure 21B:
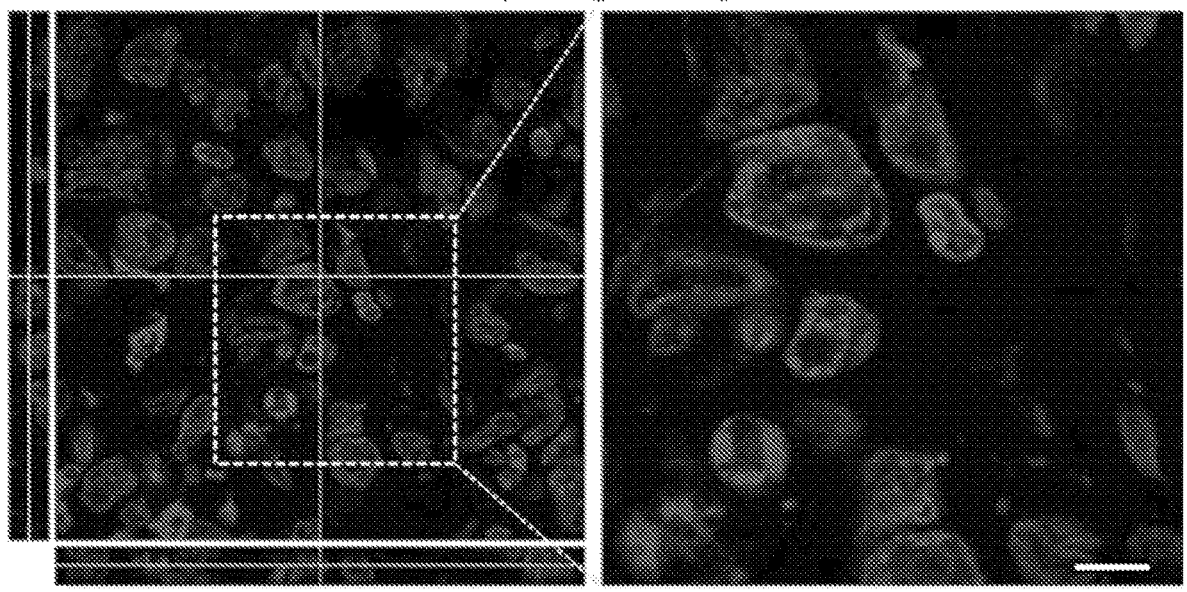
Figure 21C:
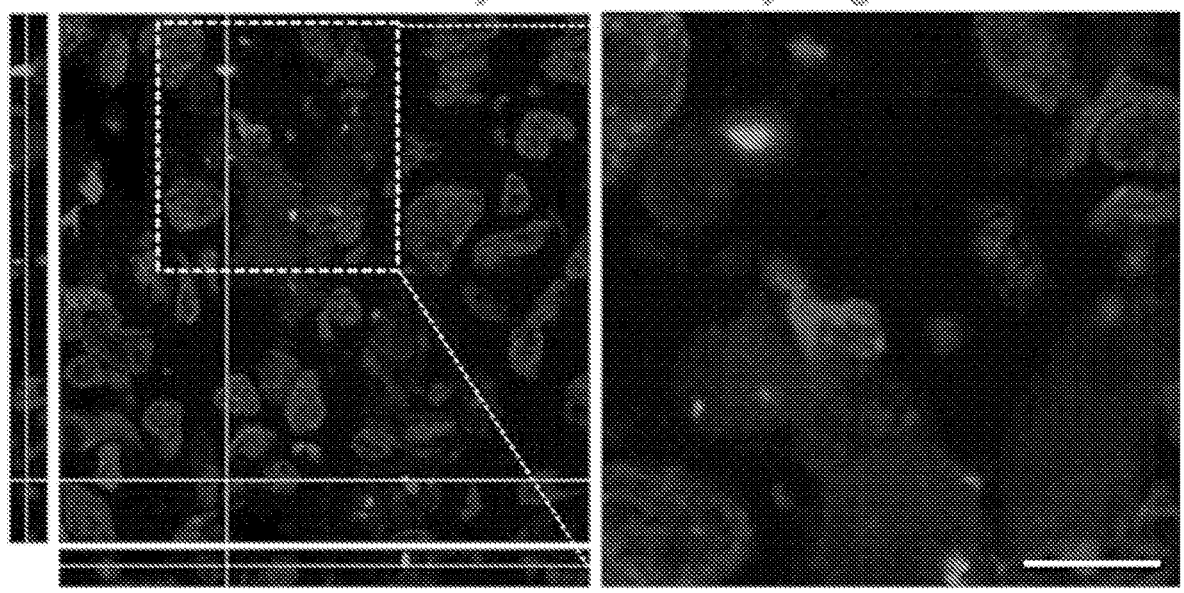
Figure 22A:
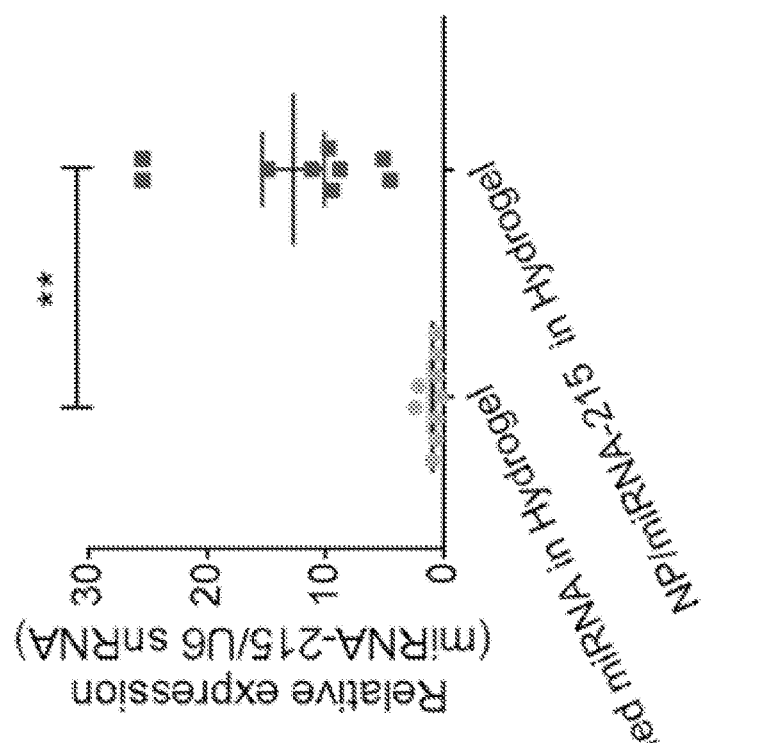
FIGS. 22A-22B. qPCR data showing in vivo transfection of functional miRNA-215. Gene expression was determined from total RNA isolated from subcutaneously grown H2373 tumors of mice injected with gel composites containing miRNA-215 and scrambled miRNA at (FIG. 22A) week 1 and (FIG. 22B) week 2 post-administration. mRNA levels are normalized to U6 snRNA. Data shown is for n=3 mice in each group, each measured as a triplicate. Error bars in ±SEM. *p<0.05, **p<0.01, student's t test.

Tumor growth reduction was assessed in subcutaneous and orthotopic mesothelioma models treated by hydrogel-delivered miRNAs. Sarcomatoid subtype mesothelioma cell line H2373 was used in subcutaneous xenograft experiments, while H2373 and H2052 cell lines were used in orthotopic tumor experiments (FIG. 20). Beforehand, the biodistribution profiles of miRNA delivered with the hydrogel composites was assessed. In mice with subcutaneous xenografts treated by peritumoral injection of gel composites, cy3 expression was exclusively found to be in tumor tissue at 24 h (FIG. 22A). No accumulation was observed in other vital organs at this time point. Confocal microscopy images from cross-sections of xenograft collected at a similar time-point revealed localization of cy3miRNA in tumor cells throughout the tumor mass (FIGS. 5C and 21B), indicating nanoparticles loaded with miRNA get released locally from hydrogel composites and navigate into tumor cells in the vicinity. Remarkably, this result illustrates relatively deep penetration of the nanoparticle payload into tumor masses when delivered via hydrogel composite.

Figure 5D:
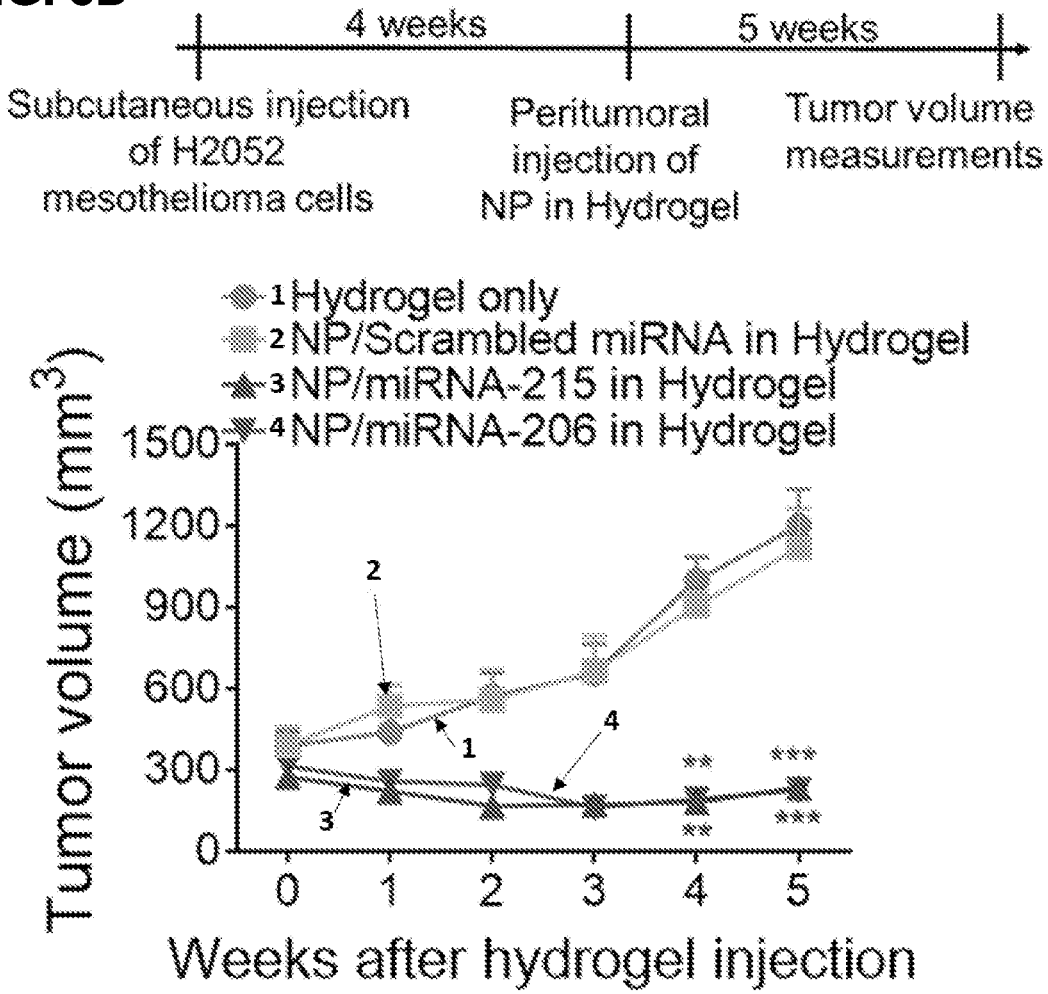
Figure 5E:
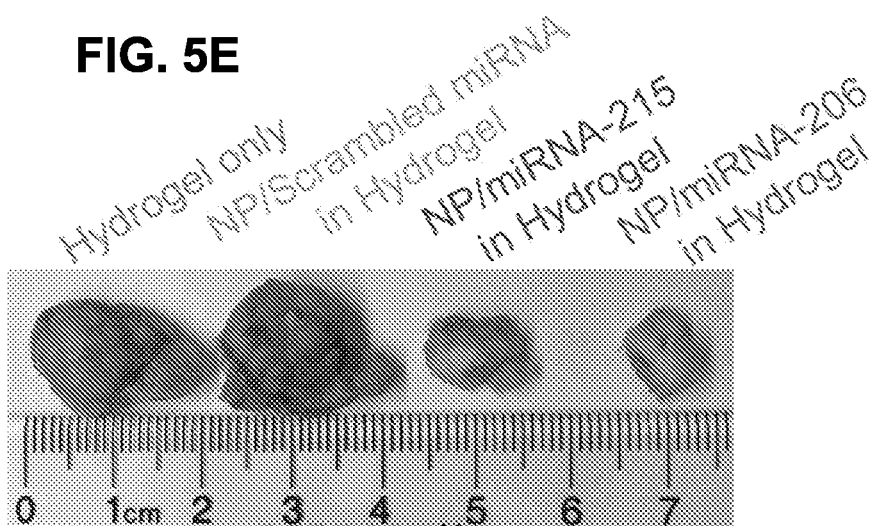
Figure 5F:
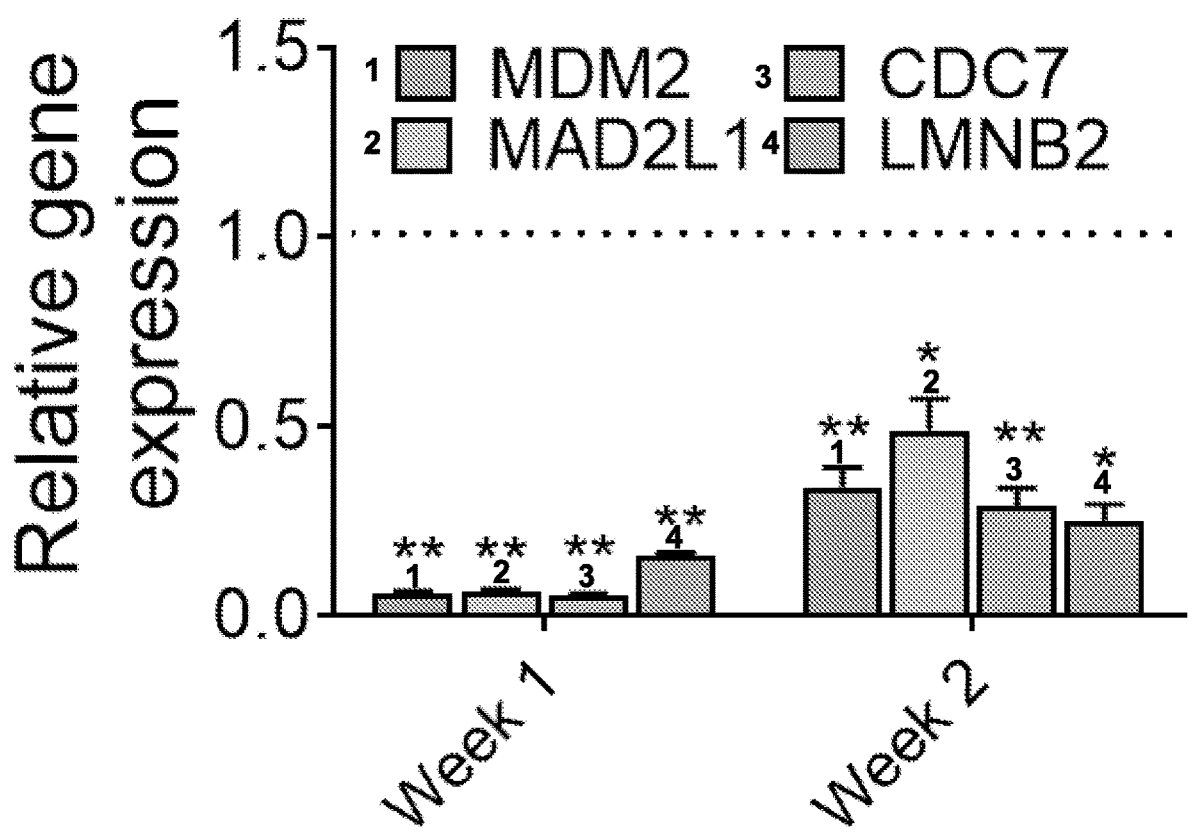
Figure 5G:
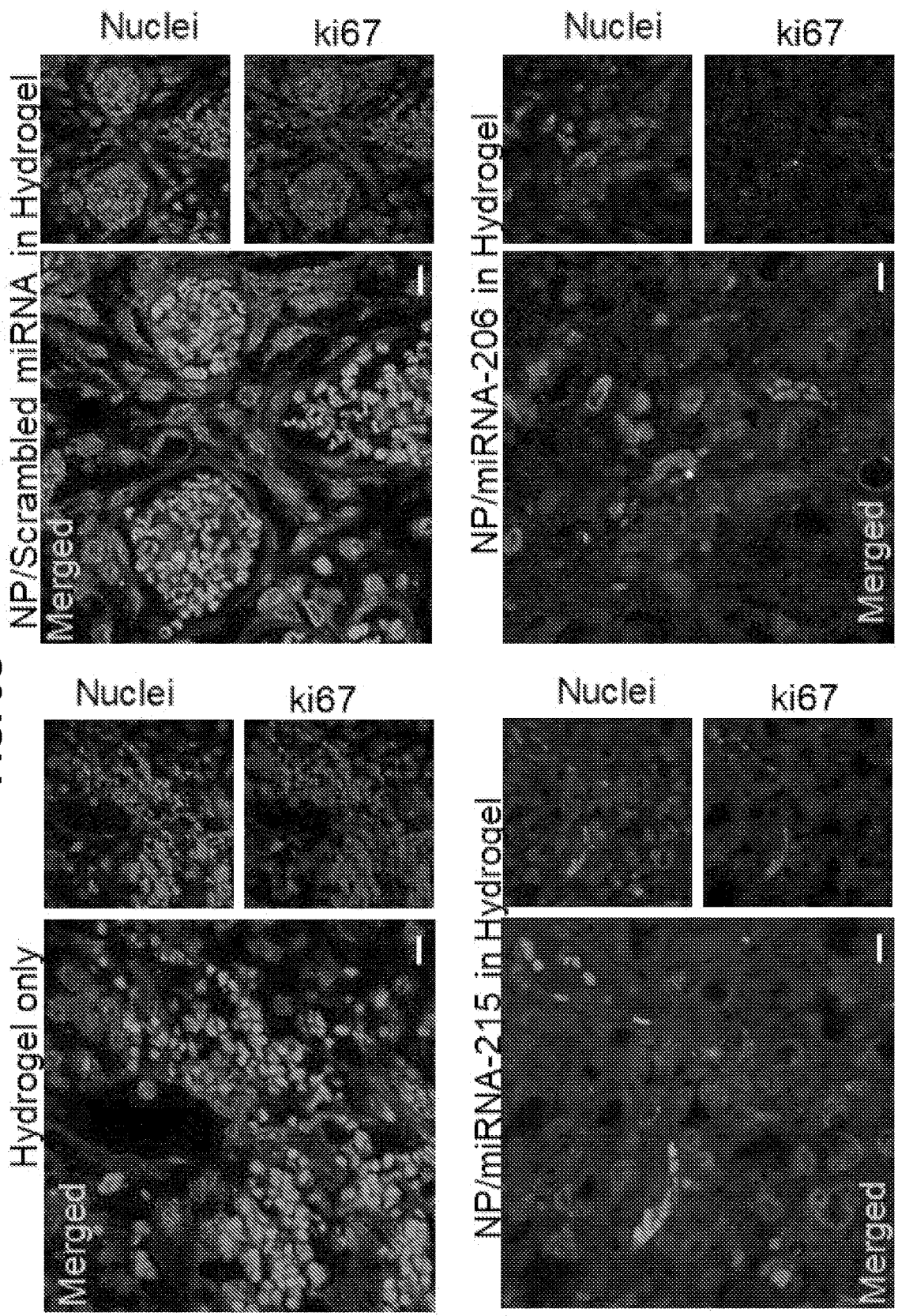
Figure 5H:
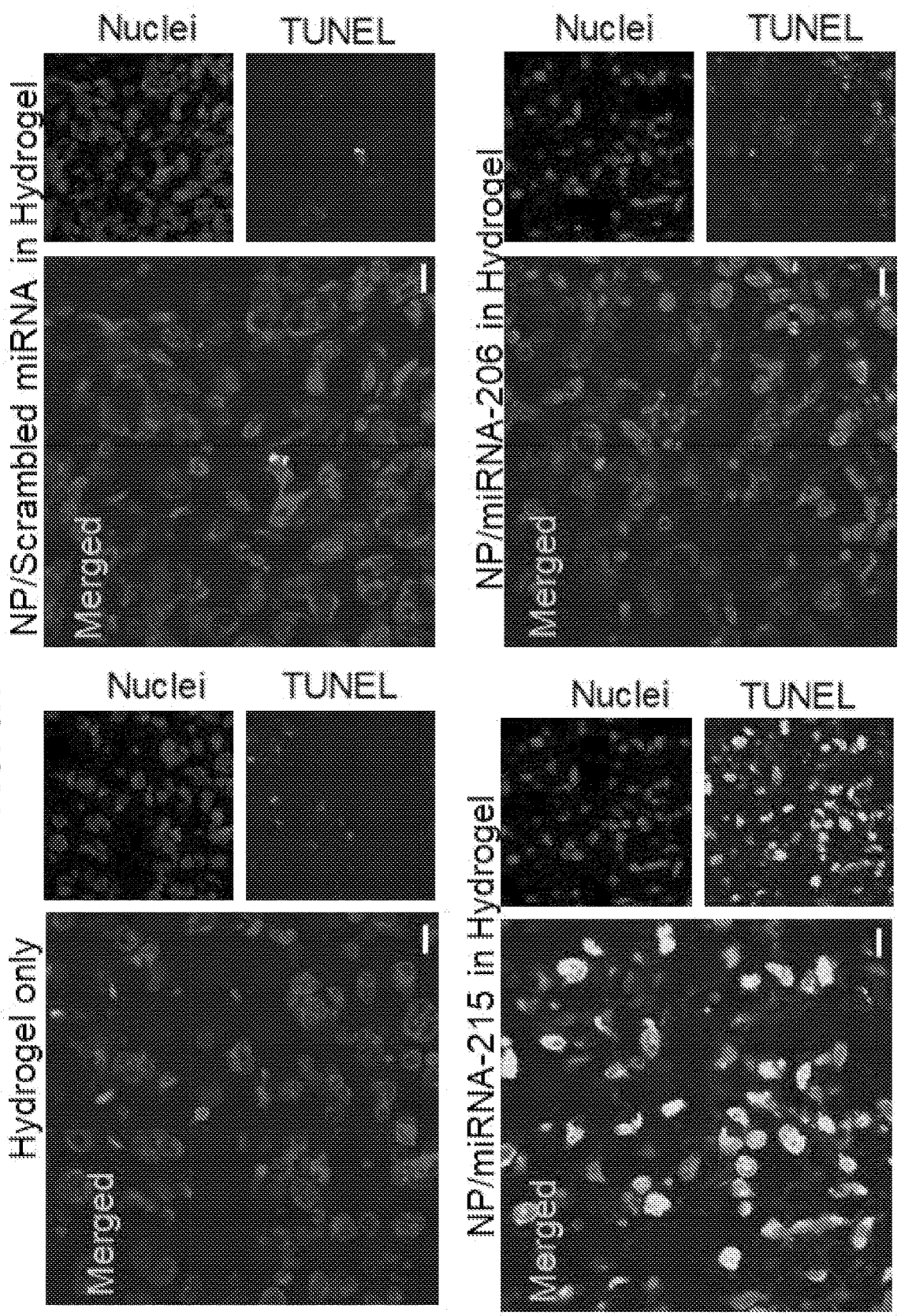
Figure 6A:
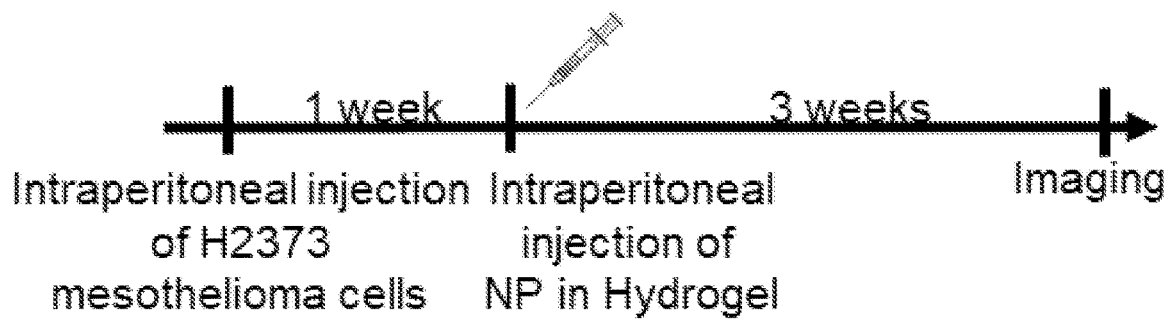
FIGS. 6A-6H. Nanoparticle-hydrogel composites can effectively reduce tumor growth in orthotopic H2373 (FIGS. 6A-6D) and H2052 (FIGS. 6E-6H) peritoneal tumor models in NOD/SCIDγ mice upon a single administration.
Figure 6B:
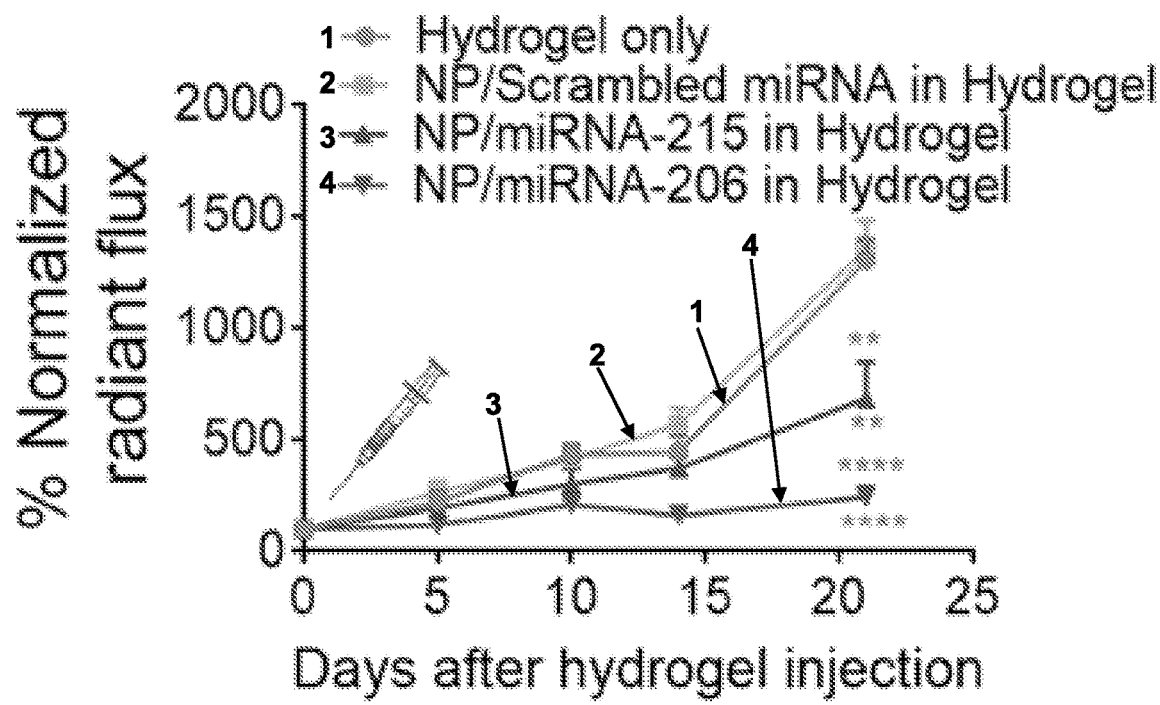
Figure 6C:
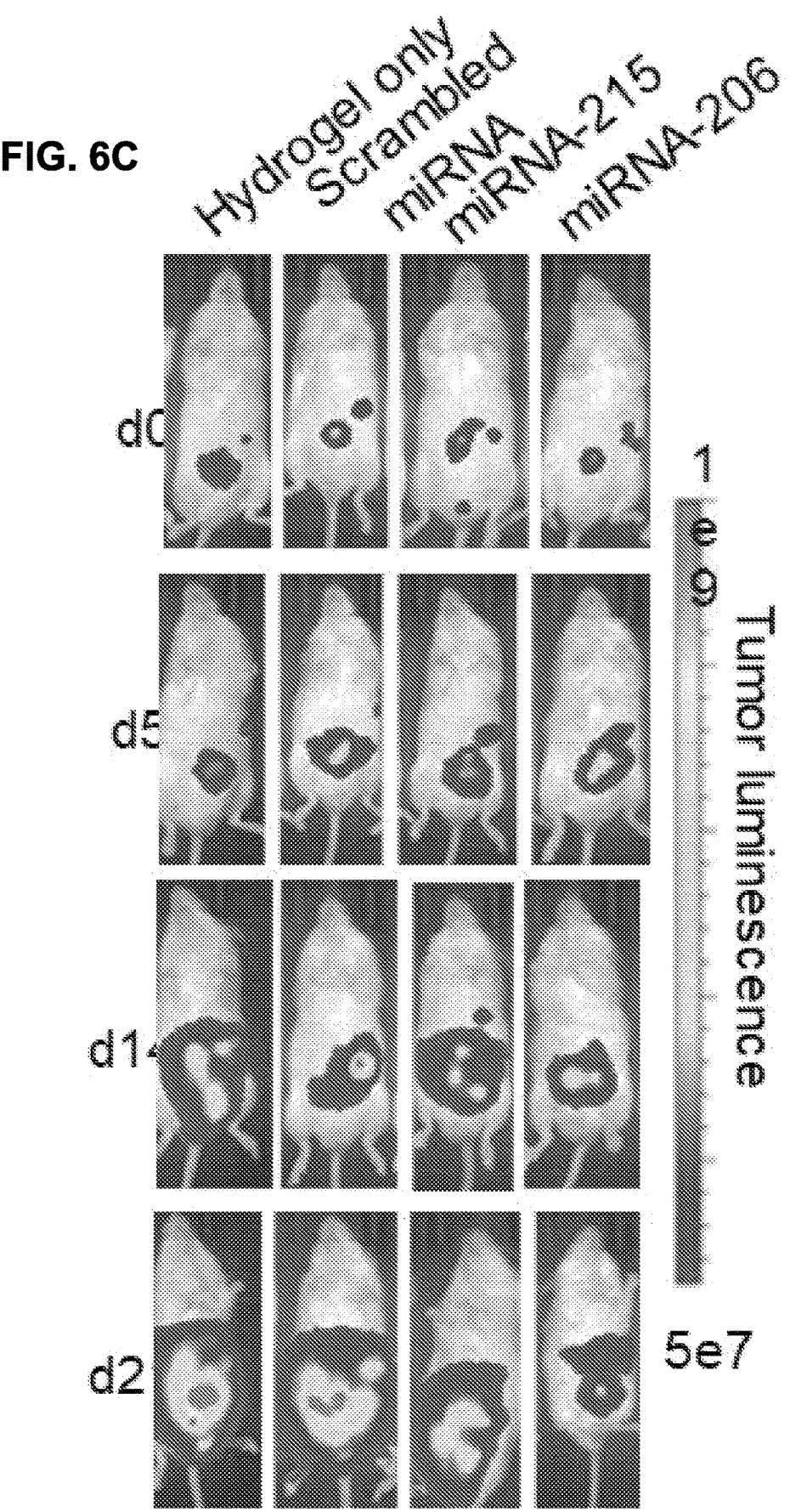
Figure 6D:
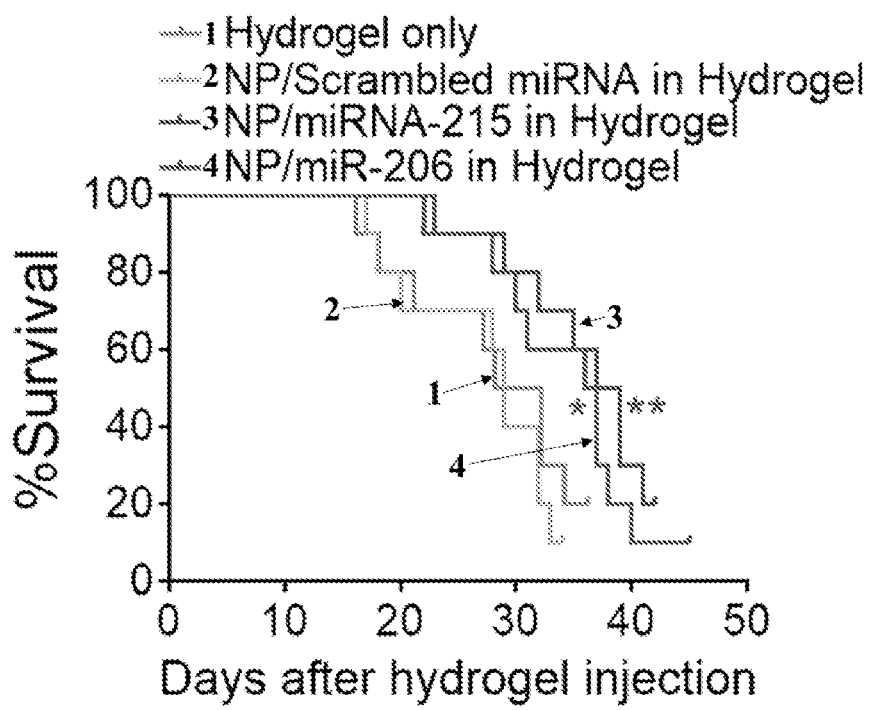
Figure 6E:
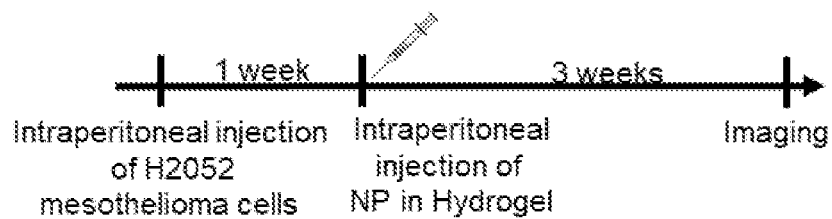
Figure 6F:
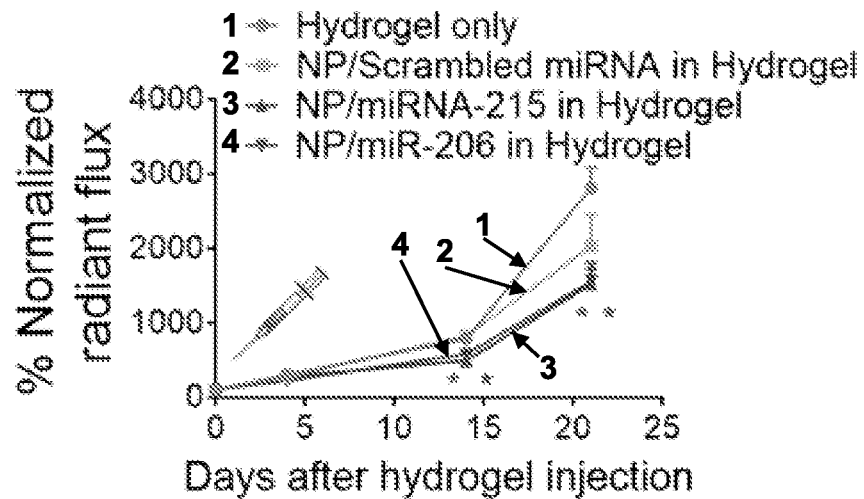
Figure 6G:
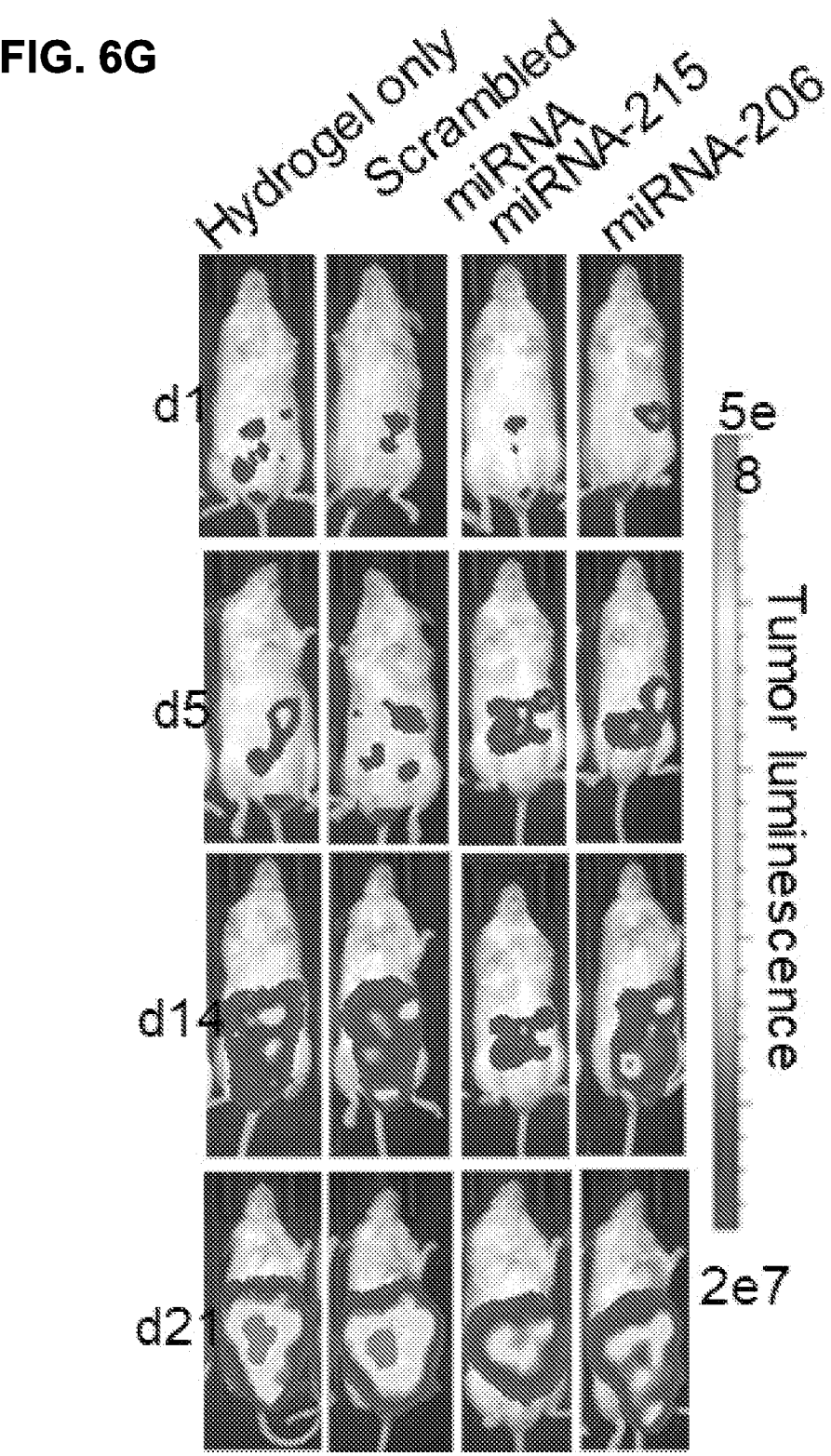
Figure 6H:
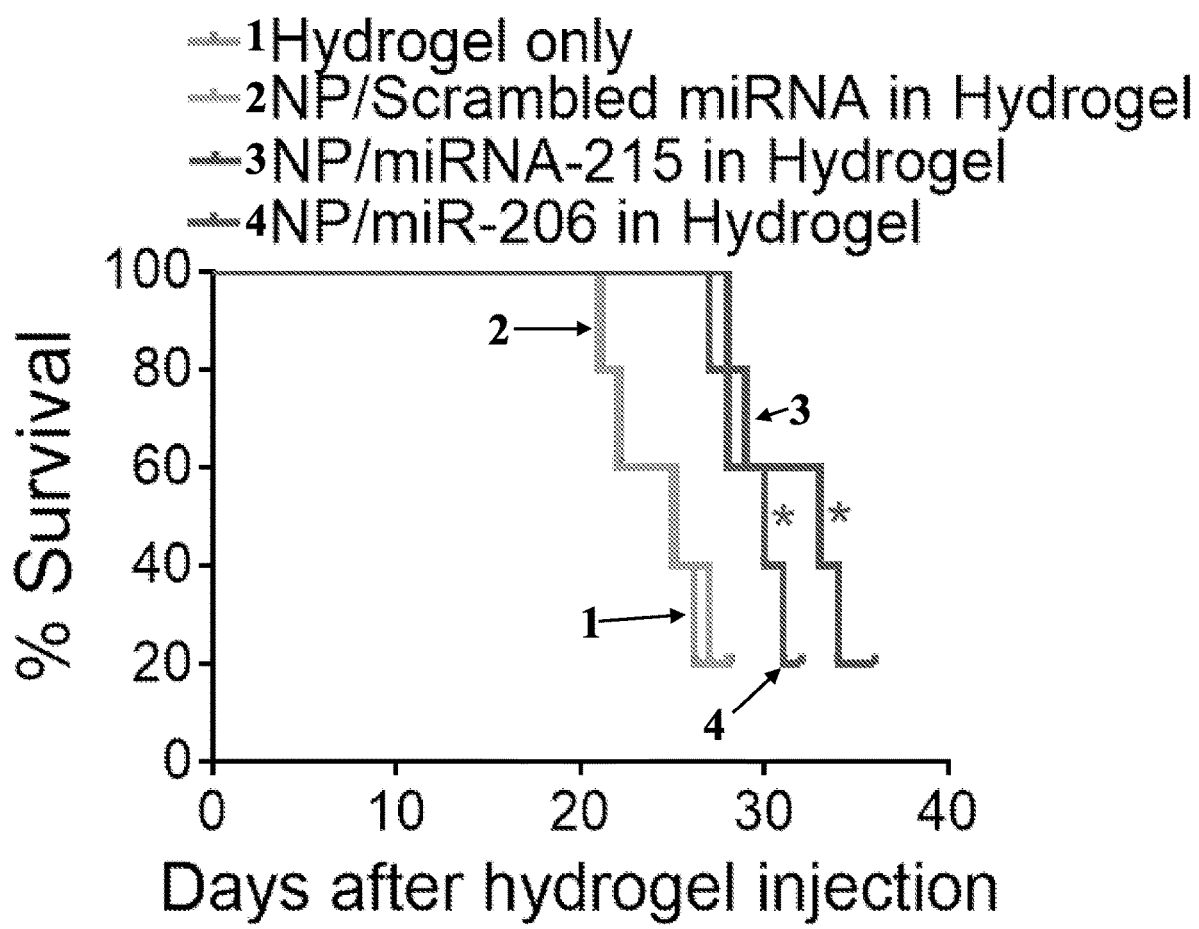
Figure 22B:
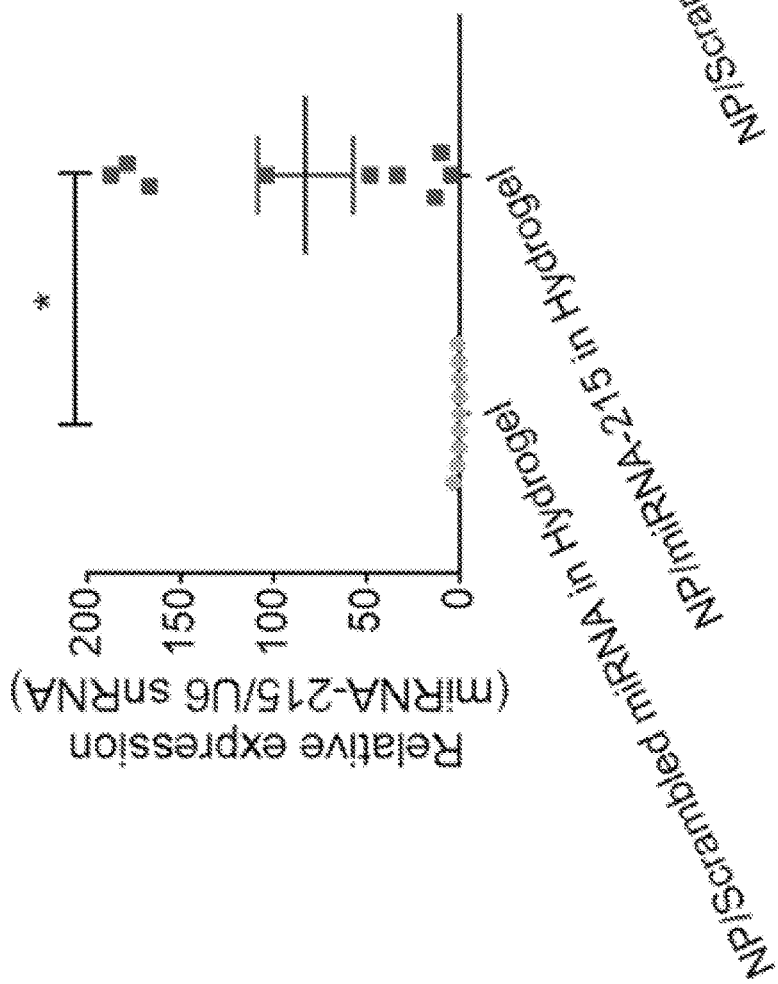
Figure 23A:
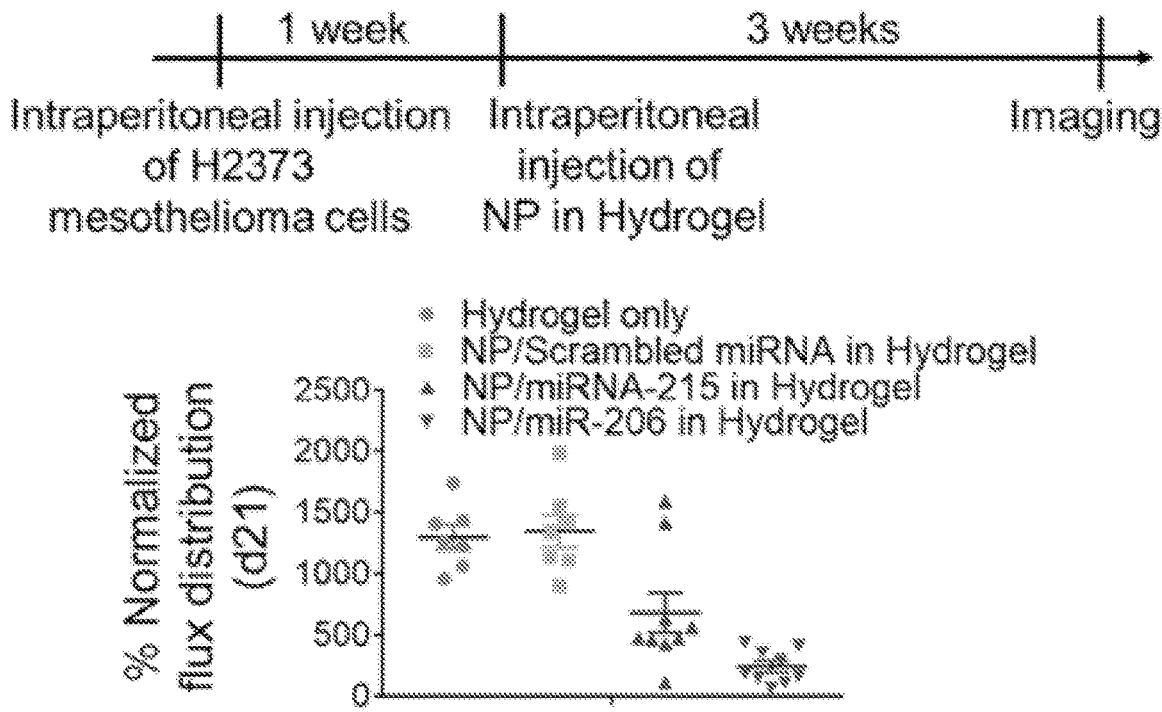
FIGS. 23A-23B. Normalized radiant flux distribution around the tumor in mice bearing peritoneal (FIG. 23A) H2373 and (FIG. 23B) H2052 tumor grafts administered intraperitoneally with hydrogel composites 21 days post-injection.
Figure 23B:
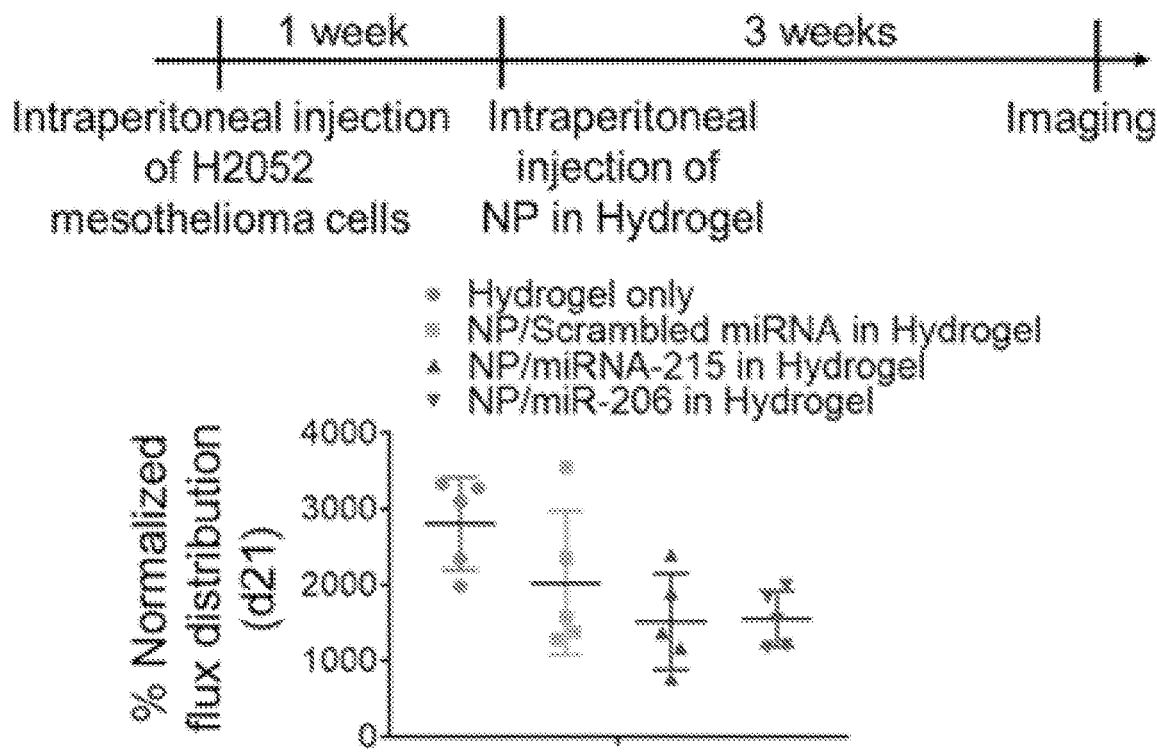

Therapeutic efficacy of the nanoparticle hydrogel composite was demonstrated by showing specific gene targeting via delivery of MPM-associated functional tumor suppressor miRNAs (pro-apoptotic miR-215-5p or anti-proliferative miR-206-5p (Xu, et al. Chest, 144(5): 1632-1643, 2013)). Hydrogel composites were injected peritumorally to treat mice bearing H2373 subcutaneous xenografts. After a single injection, tumor volume was significantly smaller in miR-215 or miRNA-206-treated groups as compared to controls (FIGS. 5D-5E). In the xenografts at week-one post-injection, high levels of miR-215-5p were detected (FIG. 22A), that persisted an additional week (FIG. 22B). Importantly, specific target genes were suppressed in treated xenografts at week-one (FIG. 5F), that likewise persisted into the following week of observation (FIG. 5F). Immunohistochemical analysis of xenografts at week-four (FIG. 5G), showed low expression of Ki-67, a proliferation marker, with either miRNA treatment. Apoptotic cells were predominantly observed in miR-215-treated tumors, but not in those treated with miR-206 (FIG. 5H), as predicted from their dissimilar molecular mechanisms. Taken together, these results verify that our hydrogel composite can successfully deliver specific miRNA to tumor cells in vivo.

To model potential clinical performance, we analyzed tumor regression in an orthotopic mesothelioma model (FIG. 6). Growth of intraperitoneal mesothelioma xenografts (average time one week) were monitored by luminescence of luciferase-expressing tumor cells (H2373 or H2052) (FIGS. 6A-6C and 6E-6G, respectively). Separate groups of mice were administered a single intraperitoneal injection of hydrogel composites carrying miR-215-5p or miR-206-5p and monitored for three weeks (FIGS. 6B-6C and 6F-6G). Over the observation period, significant tumor growth retardation effects were documented in all treated versus control groups. The absolute magnitude of tumor suppression between miR-215 and miR-206 treatments reflects inherent molecular heterogeneity impacting clinical response. The anti-tumor effect exerted by miRNAs translated to significantly improved survival in treated mice by Kaplan-Meier analysis (FIGS. 6D-6H). These preclinical results are highly promising and provide rationale for further translational development.

CONCLUSION

Data provided herein demonstrates the potency of the novel miRNA-bound nanoparticle-hydrogel composite delivery vehicle to treat cancer, such as mesothelioma, a recalcitrant surface malignancy in need of better therapies. Since miRNA are endogenous in non-malignant cells, their use as anti-cancer agents could have a wider therapeutic window with fewer side effects compared to conventional chemotherapy. With effective delivery of miRNA to tumor cells, the strategy provided herein leverages the unique property of miRNA coherently regulating multiple genetic pathways, not just a specific mechanism or single therapeutic target. The hydrogel platform enabled multiple advantages: (i) shear-thinning facilitates deployment route with ease of syringe-injection that, dependent on delivered volume, would coat large surface areas, or similarly be sprayable; (ii) locoregional delivery minimizes off-target effects as well as systemic toxicity; (iii) fine-tunable hydrogel composition provides enormous flexibility in release kinetics of therapeutic payloads and, by extension, adaptability to handle any type of nucleic acid, proteins and other such biologics alone or in synergistic combinations; and (iv) biodegradability of the gel enhances safety in vivo, obviates need for removal and permits additional applications as needed. Locoregional delivery of the hydrogel material should benefit other surface cancers such as ovarian carcinoma or other cancers that often cannot be radically resected to negative margins like brain gliomas.

Methods

Syntheses of peptides. Traditional Fmoc-based solid phase peptide synthesis strategies were used employing RINK amide resin and HCTU activation. Resin-bound dry peptide was cleaved and side chain protecting groups were removed using cleavage cocktail of TFA/thioanisole/ethanedithiol/anisole (90:5:3:2) for 2 h under Argon atmosphere. After diethyl ether precipitation, crude Peptides 1, 2 and 3 were purified via RP-HPLC using a preparative Vydac C18 peptide column with a flow rate of 8 mL/min. Standard A (0.1% TFA in water) and Standard B (90% acetonitrile, 9.9% water, 0.1% TFA) were used as elutants. Purified peptide was lyophilized three times from water before using for hydrogelation. Peptide 4 was similarly synthesized, and crude peptide was purified using a preparative PolymerX 10µ RP-1 column with a flow rate of 8 mL/min. Standard C (20 mM ammonium bicarbonate) and Standard D (20 mM ammonium bicarbonate in 80:20 acetonitrile/water, v/v) were used as elutants in this case.

Preparation and characterization of nanoparticles. Purified peptides were dissolved in RNase free water. Concentration of the stock was determined measuring UV absorbance (Agilent 8453 UV-Visible Spectroscopy System) at 220 nm using a molar extinction coefficient $\varepsilon = 15750$ $M^{-1}$ $cm^{-1}$, determined by amino acid analyses. miRNA stock (Thermo Scientific) was reconstituted using RNase free water.

Fluorescence-based binding assay was used to determine interaction between peptides and miRNA. Required amount of FAM-labeled scrambled miRNA was diluted in water and mixed with aqueous solution of peptides in a molar ratio ranging from 0.312 to 200 (peptide vs miRNA). The suspension was incubated for 30 min at 37° C. with constant agitation. Complexes were further diluted with HEPES (25 mM HEPES, pH 7.4) buffer to have a final miRNA concentration of 30 nM. FAM fluorophore on miRNA was excited at 490 nm and emission at 520 nm was recorded using a microplate reader (Tecan Infinite 200) with a band-pass filter of 20 nm. A PTI fluorimeter was used to record fluorescence spectrum for Peptide 1/miRNA nanoparticles at N/P ratio 10:1 (molar ratio of 50:1, Peptide 1 vs miRNA) in the emission range of 500-700 nm.

Hydrodynamic diameters and zeta potentials of complexes were determined using a Zetasizer Nano ZS instrument (Malvern Instruments Ltd.) at 25° C. Peptide 1 diluted in water was mixed with aqueous stock of scrambled miRNA in a 10:1 N/P ratio. 1 µg miRNA was used for complexation. Complexes were further diluted with water to a final volume of 1 mL before measurement at 25° C. Lipofectamine complex was prepared following manufacturer's instructions. Intensity-based size distribution was derived from correlograms using analysis algorithm in-built in Malvern software. Zeta potential values were calculated using Smoluchowski approximation.

Circular Dichroism Spectroscopy. Secondary structure of Peptide 1 in presence or absence of added miRNA was determined using Circular Dichroism (CD) spectroscopy. For recording CD spectra in water, 150 µL from the aqueous solutions of Peptide 1 was mixed with 150 µL of an aqueous solution of scrambled miRNA to maintain peptide vs miRNA N/P ratios at 10:1, 5:1, 2:1 and 1:1. These N/P ratios correspond to peptide vs miRNA mole ratios of 50:1, 25:1, 10:1 and 1:1, respectively. Nanoparticles and soluble peptides of 300 µL total volume were equilibrated for 30 min at 37° C. with agitation. Final concentration of miRNA was maintained at 5 µM. Samples were transferred into a quartz cell of path-length 1 mm and data collection were initiated immediately. Ellipticity was measured over a wavelength range of 190-260 nm at 37° C., using 1 nm step size and a set of 3-5 scans. Raw data was corrected by subtracting the absorbance of samples from those of miRNA and converted to mean residue ellipticity using the equation: $[\theta]=\theta_{obs}/(10*l*c*r)$ where $\theta_{obs}$ is the measured ellipticity (mdeg), l is the path length (0.1 cm), c is the concentration of peptide (determined from UV absorbance at 220 nm) and r corresponds to the number of amino acid residues in the peptide.

Alteration of secondary structure of Peptide 1 in the complex (formed at N/P ratio 10:1) in presence of heparin was measured in CD spectrometer by adding increasing concentration of heparin (0-100 µg/mL) sulfate in water while keeping concentrations of miRNA and Peptide 1 constant. The suspension was incubated with heparin sulfate for 1 h at 37° C. immediately before data acquisition. Raw data was corrected by subtracting the absorbance of samples from those of miRNA and heparin.

Transmission Electron Microscopy (TEM). To determine the structure, nanoparticles were prepared in water so final peptide concentration is 50 µM while maintaining peptide to miRNA molar ratio at 50:1. Samples (~4 µL) were deposited onto 200 mesh carbon coated copper grids and allowed to adhere for 5 minutes. The excess sample was removed with filter paper. Uranyl acetate (5 µL) was used to stain the grids for 30 seconds Grids were dried for 5 minutes. Images were acquired using a Tecnai T12 transmission electron microscope. Particle diameters were analyzed using ImageJ Software and reported as an average for 25-30 particles.

Cellular Internalization of Nanoparticles

Flow cytometry. In vitro miRNA transfection efficiency of nanoparticles was determined using human mesothelioma cell H2052 (ATCC). For flow cytometry, $1.2\times10^5$ cells were seeded on 6 well plate 24 h before treatment and allowed to grow under normal culture conditions. FAM (6-carboxyfluorescein, 5' end)-labeled scrambled miRNA (Thermo Fisher) was complexed with Peptide 1 in a 10:1 N/P ratio according to the protocol described above. Nanoparticles obtained were diluted with optiMEM (Thermo Fisher) to maintain a final miRNA concentration of 40 nM. Complexes of commercial transfection agents (In vivo jet PEI, Polyplus-transfection and DharmaFECT, Dharmacon) and equivalent amount of miRNA were prepared according to manufacturers' instruction. To determine mechanism of cellular uptake, cells were incubated with a set of standard endocytosis inhibitors in serum-free media. In each case, cells were pre-incubated with inhibitors for 1 h and then co-incubated with nanoparticles for another 1 h. After washing with cold PBS, cells were trypsinized (with 0.25% trypsin-EDTA solution) for 15 minutes to ensure digestion of any non-internalized cell surface-adhered nanoparticles. Cell pellets were collected by centrifugation, washed with cold PBS and resuspended in 500 µL PBS before analyzing with a BD LSR Fortessa™ flow cytometer. To determine the specificity of the inhibitors towards each endocytic pathway in H2052 cells, cellular internalization of Rhodamine or FITC-labeled Transferrin (marker for clathrin mediated uptake, Thermo Fisher) and Rhodamine or FITC-labeled Dextran (70 kD, marker for micropinocytosis, Thermo Fisher) in presence and absence of inhibitors were analyzed with flow cytometry. FlowJo version 10 was used to analyze flow cytometry data. Median fluorescence intensity (MFI) for gated live cell population was determined for cells treated with each inhibitor and normalized with respect to the sample without inhibitor treatment.

Confocal microscopy. For confocal microscopy, $5\times10^4$ H2052 cells were seeded on 35 mm glass-bottom petri dishes 4 days before transfection. FAM or cy3-labeled scrambled miRNA was complexed with Peptide 1 in an N/P ratio of 10:1 (peptide vs miRNA) according to the protocol described above. Nanoparticles were diluted with optiMEM (Thermo Fisher) to maintain a final miRNA concentration of 40 nM. Cells were incubated for 4 h at 37° C., washed with complete media and imaged using a Zeiss LSM710 confocal microscope. Images were acquired either immediately after washing (0 h) or after 24 h. Cells were incubated with 2 µg/mL Hoechst 33342 for 30 min immediately before imaging at each time point. To determine intracellular distribution of Peptide 1/miRNA nanoparticles, cells treated as above were incubated with lysotracker (100 nM final concentration) for 30 min just before imaging. Lysotracker Red and Lysotracker Blue were used for cells treated with FAM labeled miRNA and cy3-labeled miRNA, respectively. Cells were visualized using a 63× oil objective. Lasers and band pass emission filters were used as: 405 nm laser; 390 nm-465 nm (Hoechst channel), 488 nm laser; 500 nm-550 nm (green channel) and 561 nm laser; 570 nm-600 nm (red channel). Planar and z stack images were processed using ImageJ software (NIH).

To determine intracellular distribution of calcein in presence or absence of Peptide 1/miRNA complex, cells were co-incubated with calcein and scrambled miRNA (unlabeled) complex for 4 h in optiMEM so final miRNA concentration remains at 40 nM. Cells incubated only with calcein were considered as negative controls. Calcein was used at a final concentration of 100 µM. Cells were washed and incubated in complete media for 2 h before imaging with Zeiss LSM710 confocal microscope. A 488-nm laser line and 500-550 nm bandpass filter was used to detect calcein fluorescence.

To evaluate intracellular localization of Peptide 1 and miRNA present in nanoparticles, complexes were prepared by doping in 1 mol % of tetramethyl rhodamine-conjugated Peptide 1 while maintaining final total peptide concentration at 2 µM. To maintain a 10:1 N/P ratio (i.e. 50:1 mole ratio), miRNA was kept at 40 nM final concentration. Cells were incubated for 4 h at 37° C., washed with complete media and imaged similarly as above.

Evaluation of gene silencing with qPCR. To determine efficacy of Peptide 1/miRNA nanoparticles for functional delivery of miRNA into mesothelioma cells, miRNA-215 (Thermo Fisher) was complexed with Peptide 1 following the previously described procedure. A scrambled miRNA with no known sequence similarity to human genes (Thermo Fisher) was used to prepare similar nanoparticles as a negative control. Sequence of miRNAs purchased from Thermo Fisher Scientific are provided in the following table:

systems) using corresponding TAQ-MAN probes (Thermo Fisher). Mean CT values for each sample was normalized to that of β-actin as a housekeeping gene. Data is expressed as a fold change with respect to gene expression in samples treated with scrambled miRNA.

Cell proliferation and apoptosis. To determine biocompatibility of Peptide 1/miRNA nanoparticles, $1 \times 10^4$ H2052 cells were seeded on 96 well plate 24 h before transfection. Nanoparticles prepared with scrambled miRNA were incubated with cells in optiMEM for 4 h to maintain final miRNA concentration at 40 nM in each case. Cells were washed and incubated with fresh culture media for another 44 h. Cell viability was determined 4 h and 48 h post-addition of nanoparticles. 10 µL of MTT solution (5 mg/mL in PBS) was added and cells were incubated for 4 h at 37° C. The supernatant was discarded and 100 µL of DMSO was added to dissolve the purple formazan crystals. Absorbance

| miRNA name | Part number | Product ID | Mature Accession | Mature miRNA sequence | Stem loop accession | Stem loop sequence |
|---|---|---|---|---|---|---|
| hsa-miR-206 | 4464070 | MC10409 | MIMAT0000 9260 | UGGAAUGUAAGG AAGUGUGUGG (SEQ ID NO: 50) | MI0026600 | ACACACUUCCUU ACAUUCCAUU (SEQ ID NO: 83) |
| hsa-miR-215-Sp | 4464066 | MC10874 | MIMAT0002 730 | AUGACCUAUGAA UUGACAGAC (SEQ ID NO: 52) | MI0000291 | CUGUCAAUUCAU AGGUCAUUU (SEQ ID NO: 84) |
| mirVana™ miRNA Mimic, Negative control #1 | 4464061 | | | | | |
| FAM-labeled Pre-miR Negative control #1 | AM17121 | | | | | |
| Cy3 Dye-labeled Pre-miR Negative control #1 | AM17120 | | | | | |

$2 \times 10^5$ cells were seeded on 6 well plate 24 h before treatment and allowed to grow under normal culture conditions. Cells were incubated with complexes diluted with optiMEM (final miRNA concentration 40 nM) for 4 h, washed and incubated with fresh complete media for another 44 h. Complex of lipofectamine and equivalent amount of miRNA was prepared according to manufacturer's instruction and treated to cells in a similar way. Total RNA was isolated from cells using TRIzol™ (Thermo Fisher) following standard protocol. Briefly, 1 mL of TRIzol™ solution was used to lyse cells in each well. Collected suspension was mixed with 0.2 mL HdPLC grade chloroform, centrifuged at 12,000 g for 20 minutes at 4° C. and the transparent upper layer was collected. RNA was precipitated from the upper aqueous layer by incubating with 0.5 mL of molecular biology grade isopropanol for 15 minutes followed by centrifuging at 12,000 g for 20 minutes at 4° C. Isolated RNA was washed with 70% ethanol and resuspended in RNase free water. RNA concentration and purity were determined in Nanodrop. cDNA from each treatment groups was synthesized using High-Capacity cDNA Reverse Transcription Kit (Applied Biosystems) and mRNA expression levels for genes CDC7, LMNB2, MDM2 and MAD2L1 were measured on QuantStudio 6 Flex Real-Time PCR System (Applied Biowas measured at 550 nm using a UV plate reader (Biotek, Winooski, VT). The absorbance of each sample was subtracted from a blank (without MTT solution), and percent viability calculated using the equation:

(Absorbance$^{treated}$/Absorbance$^{untreated}$)×100.

LDH assay kit (Roche) was used to determine any possible cytotoxicity of Peptide 1/miRNA nanoparticles and soluble Peptide 1. Cell supernatant was taken out after 4 h of treatment and a reaction mixture containing diaphorase/NAD+/iodotetrazolium chloride/sodium lactate was added following manufacturer's instructions to detect any released LDH (Lactate Dehydrogenase). Triton X-100 at a final concentration was used as a high control for maximal releasable LDH, while untreated cells were taken as low control for spontaneous LDH release. Absorbance was measured at 490 nm after 5 minutes of incubation at 37° C. Cytotoxicity was calculated using the equation:

(Absorbance$^{treated}$−Absorbance$^{low\ control}$/ Absorbance$^{high\ control}$−Absorbance$^{low\ control}$)×100.

To evaluate the anti-proliferative ability of intracellularly delivered miRNA-215, H2052 cells plated at a density of $2.5 \times 10^3$ one day before transfection were similarly treated. Each sample was incubated for 4 h in optiMEM with 40 nM final miRNA concentration, washed and incubated with complete media for another 72 h or 120 h. Cell viability was determined using CellTiter 96® Aqueous One Solution Cell Proliferation Assay (Promega) with absorbance measured at 490 nm.

For apoptosis assay, $1.5 \times 10^5$ cells were seeded on 6 well plate 24 h before treatment. Cells were incubated with nanoparticles diluted with optiMEM (final miRNA concentration 100 nM) for 4 h, washed and incubated with fresh complete media for another 90 h. To determine the extent of apoptosis induction, Annexin V-FITC/propidium iodide staining kit (Sigma) was used according to manufacturer's instruction. Briefly, cells were washed with PBS, trypsinized and centrifuged. Cell pellets were suspended in 1× Binding buffer, incubated with Annexin V-FITC and propidium iodide for 15 minutes at room temperature. Fluorescence intensity of Annexin V-FITC and propidium iodide bound to cells were measured with a BD LSR Fortessa™ flow cytometer. FCS Express 6 Flow Research Edition software was used to analyze data.

Clonogenicity assay. Clonogenicity potential of transfected miRNA-215 was determined with 2D colony formation assay and 3D soft agar assay. $2.5 \times 10^3$ H2052 cells were seeded on 96 well plate 24 h before transfection and treated with the nanoparticles. Each sample was incubated for 4 h in optiMEM with 40 nM final miRNA concentration, washed and incubated with complete media for overnight. Cells were trypsinized, counted under a hemocytometer and $1 \times 10^3$ transfected cells were seeded on 12 well plate. Cells were allowed to adhere and proliferate under normal culture conditions for 4 weeks. Colonies were stained with crystal violet (0.5% w/v, 25% methanol) and imaged.

To determine anchorage-independent cell growth, a soft agar assay was performed on 12 well plate with pre-transfected cells. H2052 cells were seeded and treated on 96 well plate following the protocol described above. Before transferring transfected cells on 12 well plates, base agar layer was constructed with 0.4% agarose (w/v in complete media) and allowed to solidify at room temperature. Transfected cells were trypsinized, counted and $1 \times 10^3$ cells resuspended in complete media containing 0.35% agarose were used to constitute the top agar layer. Cells were allowed to grow in 3D for 6 weeks under normal culture conditions, imaged and counted.

Preparation and characterization of hydrogel composites. Required amount of miRNA was diluted in water and mixed with an aqueous solution of Peptide 1 in a 10:1 N/P ratio to maintain a final volume of 25 µL. The suspension was incubated for 30 min at 37° C. with constant agitation and the resulting nanoparticles were mixed with 25 µL of chilled 2×HBS (50 mM HEPES 300 mM NaCl, pH 7.4). 50 µL of 1% (w/v) solution of a hydrogelating peptide (Peptides 1, 2, 3 and 4) was prepared in a chilled 25 mM HEPES (pH 7.4), mixed with an equal volume of nanoparticle suspension and incubated at 37° C. for overnight to afford 0.5 wt % hydrogel composites. Gel composites containing 1% of hydrogelating peptide was also prepared similarly. For Transmission Electron Microscopy of gel composites, ~4 µL of the sample was deposited onto 200 mesh carbon coated copper grids and allowed to adhere for 30 seconds. The excess sample was removed with a filter paper. Uranyl acetate (5 µL) was used to stain the grids for 30 seconds. Grids were dried for 2-3 minutes. Images were acquired using a Tecnai T12 transmission electron microscope.

Rheological properties of hydrogel composite. Rheological characterization of preformed hydrogel composite was conducted on a TA Instruments AR-G2 rheometer at 37° C. using 8 mm stainless steel parallel geometry at a gap height of 0.5 mm. Hydrogel samples for rheology were prepared in transwell inserts (BD Falcon, 8 µm pore size). Bottom membrane was punctured, 100 µL of hydrogel samples were transferred to the center of the plate (pre-equilibrated at 37° C.) and the upper geometry was lowered to a gap height of 0.5 mm. A dynamic time sweep experiment was performed to measure the storage and loss moduli as a function of time for 10 minutes at a constant angular frequency of 6 rad/s and 0.2% strain at 37° C. To determine the recovery ability upon shear-thinning, samples were subjected to 1000% shear for 30 seconds (at frequency 6 rad/s) followed by 1 h dynamic time sweep (6 rad/sec, 0.2% strain).

In vitro release of miRNA from hydrogel composite. Hydrogel composites (containing Peptide 2 or Peptide 3) were prepared in cylindrical glass vials as described previously and had only the top surface exposed to buffer for the release. Each sample were loaded with 1 µg of FAM-labeled scrambled miRNA. 1 mL of HBS (pH 7.4) was added on top of the gels and the vials were agitated at 37° C. (50 rpm). At scheduled time points, the entire supernatant was removed and replaced with 1 mL fresh HBS. To ensure miRNA dissociation from released nanoparticles, heparin was added to the removed supernatant at each time point with a final concentration of 50 µg/mL. Concentrations of released miRNA in the supernatant were determined by measuring fluorescence of the removed aliquot. The FAM fluorophore on miRNA was excited at 490 nm and emission intensity at 520 nm was recorded on a PTI fluorimeter. miRNA concentration was calculated based on a standard curve.

Integrity of hydrogel-released nanoparticle was assessed by monitoring particle size with dynamic light scattering and measuring electrophoretic mobility with agarose gel electrophoresis assay. 0.5% Peptide 3 hydrogel composite was prepared with nanoparticles containing 10 µg of unlabeled scrambled miRNA. 0.4 mL of HBS was added on top of the gels and the vials were agitated at 37° C. (50 rpm). The entire supernatant was removed at day 2 and day 4 and replaced with 0.4 mL fresh HBS. Samples were mixed with 3 µL of 1× loading buffer and loaded on a 2% (w/v) agarose gel containing ethidium bromide and electrophoresed in Tris acetate-EDTA buffer (pH 8.0) for 1 h at 80 V. Samples containing 1 µg of naked miRNA and freshly prepared nanoparticles containing equivalent amount of miRNA were also electrophoresed simultaneously. Images were acquired in a Bio-Rad gel imager.

Cellular transfection and gene silencing with nanoparticles released from hydrogel. To determine the transfection ability nanoparticles released from hydrogel composites, gels containing 0.5% (w/v) Peptide 3 or Peptide 4 were loaded with nanoparticles consisting of 10 µg of FAM-labeled scrambled miRNA. 1 mL of optiMEM was added on top of the gel and the vials were agitated at 37° C. (50 rpm) for 24 h. Release supernatant was collected and incubated with H2052 cells for 4 h. Cells were seeded 4 days before treatment at a density of $5 \times 10^4$ on glass bottom petri dishes. Cells were washed, transferred to complete media and stained with 2 µg/mL Hoechst 33342 for 30 min before imaging with an LSM710 confocal microscope.

To evaluate gene silencing ability of released nanoparticles, gels containing 0.5% (w/v) Peptide 3 were separately loaded with nanoparticles containing miRNA-215 and scrambled miRNA. 1 mL of optiMEM was added on top of the gel and the vials were agitated at 37° C. (50 rpm) for 24 h. Release supernatant was collected and incubated with H2052 cells for 4 h. Cells were seeded 24 h before treatment at a density of $2 \times 10^5$ per well of 6 well glass plates. Media was replaced with fresh complete media after 4 h and cells were allowed to grow for another 44 h. Total RNA was isolated and gene expression was analyzed using qPCR following the previously described protocol.

In vivo studies. Athymic nu/nu mice and NOD/SCIDγ mice were obtained from and raised in a specific pathogen-free environment. All animal studies were approved by the Institutional Animal Care Committee, NIH.

Evaluation of hydrogel composite as an in vivo miRNA depot. For in vivo studies, purified Peptide 1 and Peptide 3 were tested for endotoxin levels using a LAL chromogenic endotoxin quantification kit (Pierce, Rockford, IL). Endotoxin levels were regularly found to be below detection limit. For in vivo miRNA retention study, nanocomposite hydrogels containing 0.5 wt % and 1 wt % (w/v) Peptide 3 were loaded with nanoparticles composed of 10 μg of cy3-labeled scrambled miRNA (Thermo Fisher). Each sample was transferred to sterile 27G syringes and allowed to undergo gelation for 24 h at 37° C. 100 μL of hydrogel was subcutaneously administered to each mouse (n=3) on the lower back. Equivalent amount of naked miRNA solution in HBS was similarly administered as a control (n=2).

Optical imaging. Cy3 fluorescence was longitudinally monitored (1 h, 5 h, day 2, 3, 7, 9, 11, 14 and 24) employing the IVIS spectrum imager (PerkinElmer Inc., Waltham, MA). Imager specific Living Image software (version 4.3.1) was used for image acquisition and analysis. Mice body temperature were kept constant during the procedure with a heated pad located under the anesthesia induction chamber, imaging table, and post procedure recovery cage all maintained at 37° C. All mice were anesthetized in the induction chamber with 3% isoflurane with filtered (0.2 μm) air at 1 liter/minute flow rate for 3-4 minutes and then modified for imaging to 2% with $O_2$ as a carrier with a flow rate 1 liter/minute. Static 2D images were acquired in prone position with the following parameters: excitation filter 570±15 nm, emission filter 620±10 nm, f/stop 2, medium binning (8×8) and auto exposure (typically 1-60 seconds). Circular regions of interest (ROI) were drawn on the injection site to evaluate hydrogel degradation (total radiance efficiency (photons/second/cm2/steradian/mW).

Ultrasound imaging. B-mode ultrasound imaging was performed using the Vevo2100 scanner (Visual Sonics Inc., Toronto, CA) to assess hydrogel degradation serially (provide timepoints). To acquire a 3D volume, multiple 2D B-mode images were captured using the MS 550S (40 MHz) linear array transducer with step size of 0.076 mm while keeping the animal in the prone position. Animal body temperature was maintained at 37° C. and the same anesthesia protocol was followed as described in the optical imaging section. Hydrogel volume (cubic millimeter) was measured using the parallel contour algorithm within the Vevo LAB software 1.7.1 (Visual Sonics Inc., Toronto, CA) at each timepoint.

H & E staining. After US imaging at specific time points, mice were euthanized by $CO_2$ asphyxiation and skin tissue were collected from area at the vicinity of hydrogel injection. Collected tissues were fixed in 10% neutral buffered formalin for 24 h and transferred to 70% ethanol. Sections of 5 μm thickness were generated from paraffin-embedded tissues which were then stained with hematoxylin and eosin for histopathological examination.

Subcutaneous mesothelioma tumor model. Biodistribution. $2\times10^6$ H2373 cells were subcutaneously administered in NOD/SCIDγ mice. Mice were continuously monitored for tumor growth. At each time point, mice were shaved, and a slide caliper was used to measure the length and width of the tumors. Tumor volume was calculated as 0.5×length×$width^2$. To determine the tissue-distribution of delivered miRNA, 200 μL of hydrogel composite loaded with a total of 20 μg cy3 labeled scrambled miRNA was injected peritumorally when tumors reached an average volume of ~250 $mm^3$. Mice similarly injected with blank hydrogel were taken as control to correct for tissue autofluorescence. Whole-body images were acquired 24 h post-injection to monitor cy3 fluorescence. Animals were then sacrificed; tumors and vital organs were collected and imaged. To evaluate intratumoral localization of injected cy3 miRNA, frozen tumors were used to generate 5 μm thick sections which were fixed with 4% formaldehyde in PBS. 1-2 drops of Prolong Gold Antifade Mountant with DAPI (Life Technologies) was added to stain the nuclei and the sections were imaged using an LSM710 confocal microscope.

Tumor growth inhibition. For tumor growth inhibition studies, mice were randomly divided into four treatment groups (n=4-5 in each). When tumors reached an average volume of ~250 $mm^3$, 200 μL of blank hydrogel as well as hydrogel composites (with 20 μg miRNA loaded in each) were administered peritumorally. 1% (w/v) Peptide 3 was used to formulate all hydrogel samples. Only a single injection was performed. One animal from each group was sacrificed on week 4, tumors excised and imaged, while rest of the animals were monitored for another week until average tumor volume for the control groups reach 1000 $mm^3$. Tumors were fixed with formalin and sectioned for immunohistochemistry. Mice were sacrificed by $CO_2$ asphyxiation when any of the tumors began to ulcerate, mice became moribund or if tumor growth hindered eating, urination or defecation.

Immunohistochemistry. To determine extent of apoptosis induced by different formulations, TUNEL assay kit (Promega) was used. Briefly, paraffin-embedded sections were deparaffinized with xylene and rehydrated using an ethanol gradient. Sections were incubated with TUNEL enzyme mix for 1 h following manufacturer's instructions and nuclei were stained using Prolong Gold Antifade Mountant with DAPI.

Expression of anti-proliferative protein ki67 was monitored using immunohistochemistry. Rehydrated tumor sections were immersed in sodium citrate buffer (pH 6.0) and heated at 95° C. for 20 min to retrieve antigen. Sections were blocked using goat serum (10% in Tris Buffered Saline), incubated with rat anti-mouse Ki67 (Clone SolA15) antibody (eBiosciences, 1:100 in blocking buffer) for 1 h followed by a 30-min incubation with Alexa-Fluor 488 anti-rat secondary antibody (1:500 in Tris Buffered Saline). Nuclei were stained using Prolong Gold Antifade Mountant with DAPI.

qPCR for gene expression analysis in vivo. In a separate experiment, mice bearing subcutaneous H2373 tumors with an average volume of ~250 $mm^3$ were peritumorally administered with 200 μL hydrogel composites containing scrambled miRNA and miRNA-215, respectively (with 20 μg miRNA loaded in each). Three animals from each group was sacrificed on week 1 and remaining three animals on week 2. Tumors were excised, and total RNA was isolated using a standard protocol. Gene expression was analyzed using qPCR as described before. U6 snRNA was used as an endogenous control to determine in vivo transfection of miRNA-215. β-actin was used as a control for analyzing gene expressions of miRNA-215 targets, e.g., LMNB2, CDC7, MDM2 and MAD2L1.

Orthotopic mesothelioma tumor model. For orthotopic tumor growth inhibition studies, $1\times10^6$ H2373 cells stably expressing luciferase gene were intraperitoneally administered in NOD/SCIDγ mice (6-8-week-old). Cells were pre-transfected with luciferase reporter vector pGL4.51 [luc2/CMV/Neo] (Promega). Transfected cells expressing luciferase reporter and neomycin-resistance gene were selected under G418-conditioned media. One week after tumor cell inoculation, mice were randomly divided into four treatment groups (n=8-10 in each). 400 µL of blank Peptide 3 hydrogel as well as hydrogel composites containing different nanoparticle formulations (with 40 µg miRNA in each) were administered intraperitoneally. 1% (w/v) Peptide 3 was used to formulate all hydrogel samples. Luciferase signal in the peritoneal cavity was monitored weekly for three weeks by intraperitoneal administration of 200 µL of D-luciferin potassium salt solution (Regis Technologies) immediately before imaging and mice were continuously observed to track survival. Similar protocol was followed for orthotopic tumor model established with intraperitoneally administered H2052 cells where 5 animals were taken in each treatment group.

Statistical analysis. Data are expressed as mean±SD except for tumor growth inhibition related experiments where mean±SEM has been used. Statistical analysis to compare data between two groups was performed using two-tailed Student's t-tests, with either Microsoft Excel or GraphPad Prism 7.0 Software. In experiments investigating cellular uptake mechanism, one-way ANOVA followed by Dunnett's multiple comparison test was used to compare among multiple groups. $p<0.05$ was considered statistically significant. Significance is denoted as * for $p<0.05$,  for $p<0.01$, * for $p<0.001$ and # for $p<0.0001$. Mice were randomly divided into groups. No blinding was used.

Example 2

Peptide Conformation Alters Functionality of miRNA Nanoparticles

The conformational state of the peptide used to form the miRNA nanoparticle is important for the proper function of the ultimate nanoparticle-hydrogel composite material. The complexation of unfolded (random coil) peptide to miRNA produces nanoparticles that are effectively taken up by cells.

In contrast (and surprisingly), if the peptide complexed with the miRNA is allowed to fold into a β-hairpin conformation prior to complexation with the miRNA to form the nanoparticles, the resulting nanoparticles are ineffective at delivering functional miRNA to cells. FIG. 24 shows that MAX1:miRNA-215 nanoparticles formed by MAX1 in a β-hairpin conformation are unable to silence miRNA-215 responsive genes. This is unexpected behavior and non-obvious, as the conformation of MAX1 complexed to RNA a priori would not be predicted to have an effect on gene silencing activity.

To determine gene silencing ability of MAX1:miRNA nanoparticles prepared using natively folded β-hairpin MAX1, 25 µL of a 150 µM MAX1 solution in HBS (25 mM HEPES 150 mM NaCl, pH 7.4) is added to a 25 µL of a 3 µM solution of miRNA in HBS. The resulting suspension is incubated for 30 min at 37° C. with constant agitation to form the MAX1:miRNA nanoparticles where MAX1 peptide remains in a β-hairpin conformation. $2 \times 10^5$ H2052 cells were seeded on 6 well plate one day before treatment and allowed to grow under normal culture conditions. Nanoparticles were diluted with optiMEM to a final miRNA concentration of 40 nM. Cells were incubated with nanoparticles for 4 h, the media was discarded and fresh complete media was added to allow cellular growth under normal culture condition for another 48 h. Total RNA was isolated from cells using TRIzol™ (Thermo Fisher) following standard protocol. Briefly, 1 mL of TRIzol™ solution was used to lyse cells in each well. Collected suspension was mixed with 0.2 mL chloroform (HPLC grade), centrifuged at 12,000 g for 20 minutes at 4° C. and the transparent upper layer was collected. RNA was precipitated from the upper aqueous layer by incubating with 0.5 mL of molecular biology grade isopropanol for 15 minutes followed by centrifugation. Isolated RNA was washed with 70% ethanol and resuspended in RNase free water. RNA concentration and purity were determined in a Nanodrop™ 2000 spectrophotometer. cDNA from each treatment group was synthesized using High-Capacity cDNA Reverse Transcription Kit (Applied Biosystems) and mRNA expression levels for CDC7, LMNB2, MDM2 and MAD2L1 were determined using corresponding TAQ-MAN probes (Thermo Fisher) on QuantStudio 6 Flex Real-Time PCR System (Applied Biosystems). Mean values for each gene was normalized to β-actin as a housekeeping control.

It will be apparent that the precise details of the methods or compositions described may be varied or modified without departing from the spirit of the described embodiments. We claim all such modifications and variations that fall within the scope and spirit of the claims below.

It is claimed:

1. A peptide hydrogel, comprising:
   nanoparticles encapsulated within the peptide hydrogel, wherein the nanoparticles comprise a nucleic acid molecule complexed with a first amphiphilic cationic β-hairpin peptide that is unfolded and not in a β-hairpin conformation, and wherein:
   the peptide hydrogel is formed from a fibrillar network of a second amphiphilic cationic β-hairpin peptide that is folded in a β-hairpin conformation;
   the peptide hydrogel undergoes shear-thinning upon application of shear stress, and rheological recovery upon removal of the shear stress;
   the nucleic acid molecule is an antisense nucleic acid molecule;
   a net electrostatic charge of the first amphiphilic cationic β-hairpin peptide is equal to or more positive than a net electrostatic charge of the second amphiphilic cationic β-hairpin peptide at neutral pH;
   the first amphiphilic cationic β-hairpin peptide comprises or consists of an amino acid sequence set forth as: VKVKVKVKV$^D$PPTKVKVKVKV-NH$_2$; and
   the second amphiphilic cationic β-hairpin peptide comprises or consists of an amino acid sequence set forth as: VLTKVKTKV$^D$PPTKVEVKVLV-NH$_2$.

2. The peptide hydrogel of claim 1, wherein the N-terminus of the first and/or second amphiphilic cationic β-hairpin peptide is acetylated, and/or wherein the C-terminus of the first and/or second amphiphilic cationic β-hairpin peptide is amidated.

3. The peptide hydrogel of claim 1, wherein the nucleic acid molecule is a microRNA or a mimic and/or mimetic thereof.

4. The peptide hydrogel of claim 3, wherein the nucleic acid molecule is any one of:
   hsa-miR-1, hsa-miR-7, hsa-miR-10a, hsa-miR-15, hsa-miR-16, hsa-miR-23a-3p, hsa-miR-24-1, hsa-miR-24-2-5p, hsa-miR-26a, hsa-miR-26b, hsa-miR-27a-5p, hsa-miR-27b-5p, hsa-miR-27b-3p, hsa-miR-29a, hsa-miR-29b, hsa-miR-29c, hsa-miR-30b-5p, hsa-miR-30c-1, hsa-miR-33a, hsa-miR-34a, hsa-miR-95, hsa-miR-96, hsa-miR-100, hsa-miR-125a, hsa-miR-127, hsa-miR-130a, hsa-miR-130b, hsa-miR-132-3p, hsa-miR-133b, hsa-miR-134, hsa-miR-135a-1, hsa-miR-136, hsa-miR-139, hsa-miR-143, hsa-miR-145, hsa-miR-148a, hsa-miR-149, hsa-miR-181c, hsa-miR-181d, hsa-miR-182, hsa-mir-183, hsa-miR-190, hsa-miR-190b, hsa-miR-192, hsa-miR-195, hsa-miR-194, hsa-miR-200, hsa-miR-206, hsa-miR-212, hsa-miR- 215, hsa-miR-221, hsa-miR-222-3p, hsa-miR-320d-1, hsa-miR-342, hsa-miR-370, hsa-miR-375, hsa-miR-376a-1, hsa-miR-376b, hsa-miR-491, hsa-miR-497, hsa-miR-502, hsa-miR-506, hsa-miR-509-1, hsa-miR-548, hsa-miR-643, hsa-miR-653, hsa-miR-664, hsa-miR-668, hsa-miR-676, hsa-miR-939, hsa-miR-1245, hsa-miR-1287, hsa-miR-1293, hsa-miR-1294, hsa-miR-1538, hsa-miR-2114, hsa-miR-3145, hsa-miR-3610, hsa-miR-3677, hsa-let-7c-5p, hsa-miR-590-3p, hsa-miR-4472-1, hsa-miR-8078, hsa-miR-4675, hsa-mir-155, hsa-mir-196b, hsa-mir-4524a, or hsa-mir-4524b; or a mimic and/or mimetic thereof.

5. The peptide hydrogel of claim 1, further comprising a heterologous anti-cancer agent dispersed within the peptide hydrogel.

6. The peptide hydrogel of claim 5, wherein the heterologous anti-cancer agent is a chemotherapeutic agent.

7. The peptide hydrogel of claim 1, comprising:
a storage modulus of greater than 40 Pascal in the absence of shear;
from about 10 mM to about 400 mM NaCl and a pH of from about 7.0 to about 9.0; and/or
from about 0.25% to about 4.0% w/v of the second amphiphilic cationic β-hairpin; peptide.

8. The peptide hydrogel of claim 7, comprising about 150 mM NaCl and a pH of about 7.4, and/or from about 0.5% to about 2.0% w/v second amphiphilic cationic β-hairpin peptide.

9. A peptide hydrogel, comprising:
nanoparticles encapsulated within the peptide hydrogel, wherein the nanoparticles comprise a nucleic acid molecule complexed with a first amphiphilic cationic β-hairpin peptide that is unfolded and not in a β-hairpin conformation, and wherein:
the peptide hydrogel is formed from a fibrillar network of a second amphiphilic cationic β-hairpin peptide that is in a β-hairpin conformation;
the first amphiphilic cationic β-hairpin peptide comprises or consists of an amino acid sequence set forth as: VKVKVKVKV$^D$PPTKVKVKVKV-NH$_2$; and
the second amphiphilic cationic β-hairpin peptide comprises or consists of an amino acid sequence set forth as: VLTKVKTKV$^D$PPTKVEVKVLV-NH$_2$.

10. The peptide hydrogel of claim 9, wherein the nucleic acid molecule is a microRNA or a mimic and/or mimetic thereof.

11. The peptide hydrogel of claim 10, wherein the nucleic acid molecule is any one of:
hsa-miR-1, hsa-miR-7, hsa-miR-10a, hsa-miR-15, hsa-miR-16, hsa-miR-23a-3p, hsa-miR-24-1, hsa-miR-24-2-5p, hsa-miR-26a, hsa-miR-26b, hsa-miR-27a-5p, hsa-miR-27b-5p, hsa-miR-27b-3p, hsa-miR-29a, hsa-miR-29b, hsa-miR-29c, hsa-miR-30b-5p, hsa-miR-30c-1, hsa-miR-33a, hsa-miR-34a, hsa-miR-95, hsa-miR-96, hsa-miR-100, hsa-miR-125a, hsa-miR-127, hsa-miR-130a, hsa-miR-130b, hsa-miR-132-3p, hsa-miR-133b, hsa-miR-134, hsa-miR-135a-1, hsa-miR-136, hsa-miR-139, hsa-miR-143, hsa-miR-145, hsa-miR-148a, hsa-miR-149, hsa-miR-181c, hsa-miR-181d, hsa-miR-182, hsa-mir-183, hsa-miR-190, hsa-miR-190b, hsa-miR-192, hsa-miR-195, hsa-miR-194, hsa-miR-200, hsa-miR-206, hsa-miR-212, hsa-miR-215, hsa-miR-221, hsa-miR-222-3p, hsa-miR-320d-1, hsa-miR-342, hsa-miR-370, hsa-miR-375, hsa-miR-376a-1, hsa-miR-376b, hsa-miR-491, hsa-miR-497, hsa-miR-502, hsa-miR-506, hsa-miR-509-1, hsa-miR-548, hsa-miR-643, hsa-miR-653, hsa-miR-664, hsa-miR-668, hsa-miR-676, hsa-miR-939, hsa-miR-1245, hsa-miR-1287, hsa-miR-1293, hsa-miR-1294, hsa-miR-1538, hsa-miR-2114, hsa-miR-3145, hsa-miR-3610, hsa-miR-3677, hsa-let-7c-5p, hsa-miR-590-3p, hsa-miR-4472-1, hsa-miR-8078, hsa-miR-4675, hsa-mir-155, hsa-mir-196b, hsa-mir-4524a, or hsa-mir-4524b; or a mimic and/or mimetic thereof.

12. The peptide hydrogel of claim 9, wherein the first and second amphiphilic cationic β-hairpin peptides are no more than 50 amino acids in length.

13. The peptide hydrogel of claim 9, wherein a net electrostatic charge of the first amphiphilic cationic β-hairpin peptide is equal to or more positive than a net electrostatic charge of the second amphiphilic cationic β-hairpin peptide at neutral pH.

14. The peptide hydrogel of claim 13, wherein the net electrostatic charge of the first amphiphilic β-hairpin cationic peptide is from +7 to +10 and the net electrostatic charge of the second amphiphilic cationic β-hairpin peptide is from +3 to +8 at neutral pH.

15. The peptide hydrogel of claim 14, wherein the net electrostatic charge of the first amphiphilic β-hairpin cationic peptide is +9 and the net electrostatic charge of the second amphiphilic cationic β-hairpin peptide is +5 at neutral pH.

16. The peptide hydrogel of claim 9, wherein
the C-terminus of the first amphiphilic cationic β-hairpin peptide is not carboxylate and comprises a peptide modification having a neutral or positive charge.

17. The peptide hydrogel of claim 16, wherein
the first amphiphilic cationic β-hairpin peptide has a net formal charge of from +7 to +10 at neutral pH.

18. The peptide hydrogel of claim 9, wherein
the second amphiphilic cationic β-hairpin peptide has a net formal charge of from +3 to +8 at neutral pH.

19. The peptide hydrogel of claim 9, further comprising a heterologous anti-cancer agent dispersed within the peptide hydrogel.

20. The peptide hydrogel of claim 19, wherein the heterologous anti-cancer agent is a chemotherapeutic agent.

21. The peptide hydrogel of claim 9, wherein the nucleic acid molecule is an antisense nucleic acid molecule.

22. The peptide hydrogel of claim 9, wherein the hydrogel undergoes shear-thinning upon application of shear stress, and rheological recovery upon removal of the shear stress.

23. A syringe, containing the peptide hydrogel of claim 9.

24. A peptide hydrogel, comprising:
nanoparticles encapsulated within the peptide hydrogel, wherein the nanoparticles comprise an antisense nucleic acid molecule complexed with a first amphiphilic cationic β-hairpin peptide that is unfolded and not in a β-hairpin conformation, and wherein:
the peptide hydrogel is formed from a fibrillar network of a second amphiphilic cationic β-hairpin peptide that is folded in a β-hairpin conformation;
the peptide hydrogel undergoes shear-thinning upon application of shear stress, and rheological recovery upon removal of the shear stress;
the first amphiphilic cationic β-hairpin peptide consists of an amino acid sequence set forth as: VKVKVKVKV$^D$PPTKVKVKVKV-NH$_2$; and
the second amphiphilic cationic β-hairpin peptide consists of an amino acid sequence set forth as: VLTKVKTKV$^D$PPTKVEVKVLV-NH$_2$.

25. A method of administrating a nucleic acid molecule to a subject, comprising administering the peptide hydrogel of claim 9 to a target location in the subject.

26. A method of treating or inhibiting a cancer in a subject, comprising:
administering an effective amount of the peptide hydrogel of claim 9 to a target location in the subject where the cancer is present or is at risk of being present; and
wherein the nucleic acid molecule inhibits the cancer.

27. The method of claim 26, wherein the nucleic acid molecule is a mircoRNA, or a mimic and/or mimetic thereof, that inhibits the cancer.

28. The method of claim 26, wherein the target location is a serosal surface lined by mesothelial cells in the subject where the cancer is present or is at risk of being present.

29. The method of claim 28, wherein the serosal surface is part of a serosal body cavity in the subject, optionally wherein the serosal body cavity is a pleural cavity, a pericardial cavity, an anterior mediastinal cavity, a posterior mediastinal cavity, a peritoneal cavity, or a *tunica vaginalis* testis cavity.

30. The method of claim 26, wherein the cancer is a serosal neoplasm, optionally wherein the serosal neoplasm is any one of a pleural mesothelioma, a peritoneal mesothelioma, a thymic epithelial cancer, an ovarian carcinoma, a cervical cancer, a small-cell lung carcinoma, a non-small-cell lung carcinoma, an ovarian carcinoma, an appendiceal cancer, or a glioma, and/or a metastatic growth of a primary tumor that metastasized to a serosal surface in the subject.

31. The method of claim 26, wherein administering the peptide hydrogel to the subject comprises injection or spray delivery of the peptide hydrogel to coat all or a portion of the serosal surface in the subject where the cancer is present or is at risk of being present.

32. The method of claim 26, wherein:
the cancer is malignant pleural mesothelioma;
administering the peptide hydrogel to the subject comprises injection or spray delivery of the peptide hydrogel to coat a pleural surface in a plural cavity in the subject where the pleural mesothelioma is present or is at risk of being present; and
the microRNA is one or more of hsa-miR-1, hsa-miR-7, hsa-miR-10a, hsa-miR-15, hsa-miR-16, hsa-miR-23a-3p, hsa-miR-24-1, hsa-miR-24-2-5p, hsa-miR-26a, hsa-miR-26b, hsa-miR-27a-5p, hsa-miR-27b-5p, hsa-miR-27b-3p, hsa-miR-29a, hsa-miR-29b, hsa-miR-29c, hsa-miR-30b-5p, hsa-miR-30c-1, hsa-miR-33a, hsa-miR-34a, hsa-miR-95, hsa-miR-96, hsa-miR-100, hsa-miR-125a, hsa-miR-127, hsa-miR-130a, hsa-miR-130b, hsa-miR-132-3p, hsa-miR-133b, hsa-miR-134, hsa-miR-135a-1, hsa-miR-136, hsa-miR-139, hsa-miR-143, hsa-miR-145, hsa-miR-148a, hsa-miR-149, hsa-miR-181c, hsa-miR-181d, hsa-miR-182, hsa-mir-183, hsa-miR-190, hsa-miR-190b, hsa-miR-192, hsa-miR-195, hsa-miR-194, hsa-miR-200, hsa-miR-206, hsa-miR-212, hsa-miR-215, hsa-miR-221, hsa-miR-222-3p, hsa-miR-320d-1, hsa-miR-342, hsa-miR-370, hsa-miR-375, hsa-miR-376a-1, hsa-miR-376b, hsa-miR-491, hsa-miR-497, hsa-miR-502, hsa-miR-506, hsa-miR-509-1, hsa-miR-548, hsa-miR-643, hsa-miR-653, hsa-miR-664, hsa-miR-668, hsa-miR-676, hsa-miR-939, hsa-miR-1245, hsa-miR-1287, hsa-miR-1293, hsa-miR-1294, hsa-miR-1538, hsa-miR-2114, hsa-miR-3145, hsa-miR-3610, and hsa-miR-3677.

\* \* \* \* \*

SEQUENCE LISTING

```
<160> NUMBER OF SEQ ID NOS: 94

<210> SEQ ID NO 1
<211> LENGTH: 24
<212> TYPE: PRT
<213> ORGANISM: Artificial Sequence
<220> FEATURE:
<223> OTHER INFORMATION: B-hairpin peptide sequence
<220> FEATURE:
<221> NAME/KEY: misc_feature
<222> LOCATION: (1)..(1)
<223> OTHER INFORMATION: Xaa can be any one of F, I, L, M, T, V, W, and
      Y, or is not present
<220> FEATURE:
<221> NAME/KEY: misc_feature
<222> LOCATION: (2)..(2)
<223> OTHER INFORMATION: Xaa can be any one of H, K, Ornithine, and R,
      or is not present if X1 is not present
```

```
<220> FEATURE:
<221> NAME/KEY: misc_feature
<222> LOCATION: (3)..(3)
<223> OTHER INFORMATION: Xaa can be any one of F, I, L, M, T, V, W, and
      Y, or is not present
<220> FEATURE:
<221> NAME/KEY: misc_feature
<222> LOCATION: (4)..(4)
<223> OTHER INFORMATION: Xaa can be any one of H, K, Ornithine, and R,
      or is not present if X3 is not present
<220> FEATURE:
<221> NAME/KEY: misc_feature
<222> LOCATION: (5)..(5)
<223> OTHER INFORMATION: Xaa can be any one of F, I, L, M, T, V, W, and
      Y
<220> FEATURE:
<221> NAME/KEY: misc_feature
<222> LOCATION: (6)..(6)
<223> OTHER INFORMATION: Xaa can be any one of H, K, Ornithine, and R
<220> FEATURE:
<221> NAME/KEY: misc_feature
<222> LOCATION: (7)..(7)
<223> OTHER INFORMATION: Xaa can be any one of F, I, L, M, T, V, W, and
      Y
<220> FEATURE:
<221> NAME/KEY: misc_feature
<222> LOCATION: (8)..(8)
<223> OTHER INFORMATION: Xaa can be any one of H, K, Ornithine, and R
<220> FEATURE:
<221> NAME/KEY: misc_feature
<222> LOCATION: (9)..(9)
<223> OTHER INFORMATION: Xaa can be any one of F, I, L, M, T, V, W, and
      Y
<220> FEATURE:
<221> NAME/KEY: misc_feature
<222> LOCATION: (10)..(10)
<223> OTHER INFORMATION: Xaa can be any one of H, K, Ornithine, and R
<220> FEATURE:
<221> NAME/KEY: misc_feature
<222> LOCATION: (11)..(11)
<223> OTHER INFORMATION: Xaa can be any one of F, I, L, M, T, V, W, and
      Y
<220> FEATURE:
<221> NAME/KEY: misc_feature
<222> LOCATION: (14)..(14)
<223> OTHER INFORMATION: Xaa can be any one of F, I, L, M, T, V, W, and
      Y
<220> FEATURE:
<221> NAME/KEY: misc_feature
<222> LOCATION: (15)..(15)
<223> OTHER INFORMATION: Xaa can be any one of H, K, Ornithine, and R
<220> FEATURE:
<221> NAME/KEY: misc_feature
<222> LOCATION: (16)..(16)
<223> OTHER INFORMATION: Xaa can be any one of F, I, L, M, T, V, W, and
      Y
<220> FEATURE:
<221> NAME/KEY: misc_feature
<222> LOCATION: (17)..(17)
<223> OTHER INFORMATION: Xaa can be any one of H, K, Ornithine, and R
<220> FEATURE:
<221> NAME/KEY: misc_feature
<222> LOCATION: (18)..(18)
<223> OTHER INFORMATION: Xaa can be any one of F, I, L, M, T, V, W, and
      Y
<220> FEATURE:
<221> NAME/KEY: misc_feature
<222> LOCATION: (19)..(19)
<223> OTHER INFORMATION: Xaa can be any one of H, K, Ornithine, and R
<220> FEATURE:
<221> NAME/KEY: misc_feature
<222> LOCATION: (20)..(20)
<223> OTHER INFORMATION: Xaa can be any one of F, I, L, M, T, V, W, and
      Y
<220> FEATURE:
<221> NAME/KEY: misc_feature
<222> LOCATION: (21)..(21)
<223> OTHER INFORMATION: Xaa can be any one of H, K, Ornithine, and R,
      or is not present if X3 is not present
```

```
<220> FEATURE:
<221> NAME/KEY: misc_feature
<222> LOCATION: (22)..(22)
<223> OTHER INFORMATION: Xaa can be any one of F, I, L, M, T, V, W, and
      Y, or is not present if X3 is not present
<220> FEATURE:
<221> NAME/KEY: misc_feature
<222> LOCATION: (23)..(23)
<223> OTHER INFORMATION: Xaa can be any one of H, K, Ornithine, and R,
      or is not present if X1 is not present
<220> FEATURE:
<221> NAME/KEY: misc_feature
<222> LOCATION: (24)..(24)
<223> OTHER INFORMATION: Xaa can be any one of F, I, L, M, T, V, W, and
      Y, or is not present if X1 is not present

<400> SEQUENCE: 1

Xaa Xaa Xaa Xaa Xaa Xaa Xaa Xaa Xaa Xaa Xaa Asn Gly Xaa Xaa Xaa
1               5                   10                  15

Xaa Xaa Xaa Xaa Xaa Xaa Xaa Xaa
            20

<210> SEQ ID NO 2
<211> LENGTH: 20
<212> TYPE: PRT
<213> ORGANISM: Artificial Sequence
<220> FEATURE:
<223> OTHER INFORMATION: B-hairpin peptide sequence

<400> SEQUENCE: 2

Val Lys Val Lys Val Lys Val Lys Val Asn Gly Thr Lys Val Lys Val
1               5                   10                  15

Lys Val Lys Val
            20

<210> SEQ ID NO 3
<211> LENGTH: 22
<212> TYPE: RNA
<213> ORGANISM: HOMO SAPIENS

<400> SEQUENCE: 3
acauacuucu uuauaugccc au                                              22

<210> SEQ ID NO 4
<211> LENGTH: 23
<212> TYPE: RNA
<213> ORGANISM: HOMO SAPIENS

<400> SEQUENCE: 4
uggaagacua gugauuuugu ugu                                             23

<210> SEQ ID NO 5
<211> LENGTH: 23
<212> TYPE: RNA
<213> ORGANISM: HOMO SAPIENS

<400> SEQUENCE: 5
uacccuguag auccgaauuu gug                                             23

<210> SEQ ID NO 6
<211> LENGTH: 22
<212> TYPE: RNA
<213> ORGANISM: HOMO SAPIENS

<400> SEQUENCE: 6
uagcagcaca uaaugguuug ug                                              22
```

```
<210> SEQ ID NO 7
<211> LENGTH: 22
<212> TYPE: RNA
<213> ORGANISM: HOMO SAPIENS

<400> SEQUENCE: 7
uagcagcacg uaaauauugg cg                                              22

<210> SEQ ID NO 8
<211> LENGTH: 21
<212> TYPE: RNA
<213> ORGANISM: HOMO SAPIENS

<400> SEQUENCE: 8
aucacauugc cagggauuuc c                                               21

<210> SEQ ID NO 9
<211> LENGTH: 22
<212> TYPE: RNA
<213> ORGANISM: HOMO SAPIENS

<400> SEQUENCE: 9
ugccuacuga gcugauauca gu                                              22

<210> SEQ ID NO 10
<211> LENGTH: 22
<212> TYPE: RNA
<213> ORGANISM: HOMO SAPIENS

<400> SEQUENCE: 10
ugccuacuga gcugaaacac ag                                              22

<210> SEQ ID NO 11
<211> LENGTH: 22
<212> TYPE: RNA
<213> ORGANISM: HOMO SAPIENS

<400> SEQUENCE: 11
uucaaguaau ccaggauagg cu                                              22

<210> SEQ ID NO 12
<211> LENGTH: 21
<212> TYPE: RNA
<213> ORGANISM: HOMO SAPIENS

<400> SEQUENCE: 12
uucaaguaau ucaggauagg u                                               21

<210> SEQ ID NO 13
<211> LENGTH: 22
<212> TYPE: RNA
<213> ORGANISM: HOMO SAPIENS

<400> SEQUENCE: 13
agggcuuagc ugcuugugag ca                                              22

<210> SEQ ID NO 14
<211> LENGTH: 22
<212> TYPE: RNA
<213> ORGANISM: HOMO SAPIENS

<400> SEQUENCE: 14
```

-continued

```
agagcuuagc ugauggguga ac                                              22

<210> SEQ ID NO 15
<211> LENGTH: 21
<212> TYPE: RNA
<213> ORGANISM: HOMO SAPIENS

<400> SEQUENCE: 15
uucacagugg cuaaguucug c                                               21

<210> SEQ ID NO 16
<211> LENGTH: 22
<212> TYPE: RNA
<213> ORGANISM: HOMO SAPIENS

<400> SEQUENCE: 16
acugauuucu uuugguguuc ag                                              22

<210> SEQ ID NO 17
<211> LENGTH: 24
<212> TYPE: RNA
<213> ORGANISM: HOMO SAPIENS

<400> SEQUENCE: 17
gcugguuuca uauggugguu uaga                                            24

<210> SEQ ID NO 18
<211> LENGTH: 22
<212> TYPE: RNA
<213> ORGANISM: HOMO SAPIENS

<400> SEQUENCE: 18
ugaccgauuu cuccuggugu uc                                              22

<210> SEQ ID NO 19
<211> LENGTH: 22
<212> TYPE: RNA
<213> ORGANISM: HOMO SAPIENS

<400> SEQUENCE: 19
uguaaacauc cuacacucag cu                                              22

<210> SEQ ID NO 20
<211> LENGTH: 23
<212> TYPE: RNA
<213> ORGANISM: HOMO SAPIENS

<400> SEQUENCE: 20
uguaaacauc cuacacucuc agc                                             23

<210> SEQ ID NO 21
<211> LENGTH: 21
<212> TYPE: RNA
<213> ORGANISM: HOMO SAPIENS

<400> SEQUENCE: 21
gugcauugua guugcauugc a                                               21

<210> SEQ ID NO 22
<211> LENGTH: 22
<212> TYPE: RNA
<213> ORGANISM: HOMO SAPIENS

<400> SEQUENCE: 22
```
uggcaguguc uuagcugguu gu         22

<210> SEQ ID NO 23
<211> LENGTH: 21
<212> TYPE: RNA
<213> ORGANISM: HOMO SAPIENS

<400> SEQUENCE: 23
ucaauaaaug ucuguugaau u          21

<210> SEQ ID NO 24
<211> LENGTH: 23
<212> TYPE: RNA
<213> ORGANISM: HOMO SAPIENS

<400> SEQUENCE: 24
uuuggcacua gcacauuuuu gcu        23

<210> SEQ ID NO 25
<211> LENGTH: 22
<212> TYPE: RNA
<213> ORGANISM: HOMO SAPIENS

<400> SEQUENCE: 25
aacccguaga uccgaacuug ug         22

<210> SEQ ID NO 26
<211> LENGTH: 24
<212> TYPE: RNA
<213> ORGANISM: HOMO SAPIENS

<400> SEQUENCE: 26
ucccugagac ccuuuaaccu guga       24

<210> SEQ ID NO 27
<211> LENGTH: 22
<212> TYPE: RNA
<213> ORGANISM: HOMO SAPIENS

<400> SEQUENCE: 27
cugaagcuca gagggcucug au         22

<210> SEQ ID NO 28
<211> LENGTH: 22
<212> TYPE: RNA
<213> ORGANISM: HOMO SAPIENS

<400> SEQUENCE: 28
uucacauugu gcuacugucu gc         22

<210> SEQ ID NO 29
<211> LENGTH: 21
<212> TYPE: RNA
<213> ORGANISM: HOMO SAPIENS

<400> SEQUENCE: 29
acucuuuccc uguugcacua c          21

<210> SEQ ID NO 30
<211> LENGTH: 22
<212> TYPE: RNA
<213> ORGANISM: HOMO SAPIENS

```
<400> SEQUENCE: 30
uaacagucua cagccauggu cg                                              22

<210> SEQ ID NO 31
<211> LENGTH: 22
<212> TYPE: RNA
<213> ORGANISM: HOMO SAPIENS

<400> SEQUENCE: 31
uuuggucccc uucaaccagc ua                                              22

<210> SEQ ID NO 32
<211> LENGTH: 22
<212> TYPE: RNA
<213> ORGANISM: HOMO SAPIENS

<400> SEQUENCE: 32
ugugacuggu ugaccagagg gg                                              22

<210> SEQ ID NO 33
<211> LENGTH: 23
<212> TYPE: RNA
<213> ORGANISM: HOMO SAPIENS

<400> SEQUENCE: 33
uauggcuuuu uauuccuaug uga                                             23

<210> SEQ ID NO 34
<211> LENGTH: 23
<212> TYPE: RNA
<213> ORGANISM: HOMO SAPIENS

<400> SEQUENCE: 34
acuccauuug uuuugaugau gga                                             23

<210> SEQ ID NO 35
<211> LENGTH: 23
<212> TYPE: RNA
<213> ORGANISM: HOMO SAPIENS

<400> SEQUENCE: 35
ucuacagugc acgugucucc agu                                             23

<210> SEQ ID NO 36
<211> LENGTH: 22
<212> TYPE: RNA
<213> ORGANISM: HOMO SAPIENS

<400> SEQUENCE: 36
ggugcagugc ugcaucucug gu                                              22

<210> SEQ ID NO 37
<211> LENGTH: 23
<212> TYPE: RNA
<213> ORGANISM: HOMO SAPIENS

<400> SEQUENCE: 37
guccaguuuu cccaggaauc ccu                                             23

<210> SEQ ID NO 38
<211> LENGTH: 22
<212> TYPE: RNA
<213> ORGANISM: HOMO SAPIENS
```

-continued

```
<400> SEQUENCE: 38
aaaguucuga gacacuccga cu                                           22

<210> SEQ ID NO 39
<211> LENGTH: 23
<212> TYPE: RNA
<213> ORGANISM: HOMO SAPIENS

<400> SEQUENCE: 39
ucuggcuccg ugucuucacu ccc                                          23

<210> SEQ ID NO 40
<211> LENGTH: 22
<212> TYPE: RNA
<213> ORGANISM: HOMO SAPIENS

<400> SEQUENCE: 40
aacauucaac cugucgguga gu                                           22

<210> SEQ ID NO 41
<211> LENGTH: 23
<212> TYPE: RNA
<213> ORGANISM: HOMO SAPIENS

<400> SEQUENCE: 41
aacauucauu guugucggug ggu                                          23

<210> SEQ ID NO 42
<211> LENGTH: 24
<212> TYPE: RNA
<213> ORGANISM: HOMO SAPIENS

<400> SEQUENCE: 42
uuuggcaaug guagaacuca cacu                                         24

<210> SEQ ID NO 43
<211> LENGTH: 22
<212> TYPE: RNA
<213> ORGANISM: HOMO SAPIENS

<400> SEQUENCE: 43
uauggcacug guagaauuca cu                                           22

<210> SEQ ID NO 44
<211> LENGTH: 22
<212> TYPE: RNA
<213> ORGANISM: HOMO SAPIENS

<400> SEQUENCE: 44
ugauauguuu gauauauuag gu                                           22

<210> SEQ ID NO 45
<211> LENGTH: 21
<212> TYPE: RNA
<213> ORGANISM: HOMO SAPIENS

<400> SEQUENCE: 45
ugauauguuu gauauugggu u                                            21

<210> SEQ ID NO 46
<211> LENGTH: 21
<212> TYPE: RNA
```

-continued

<213> ORGANISM: HOMO SAPIENS

<400> SEQUENCE: 46
cugaccuaug aauugacagc c                                              21

<210> SEQ ID NO 47
<211> LENGTH: 21
<212> TYPE: RNA
<213> ORGANISM: HOMO SAPIENS

<400> SEQUENCE: 47
uagcagcaca gaaauauugg c                                              21

<210> SEQ ID NO 48
<211> LENGTH: 22
<212> TYPE: RNA
<213> ORGANISM: HOMO SAPIENS

<400> SEQUENCE: 48
uguaacagca acuccaugug ga                                             22

<210> SEQ ID NO 49
<211> LENGTH: 22
<212> TYPE: RNA
<213> ORGANISM: HOMO SAPIENS

<400> SEQUENCE: 49
caucuuaccg gacagugcug ga                                             22

<210> SEQ ID NO 50
<211> LENGTH: 22
<212> TYPE: RNA
<213> ORGANISM: HOMO SAPIENS

<400> SEQUENCE: 50
uggaauguaa ggaagugugu gg                                             22

<210> SEQ ID NO 51
<211> LENGTH: 23
<212> TYPE: RNA
<213> ORGANISM: HOMO SAPIENS

<400> SEQUENCE: 51
accuuggcuc uagacugcuu acu                                            23

<210> SEQ ID NO 52
<211> LENGTH: 21
<212> TYPE: RNA
<213> ORGANISM: HOMO SAPIENS

<400> SEQUENCE: 52
augaccuaug aauugacaga c                                              21

<210> SEQ ID NO 53
<211> LENGTH: 22
<212> TYPE: RNA
<213> ORGANISM: HOMO SAPIENS

<400> SEQUENCE: 53
accuggcaua caauguagau uu                                             22

<210> SEQ ID NO 54
<211> LENGTH: 21

```
<212> TYPE: RNA
<213> ORGANISM: HOMO SAPIENS

<400> SEQUENCE: 54
agcuacaucu ggcuacuggg u                                             21

<210> SEQ ID NO 55
<211> LENGTH: 19
<212> TYPE: RNA
<213> ORGANISM: HOMO SAPIENS

<400> SEQUENCE: 55
aaaagcuggg uugagagga                                                19

<210> SEQ ID NO 56
<211> LENGTH: 22
<212> TYPE: RNA
<213> ORGANISM: HOMO SAPIENS

<400> SEQUENCE: 56
caggucacgu cucugcaguu ac                                            22

<210> SEQ ID NO 57
<211> LENGTH: 22
<212> TYPE: RNA
<213> ORGANISM: HOMO SAPIENS

<400> SEQUENCE: 57
uuuguucguu cggcucgcgu ga                                            22

<210> SEQ ID NO 58
<211> LENGTH: 21
<212> TYPE: RNA
<213> ORGANISM: HOMO SAPIENS

<400> SEQUENCE: 58
aggggugcua ucugugauug a                                             21

<210> SEQ ID NO 59
<211> LENGTH: 22
<212> TYPE: RNA
<213> ORGANISM: HOMO SAPIENS

<400> SEQUENCE: 59
guagauucuc cuucuaugag ua                                            22

<210> SEQ ID NO 60
<211> LENGTH: 22
<212> TYPE: RNA
<213> ORGANISM: HOMO SAPIENS

<400> SEQUENCE: 60
cguggauauu ccuucuaugu uu                                            22

<210> SEQ ID NO 61
<211> LENGTH: 22
<212> TYPE: RNA
<213> ORGANISM: HOMO SAPIENS

<400> SEQUENCE: 61 agugggaac ccuuccauga gg                                             22

<210> SEQ ID NO 62
```

```
<211> LENGTH: 21
<212> TYPE: RNA
<213> ORGANISM: HOMO SAPIENS

<400> SEQUENCE: 62
cagcagcaca cugugguuug u                                              21

<210> SEQ ID NO 63
<211> LENGTH: 21
<212> TYPE: RNA
<213> ORGANISM: HOMO SAPIENS

<400> SEQUENCE: 63
auccuugcua ucugggugcu a                                              21

<210> SEQ ID NO 64
<211> LENGTH: 22
<212> TYPE: RNA
<213> ORGANISM: HOMO SAPIENS

<400> SEQUENCE: 64
uauucaggaa gguguuacuu aa                                             22

<210> SEQ ID NO 65
<211> LENGTH: 21
<212> TYPE: RNA
<213> ORGANISM: HOMO SAPIENS

<400> SEQUENCE: 65
uacugcagac aguggcaauc a                                              21

<210> SEQ ID NO 66
<211> LENGTH: 22
<212> TYPE: RNA
<213> ORGANISM: HOMO SAPIENS

<400> SEQUENCE: 66
caaaacuggc aauuacuuuu gc                                             22

<210> SEQ ID NO 67
<211> LENGTH: 22
<212> TYPE: RNA
<213> ORGANISM: HOMO SAPIENS

<400> SEQUENCE: 67
acuuguaugc uagcucaggu ag                                             22

<210> SEQ ID NO 68
<211> LENGTH: 21
<212> TYPE: RNA
<213> ORGANISM: HOMO SAPIENS

<400> SEQUENCE: 68
guguugaaac aaucucuacu g                                              21

<210> SEQ ID NO 69
<211> LENGTH: 24
<212> TYPE: RNA
<213> ORGANISM: HOMO SAPIENS

<400> SEQUENCE: 69
acuggcuagg gaaaaugauu ggau                                           24
```

```
<210> SEQ ID NO 70
<211> LENGTH: 19
<212> TYPE: RNA
<213> ORGANISM: HOMO SAPIENS

<400> SEQUENCE: 70
ugcgccucgg gugagcaug                                               19

<210> SEQ ID NO 71
<211> LENGTH: 21
<212> TYPE: RNA
<213> ORGANISM: HOMO SAPIENS

<400> SEQUENCE: 71
ucuucaaccu caggacuugc a                                            21

<210> SEQ ID NO 72
<211> LENGTH: 24
<212> TYPE: RNA
<213> ORGANISM: HOMO SAPIENS

<400> SEQUENCE: 72
uggggagcug aggcucuggg ggug                                         24

<210> SEQ ID NO 73
<211> LENGTH: 21
<212> TYPE: RNA
<213> ORGANISM: HOMO SAPIENS

<400> SEQUENCE: 73
aagugaucua aaggccuaca u                                            21

<210> SEQ ID NO 74
<211> LENGTH: 22
<212> TYPE: RNA
<213> ORGANISM: HOMO SAPIENS

<400> SEQUENCE: 74
ugcuggauca gugguucgag uc                                           22

<210> SEQ ID NO 75
<211> LENGTH: 22
<212> TYPE: RNA
<213> ORGANISM: HOMO SAPIENS

<400> SEQUENCE: 75
uggguggucu ggagauuugu gc                                           22

<210> SEQ ID NO 76
<211> LENGTH: 22
<212> TYPE: RNA
<213> ORGANISM: HOMO SAPIENS

<400> SEQUENCE: 76
ugugagguug gcauuguugu cu                                           22

<210> SEQ ID NO 77
<211> LENGTH: 23
<212> TYPE: RNA
<213> ORGANISM: HOMO SAPIENS

<400> SEQUENCE: 77
cggcccgggc ugcugcuguu ccu                                          23
```

```
<210> SEQ ID NO 78
<211> LENGTH: 22
<212> TYPE: RNA
<213> ORGANISM: HOMO SAPIENS

<400> SEQUENCE: 78
uagucccuuc cuugaagcgg uc                                              22

<210> SEQ ID NO 79
<211> LENGTH: 22
<212> TYPE: RNA
<213> ORGANISM: HOMO SAPIENS

<400> SEQUENCE: 79
aacuccaaac acucaaaacu ca                                              22

<210> SEQ ID NO 80
<211> LENGTH: 20
<212> TYPE: RNA
<213> ORGANISM: HOMO SAPIENS

<400> SEQUENCE: 80
gaaucggaaa ggaggcgccg                                                 20

<210> SEQ ID NO 81
<211> LENGTH: 22
<212> TYPE: RNA
<213> ORGANISM: HOMO SAPIENS

<400> SEQUENCE: 81
caguggccag agcccugcag ug                                              22

<210> SEQ ID NO 82
<211> LENGTH: 20
<212> TYPE: PRT
<213> ORGANISM: Artificial sequence
<220> FEATURE:
<223> OTHER INFORMATION: B-hairpin peptide sequence

<400> SEQUENCE: 82

Val Leu Thr Lys Val Lys Thr Lys Val Asn Gly Thr Lys Val Glu Val
1               5                   10                  15

Lys Val Leu Val
            20

<210> SEQ ID NO 83
<211> LENGTH: 22
<212> TYPE: RNA
<213> ORGANISM: HOMO SAPIENS

<400> SEQUENCE: 83
acacacuucc uuacauucca uu                                              22

<210> SEQ ID NO 84
<211> LENGTH: 21
<212> TYPE: RNA
<213> ORGANISM: HOMO SAPIENS

<400> SEQUENCE: 84
cugucaauuc auaggucauu u                                               21

<210> SEQ ID NO 85
<211> LENGTH: 22
```

```
<212> TYPE: RNA
<213> ORGANISM: HOMO SAPIENS

<400> SEQUENCE: 85
ugagguagua gguuguaugg uu                                          22

<210> SEQ ID NO 86
<211> LENGTH: 21
<212> TYPE: RNA
<213> ORGANISM: HOMO SAPIENS

<400> SEQUENCE: 86
uaauuuuaug uauaagcuag u                                           21

<210> SEQ ID NO 87
<211> LENGTH: 18
<212> TYPE: RNA
<213> ORGANISM: HOMO SAPIENS

<400> SEQUENCE: 87 ggugggggu guuguuuu                                                18

<210> SEQ ID NO 88
<211> LENGTH: 23
<212> TYPE: RNA
<213> ORGANISM: HOMO SAPIENS

<400> SEQUENCE: 88
ggucuaggcc cggugagaga cuc                                         23

<210> SEQ ID NO 89
<211> LENGTH: 22
<212> TYPE: RNA
<213> ORGANISM: HOMO SAPIENS

<400> SEQUENCE: 89
ggggcuguga uugaccagca gg                                          22

<210> SEQ ID NO 90
<211> LENGTH: 24
<212> TYPE: RNA
<213> ORGANISM: HOMO SAPIENS

<400> SEQUENCE: 90
uuaaugcuaa ucgugauagg gguu                                        24

<210> SEQ ID NO 91
<211> LENGTH: 22
<212> TYPE: RNA
<213> ORGANISM: HOMO SAPIENS

<400> SEQUENCE: 91
uagguaguuu ccuguuguug gg                                          22

<210> SEQ ID NO 92
<211> LENGTH: 22
<212> TYPE: RNA
<213> ORGANISM: HOMO SAPIENS

<400> SEQUENCE: 92
auagcagcau gaaccugucu ca                                          22

<210> SEQ ID NO 93
```

```
<211> LENGTH: 21
<212> TYPE: RNA
<213> ORGANISM: HOMO SAPIENS

<400> SEQUENCE: 93
auagcagcau aagccugucu c                                              21

<210> SEQ ID NO 94
<211> LENGTH: 24
<212> TYPE: PRT
<213> ORGANISM: Artificial Sequence
<220> FEATURE:
<223> OTHER INFORMATION: B-hairpin peptide sequence
<220> FEATURE:
<221> NAME/KEY: misc_feature
<222> LOCATION: (1)..(1)
<223> OTHER INFORMATION: Xaa can be any one of F, I, L, M, T, V, W, and
      Y, or is not present
<220> FEATURE:
<221> NAME/KEY: misc_feature
<222> LOCATION: (2)..(2)
<223> OTHER INFORMATION: Xaa can be any amino acid, or is not present if
      X1 is not present
<220> FEATURE:
<221> NAME/KEY: misc_feature
<222> LOCATION: (3)..(3)
<223> OTHER INFORMATION: Xaa can be any one of F, I, L, M, T, V, W, and
      Y, or is not present
<220> FEATURE:
<221> NAME/KEY: misc_feature
<222> LOCATION: (4)..(4)
<223> OTHER INFORMATION: Xaa can be any amino acid, or is not present if
      X3 is not present
<220> FEATURE:
<221> NAME/KEY: misc_feature
<222> LOCATION: (5)..(5)
<223> OTHER INFORMATION: Xaa can be any one of F, I, L, M, T, V, W, and
      Y
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any one of F, I, L, M, T, V, W, and
      Y
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (9)..(9)
<223> OTHER INFORMATION: Xaa can be any one of F, I, L, M, T, V, W, and
      Y
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (11)..(11)
<223> OTHER INFORMATION: Xaa can be any one of F, I, L, M, T, V, W, and
      Y
<220> FEATURE:
<221> NAME/KEY: misc_feature
<222> LOCATION: (14)..(14)
<223> OTHER INFORMATION: Xaa can be any one of F, I, L, M, T, V, W, and
      Y
<220> FEATURE:
<221> NAME/KEY: misc_feature
<222> LOCATION: (15)..(15)
<223> OTHER INFORMATION: Xaa can be any amino acid
<220> FEATURE:
<221> NAME/KEY: misc_feature
<222> LOCATION: (16)..(16)
```

```
<223> OTHER INFORMATION: Xaa can be any one of F, I, L, M, T, V, W, and
      Y
<220> FEATURE:
<221> NAME/KEY: misc_feature
<222> LOCATION: (17)..(17)
<223> OTHER INFORMATION: Xaa can be any amino acid
<220> FEATURE:
<221> NAME/KEY: misc_feature
<222> LOCATION: (18)..(18)
<223> OTHER INFORMATION: Xaa can be any one of F, I, L, M, T, V, W, and
      Y
<220> FEATURE:
<221> NAME/KEY: misc_feature
<222> LOCATION: (19)..(19)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any one of F, I, L, M, T, V, W, and
      Y
<220> FEATURE:
<221> NAME/KEY: misc_feature
<222> LOCATION: (21)..(21)
<223> OTHER INFORMATION: Xaa can be any amino acid, or is not present if
      X3 is not present
<220> FEATURE:
<221> NAME/KEY: misc_feature
<222> LOCATION: (22)..(22)
<223> OTHER INFORMATION: Xaa can be any one of F, I, L, M, T, V, W, and
      Y, or is not present if X3 is not present
<220> FEATURE:
<221> NAME/KEY: misc_feature
<222> LOCATION: (23)..(23)
<223> OTHER INFORMATION: Xaa can be any amino acid, or is not present if
      X1 is not present
<220> FEATURE:
<221> NAME/KEY: misc_feature
<222> LOCATION: (24)..(24)
<223> OTHER INFORMATION: Xaa can be any one of F, I, L, M, T, V, W, and
      Y, or is not present if X1 is not present

<400> SEQUENCE: 94

Xaa Xaa Xaa Xaa Xaa Xaa Xaa Xaa Xaa Xaa Xaa Asn Gly Xaa Xaa Xaa
1               5                   10                  15

Xaa Xaa Xaa Xaa Xaa Xaa Xaa Xaa
            20
```